United States Patent [19]

Ferrari et al.

[11] Patent Number: 6,100,278

[45] Date of Patent: Aug. 8, 2000

[54] N-(ARYLSULPHONYL)AMINO ACID DERIVATIVES, PROCESS FOR THEIR PREPARATION AND PHARMACEUTICAL COMPOSITIONS CONTAINING THEM

[75] Inventors: Bernard Ferrari, Les Matelles; Jean Gougat, Grabels; Claude Muneaux; Yvette Muneaux, both of Les Matelles; Pierre Perreaut, St. Clement de Riviere; Claudine Planchenault, St. Georges d'Orques, all of France

[73] Assignee: Sanofi-Synthelabo, Paris, France

[21] Appl. No.: 09/434,333

[22] Filed: Nov. 4, 1999

Related U.S. Application Data

[62] Division of application No. 09/101,214, filed as application No. PCT/FR97/00026, Jan. 7, 1997, Pat. No. 6,015,812.

[30] Foreign Application Priority Data

Jan. 11, 1996 [FR] France .................................. 96 00269

[51] Int. Cl.[7] ...................... A61K 31/4709; A61P 19/02; C07D 401/14
[52] U.S. Cl. .......................... 514/314; 546/141; 546/143; 546/157; 546/172
[58] Field of Search .................... 546/143, 172; 514/314

[56] References Cited

FOREIGN PATENT DOCUMENTS 614911   9/1994   European Pat. Off. .

OTHER PUBLICATIONS

Robinson et al., Tetrahedron, 49(48), 1993, pp. 11329–11340.
Beilstein: Registry No. 6609829. (1994).
Beilstein: Registry No. 3458151. (1992).
Busson et al., J. Org. Chem., 43(23), 1978, pp. 4438–4441.
Beilstein: Registry No. 419229. (1993).
Carlson et al., J. Org. Chem., 31(7), 1966, pp. 2385–2386.
Beilstein: Registry No. 454128. (1993).
Burke et al., Exp. Opin. Ther. Patents, 5(4), 1995, pp. 331–339.
Wagner, *Chemical Abstracts*, vol. 107, No. 92532, 1987.

*Primary Examiner*—Robert W. Ramsuer
*Attorney, Agent, or Firm*—Michael D. Alexander

[57] ABSTRACT

The invention relates compounds of formula

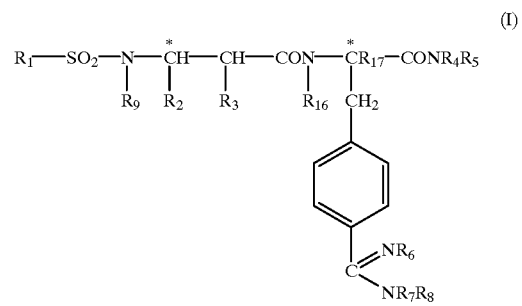

in which $R_1$ to $R_9$, $R_{16}$ and $R_{17}$ are as defined in claim 1.

These compounds are pharmacologically active.

32 Claims, No Drawings

N-(ARYLSULPHONYL)AMINO ACID DERIVATIVES, PROCESS FOR THEIR PREPARATION AND PHARMACEUTICAL COMPOSITIONS CONTAINING THEM

CROSS REFERENCE TO RELATED APPLICATIONS

This application is a divisional of U.S. patent application Ser. No. 09/101,214, filed Jul. 2, 1998 now U.S. Pat. No. 6,015,812, which is the U.S. national phase of PCT application PCT/FR97/00026, filed Jan. 7, 1997, which claimed priority of French application 9600269, filed Jan. 11, 1996. The entire disclosure of each of these documents is incorporated herein by reference.

The present invention relates to novel N-(arylsulphonyl) amino acid derivatives, to their preparation and to pharmaceutical compositions containing them.

These compounds have affinity for bradykinin (BK) receptors. Bradykinin is a nonapeptide belonging, like the decapeptide kallidin, to the class of kinins and which shows physiological activity in the cardiovascular field and as a mediator in inflammation and pain. Several bradykinin receptors are distinguished: the $B_1$ and $B_2$ receptors (D. Regoli et, al., Pharmacol. Rev., 1980, 32, 1–46). More precisely, the $B_2$ receptors are the bradykinin and kallidin receptors: they are predominant and are normally found in most tissues; the $B_1$ receptors are the receptors specific for [des-$Arg^9$] bradykinin and for [des-$Arg^{10}$] kallidin: they are induced during inflammatory processes.

Bradykinin receptors have been cloned for different species, in particular for the human species: $B_1$ receptor : J. G. Menke et al., J. Biol. Chem., 1994, 269 (34) 21583–21586; $B_2$ receptor : J. F. Hess, Biochem. Biophys. Res. Commun., 1992,,184, 260–268.

The reviews: Drug News and Perspectives, 1994, 7 (10), 603–611 and Exp. Opin. Ther. Patents, 1995, 5 (4), 331–340, give an account on bradykinin-receptor antagonists. Many antagonists described have peptide structures. As bradykinin-receptor antagonists, mention may be made in particular of HOE-140 (F. J. Hock, Brit. J. Pharmacol. 1991, 102, 769–773) for the $B_2$ receptor and [des-$Arg^9$, $Leu^8$] bradykinin for the $B_1$ receptor (M. N. Perkins et al., Pain, 1993, 53, 191–197). Recently, a $B_2$ receptor antagonist of non-peptide structure, SR 173657, has been described in Archiv Pharmacol., 1996, Suppl. 1, 354 (4), R6.

According to the present invention, a novel family of compounds having affinity for the bradykinin receptors has now been found; these compounds are N-(arylsulphonyl) amino acid derivatives.

Among the N-(arylsulphonyl)amino acid derivatives, some are known and have various pharmacological activities. Thus, compounds with anti-thrombotic activity are described in the European, German and international patents or patent applications EP 558,961, EP 236,163, EP 236,164, DD 155,954, DE 4,115,468 and WO 92/16549. In this field of activity, NAPAP, derived from N-(naphthalenesulphonyl)-glycine of formula:

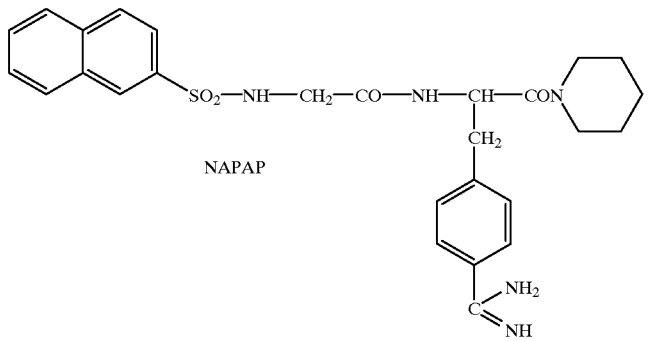

is described in Pharmazie, 1987, 42 (5), 346.

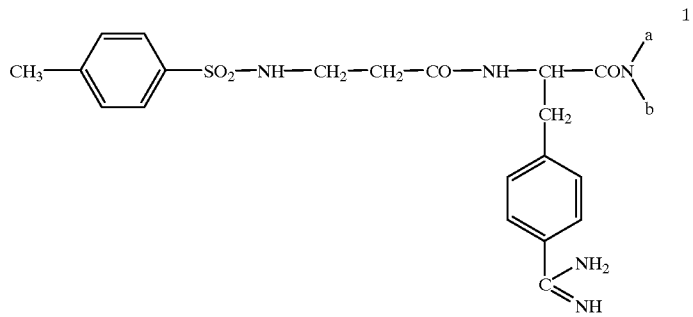

Furthermore, N-tosyl-β-alanine derivatives of formula:

in which a and b, together with the nitrogen atom to which they are attached, constitute a ring such as piperidine, pyrrolidine or morpholine, are described in Pharmazie, 1984, 39 (5), 315–317.

Similarly, N-(arylsulphonyl)proline derivatives have been cited as thrombin inhibitors in Pharmazie, 1986, 41 (4), 233–235 and Pharmazie, 1987, 42 (2), 114–116.

Moreover, patent application EP 614,911 describes compounds of formula:

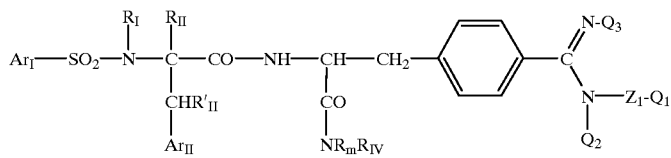

in which, in particular:

$Ar_I$ is a naphthyl, a phenyl, a quinolyl or an isoquinolyl, which are optionally substituted;

$Ar_{II}$ is a phenyl or a thienyl, which are optionally substituted;

$R_I$, $R_{II}$ and $R_{III}$ are, independently of each other, H or $(C_1-C_4)$alkyl;

or $R_I$ is nothing and N is linked to $Ar_{II}$ and optionally $R_{II}$ and $R'_{II}$ form a double bond;

or $R_I$ or $R_{II}$ is linked to $Ar_{II}$ and is a $(C_1-C_3)$ alkylene;

$R_{III}$ and $R_{IV}$, which may be identical or different, are H, $(C_1-C_4)$alkyl or form, together with the nitrogen atom to which they are attached, a $(C_5-C_7)$ heterocycle;

$Z_1$ is a $(C_1-C_{12})$alkylene;

$Q_1$ is methyl, amino, $(C_1-C_4)$alkoxycarbonylamino, $(C_1-C_4)$ alkylamino, di$(C_1-C_4)$alkylamino, pyrrolidinyl, piperidino, morpholino, piperazinyl, $(C_1-C_4)$alkyl-4-piperazinyl, amidino, $(C_1-C_4)$alkylamidino, guanidino, $(C_1-C_4)$alkylguanidino, pyridyl, imidazolyl, pyrimidinyl, indolyl, hydroxyl, $(C_1-C_4)$alkoxy, $(C_2-C_8)$ alkoxycarbonyl, amino$(C_1-C_4)$alkyl-N-$(C_1-C_4)$alkylamino, carbamoyl or phenyl, which is optionally substituted;

$Q_2$ is H or $(C_1-C_4)$alkyl;

$Q_3$ is H or $(C_1-C_4)$alkyl or $Q_1$ and $Q_3$ are linked to form a heterocycle and together are $(C_2-C_3)$alkylene when $Z_1$ is nothing, in the form of pure enantiomers or mixtures thereof in any proportion;

as well as the salts thereof with acids.

These compounds have affinity for the biological receptors of the neuropeptide Y.

According to the present invention, novel compounds have now been found which have, unexpectedly, affinity for the bradykinin receptors.

The subject of the present invention is the compounds of formula:

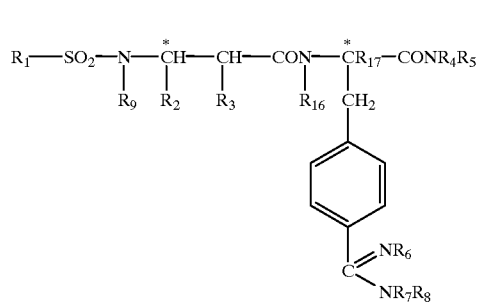

in which:

$R_1$ is a phenyl, a naphthyl, a tetrahydronaphthyl, a quinolyl or an isoquinolyl, the said rings being unsubstituted or substituted one or more times with $R_{10}$;

$R_2$ is a phenyl which is unsubstituted or substituted one or more times with $R_{11}$, a phenyl$(C_1-C_4)$alkyl which is unsubstituted or substituted one or more times on the phenyl with $R_{11}$, a naphthyl which is unsubstituted or substituted one or more times with $R_{11}$, a cyclohexyl which is unsubstituted or substituted one or more times with $R_{11}$;

or $R_2$ and $R_9$ are linked together and constitute a $(C_3-C_5)$ alkylene which is unsubstituted or substituted with $R_{12}$ or a $(C_2-C_4)$alkylene which is interrupted with an oxygen atom or a sulphur atom and is unsubstituted or substituted with $R_{12}$;

or $R_2$ and $R_9$, together with the carbon atom and the nitrogen atom to which they are attached, constitute tetrahydroisoquinoline which is unsubstituted or substituted one or more times with a halogen, a hydroxyl, a $(C_1-C_4)$alkyl, a $(C_1-C_4)$alkoxy or a benzyloxy;

$R_3$ is hydrogen or a hydroxyl;

$R_4$ and $R_5$ are each independently hydrogen or a $(C_1-C_4)$ alkyl;

or $R_4$ and $R_5$, together with the nitrogen atom to which they are attached, constitute a heterocyclic radical chosen from 1-pyrrolidinyl, 1-piperidyl, perhydro-1-azepinyl, 4-morpholinyl, 4-oxo-1-piperidyl, dihydro-1-pyrrolyl or dihydro-2-imidazolyl, the said heterocyclic radicals being unsubstituted or substituted one or more times with $R_{13}$;

$R_6$ is hydrogen and $R_6$ can also be $R_8$ when $R_7$ is hydrogen;

$R_7$ is hydrogen or a $(C_1-C_4)$alkyl;

$R_8$ is hydrogen; a benzyl which is unsubstituted or substituted on the phenyl one or more times with $R_{13}$; or a group $ZR_{14}$;

or $R_7$ and $R_8$, together with the nitrogen atom to which they are attached, constitute a heterocyclic radical chosen from 1-pyrrolidinyl, 1-piperidyl, 1-perhydro-1-azepinyl, 4-morpholinyl, tetrahydro-2-pyrimidinyl, 1-piperazinyl or 1-piperazinyl substituted in position 4 with a $(C_1-C_4)$ alkyl or a benzyl;

or, when $R_7$ is hydrogen, $R_6$ and Re are linked together to form a $(C_2-C_4)$alkylene which is unsubstituted or substituted one or more times with a $(C_1-C_4)$alkyl;

$R_9$ is hydrogen, a $(C_1-C_4)$alkyl or a phenyl$(C_1-C_4)$alkyl which is unsubstituted or substituted on the phenyl one or more times with $R_{11}$;

$R_{10}$ is a halogen, a $(C_1-C_4)$alkyl, a $(C_1-C_4)$alkoxy, a hydroxyl, an amino, a $(C_1-C_4)$alkylamino or a di$(C_1-C_4)$ alkylamino;

$R_{11}$ is a halogen, a $(C_1-C_4)$alkyl, a trifluoromethyl, a phenyl, a hydroxyl, a $(C_1-C_4)$alkoxy or a benzyloxy;

or $R_{11}$ is in the ortho position to the phenyl representing $R_2$ and forms with $R_3$ a methylene group or an ethylene group;

or $R_{11}$ is in the ortho position to the phenyl representing $R_2$ and forms with $R_9$ a methylene group or an ethylene group;

$R_{12}$ is a halogen, a $(C_1-C_4)$alkyl, a hydroxyl, a $(C_1-C_4)$ alkoxy, a benzyloxy, an oxo, a phenyl, an acetyloxy or a trifluoroacetyloxy;

$R_{13}$ is a $(C_1-C_4)$alkyl, a halogen or a hydroxyl;

$R_{14}$ is a methyl, an amino, a $(C_1-C_4)$alkylamino, a di $(C_1-C_4)$alkylamino, a tri $(C_1-C_4)$alkylammonium, an amidino, a $(C_1-C_4)$alkylamidino, a guanidino, a $(C_1-C_4)$alkylguanidino, a hydroxyl, a $(C_1-C_4)$alkoxy, a $(C_1-C_4)$alkoxycarbonyl, a group —AlkN($R_{15}$)Alk'N($R'_{15}$)$_2$, or a heterocyclic radical chosen from 1-pyrrolidinyl, 1-piperidyl, perhydro-1-azepinyl, pyridyl, imidazolyl, dihydroimidazolyl, imidazolidinyl, pyrimidinyl and indolyl;

$R_{15}$ and $R'_{15}$ are, independently of each other, hydrogen or a $(C_1-C_4)$alkyl;

$R_{16}$ is hydrogen or a methyl, or $R_{16}$ forms with $R_9$ a methylene group;

$R_{17}$ is hydrogen or a methyl;

Alk and Alk' are, independently of each other, a $(C_1-C_4)$ alkylene;

Z is a $(C_2-C_{12})$alkylene or a $(C_1-C_6)$alkylene which is interrupted or substituted with a $(C_5-C_7)$cycloalkyl or with a phenyl;

C* is an asymmetric carbon atom;

as well as the salts thereof with inorganic or organic acids.

The salts are generally prepared with pharmaceutically acceptable acids, but the salts of other acids which are useful for the purification or isolation of the compounds of formula (I) also form part of the invention. The pharmaceutically acceptable salts of the compounds of formula (I) are, for example, the hydrochloride, the hydrobromide, the sulphate, the methanesulphonate, the benzenesulphonate, the naphthalenesulphonate, the maleate, the fumarate, the citrate, the acetate, the gluconate, the dobesilate or the sultosilate.

The compounds of formula (I) comprise 2 (or possibly more) asymmetric carbon atoms and the 4 (or possibly more) pure enantiomers, as well as the mixture thereof in any proportion, are subjects of the invention.

The term halogen is understood to refer to chlorine, fluorine, bromine or iodine, chlorine and fluorine being preferred.

The terms, alkyl, alkylene and alkoxy are understood to refer, respectively, to a linear or branched alkyl radical, alkylene radical or alkoxy radical.

Those compounds of formula (I) are preferred in which:

$R_1$ is a phenyl, a naphthyl, a tetrahydronaphthyl, a quinolyl or an isoquinolyl, the said rings being unsubstituted or substituted one or more times with $R_{10}$;

$R_2$ is a phenyl which is unsubstituted or substituted one or more times with $R_{11}$, a phenyl($C_1-C_4$)alkyl which is unsubstituted or substituted one or more times on the phenyl with $R_{11}$, or a naphthyl which is unsubstituted or substituted one or more times with $R_{11}$;

or $R_2$ and $R_9$ are linked together and constitute a $(C_3-C_5)$ alkylene which is unsubstituted or substituted with $R_{12}$ or a $(C_2-C_4)$alkylene which is interrupted with an oxygen atom or a sulphur atom and is unsubstituted or substituted with $R_{12}$;

or $R_2$ and $R_9$ together with the carbon atom and the nitrogen atom to which they are attached, constitute tetrahydroisoquinoline which is unsubstituted or substituted one or more times with a halogen, a hydroxyl, a $(C_1-C_4)$alkyl, a $(C_1-C_4)$alkoxy or a benzyloxy;

$R_3$ is hydrogen or a hydroxyl;

$R_4$ and $R_5$ are each independently hydrogen or a $(C_1-C_4)$ alkyl;

or $R_4$ and $R_5$, together with the nitrogen atom to which they are attached, constitute a heterocyclic radical chosen from 1-pyrrolidinyl, 1-piperidyl, perhydro-1-azepinyl, 4-morpholinyl or 4-oxo-1-piperidyl, the said heterocyclic radicals being unsubstituted or substituted with $R_{13}$;

$R_6$ is hydrogen, $R_6$ can also be $R_8$ when $R_7$ is hydrogen;

$R_7$ is hydrogen or a $(C_1-C_4)$alkyl;

$R_8$ is hydrogen; a benzyl which is unsubstituted or substituted on the phenyl one or more times with $R_{13}$; or a group $ZR_{14}$;

or $R_7$ and $R_8$, together with the nitrogen atom to which they are attached, constitute a heterocyclic radical chosen from 1-pyrrolidinyl, 1-piperidyl, perhydro-1-azepinyl, 4-morpholinyl, 1-piperazinyl or 1-piperazinyl substituted in position 4 with a $(C_1-C_4)$alkyl or a benzyl;

or, when $R_7$ is hydrogen, $R_6$ and $R_8$ are linked together to form a $(C_2-C_4)$alkylene which is unsubstituted or substituted one or more times with a $(C_1-C_4)$alkyl;

$R_9$ is hydrogen, a $(C_1-C_4)$alkyl or a phenyl($C_1-C_4$)alkyl which is unsubstituted or substituted on the phenyl one or more times with $R_{11}$;

$R_{10}$ is a halogen, a $(C_1-C_4)$alkyl, a $(C_1-C_4)$alkoxy, a hydroxyl, an amino, a $(C_1-C_4)$alkylamino or a di($C_1-C_4$) alkylamino;

$R_{11}$ is a halogen, a $(C_1-C_4)$alkyl, a hydroxyl, a $(C_1-C_4)$ .alkoxy or a benzyloxy;

$R_{12}$ is a halogen, a $(C_1-C_4)$alkyl, a hydroxyl, a $(C_1-C_4)$ alkoxy, a benzyloxy, an oxo or a phenyl;

$R_{13}$ is a $(C_1-C_4)$alkyl, a halogen or a hydroxyl;

$R_{14}$ is a methyl, an amino, a $(C_1-C_4)$alkylamino, a di($C_1-C_4$)alkylamino, a tri($C_1-C_4$)alkylammonium, an amidino, a $(C_1-C_4)$alkylamidino, a guanidino, a $(C_1-C_4)$alkylguanidino, a hydroxyl, a $(C_1-C_4)$alkoxy, a $(C_1-C_4)$alkoxycarbonyl, a group —AlkN($R_{15}$)Alk'N($R_{15}$)$_2$, or a heterocyclic radical chosen from. 1-pyrrolidinyl, 1-piperidyl, perhydro-1-azepinyl, pyridyl, imidazolyl, dihydroimidazolyl, imidazolidinyl, pyrimidinyl and indolyl;

$R_{15}$ and $R'_{15}$ are, independently of each other, hydrogen or a $(C_1-C_4)$alkyl;

$R_{16}$ is hydrogen;

$R_{17}$ is hydrogen;

Alk and Alk' are, independently of each other, a $(C_1-C_4)$ alkylene;

Z is a $(C_2-C_{12})$alkylene or a $(C_1-C_6)$alkylene which is interrupted or substituted with a $(C_5-C_7)$cycloalkyl or with a phenyl;

as well as the salts thereof with inorganic or organic acids.

Certain values for the substituents are preferred. Thus, the preferred compounds of formula (I) are those which satisfy at least one of the following conditions:

a —$R_1$ is a naphthyl, a quinolyl or a trichlorophenyl; $R_2$, $R_3$, $R_4$, $R_5$, $R_6$, $R_7$, $R_8$, $R_9$, $R_{16}$ and $R_{17}$ being as defined above for formula I;

b —$R_2$ is a phenyl which is unsubstituted or substituted with $R_{11}$; $R_1$, $R_3$, $R_4$, $R_5$, $R_6$, $R_7$, $R_8$, $R_9$, $R_{16}$ and $R_{17}$ being as defined above for formula I;

c —NR$_4$R$_5$ is a 1-pyrrolidinyl group; $R_1$, $R_2$, $R_3$, $R_6$, $R_7$, $R_8$, $R_9$, $R_{16}$ and $R_{17}$ being as defined above for formula I;

d —C(NR$_6$)NR$_7$R$_8$ is a 4,5-dihydro-2-imidazolyl; $R_1$, $R_2$, $R_3$, $R_4$, $R_5$, $R_9$, $R_{16}$ and $R_{17}$ being as defined above for formula I;

e —$R_3$=$R_9$=$R_{16}$=$R_{17}$=H; $R_1$, $R_2$, $R_4$, $R_5$, $R_6$, $R_7$ and $R_8$ being as defined above for formula I;

and the salts thereof with inorganic or organic acids.

According to the invention, the preferred compounds are those of formula:

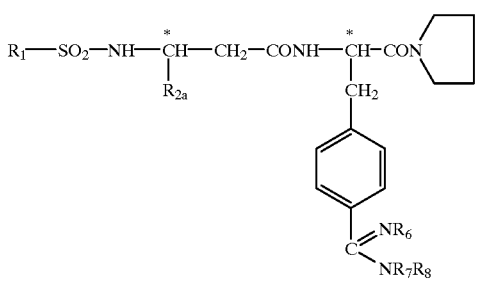

(Ia)

in which:

$R_{2a}$ is a phenyl which is unsubstituted or substituted in a meta or para position with $R_{11}$; a 1-naphthyl or a 2-naphthyl;

$R_1$, $R_6$, $R_7$, $R_8$ and $R_{11}$ are as defined above for (1);

and the salts thereof with inorganic or organic acids.

Most particularly, the preferred compounds are those of formula:

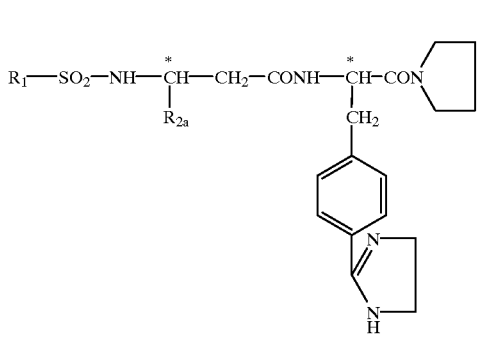

(I'a)

in which:

$R_{1a}$ is a 1-naphthyl, a 2-naphthyl, a 2,4,6-trichlorophenyl or a 2-quinolyl;

$R_{2a}$ is as defined above for (Ia);

and the salts thereof with inorganic or organic acids.

More particularly, the preferred compounds are those of formula (I'a) in which $R_{2a}$ is a phenyl which is unsubstituted or substituted in a meta or para position with $R_{11}$.

Most particularly, the preferred compounds are those of formula (I), (Ia) or (I'a) having (R,R) isomerism on the C*-labelled carbon atoms.

The following abbreviations are used in the description and in the claims:

Me: methyl
Et: ethyl
iPr: isopropyl
nBuOH: n-butanol
iPrOH: isopropanol
EtOH: ethanol
MeOH: methanol
Et$_2$O: ether:diethyl ether
DMF: dimethylformamide
DCM: dichloromethane
THF: tetrahydrofuran
AcOH: acetic acid
EtOAc: ethyl acetate
DIPEA: diisopropylethylamine
DMAP: 4-dimethylaminopyridine
DCC: 1,3-dicyclohexylcarbodiimide
DCU: dicyclohexylurea
NSuOH: N-hydroxysuccinimide
NSu: succinimido
NBS: N-bromosuccinimide
Fmoc: fluorenylmethoxycarbonyl
Boc: tert-butoxycarbonyl
(Boc)$_2$O: di-tert-butyl dicarbonate
Et$_3$N: triethylamine
Bn: benzyl
Pd/C: palladium-on-charcoal
Sephadex® LH 20: sold by Pharmacia
Sephadex® G 25: sold by Pharmacia
Alcalase®: Carlsberg subtilisin sold by Novo (Denmark)
Penicillin amidase: penicillin amidohydrolase, sold by Sigma
BOP: benzotriazol-1-yloxytris(dimethylamino) phosphonium hexafluorophosphate
K$_2$CO$_3$ potassium carbonate
K$_2$SO$_4$ : potassium sulphate
KHSO$_4$: potassium hydrogen sulphate
KHSO$_4$/K$_2$SO$_4$: solution of 16.66 g of KHSO$_4$ and 32.32 g of K$_2$SO$_4$ in 1 l of water
NaCl: sodium chloride
Na$_2$SO$_4$: sodium sulphate
MgSO$_4$: magnesium sulphate
NaOH: sodium hydroxide
NH$_4$OH: aqueous ammonia
HCl: hydrochloric acid
TFA: trifluoroacetic acid
hydrochloric ether: saturated solution of hydrogen chloride gas in diethyl ether
mPa.s: milliPascal/second
m.p.: melting point
RT: room temperature
NMR: nuclear magnetic resonance
DMSO: dimethyl sulphoxide
δ: chemical shift
s: singlet; bs: broad singlet; ds: doubled singlet; d: doublet; dd: doubled doublet; t: triplet; bt: broad triplet; q: quartet; quint: quintet; mt: multiplet; m: unresolved multiplet The subject of the present invention is also the process for the preparation of the compounds of formula (I) and the salts thereof. This process, referred to as process 1, is characterized in that:

a1) a compound of formula:

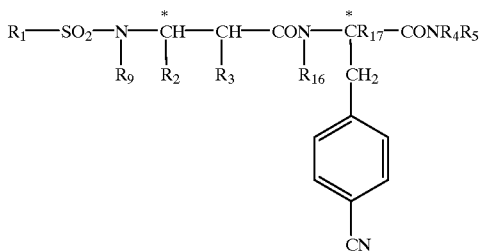
(II)

in which $R_1$, $R_2$, $R_3$, $R_4$, $R_5$, $R_9$, $R_{16}$, $R_{17}$ and C* have the definitions given above for (I), in the form of a pure enantiomer or a mixture of isomers in any proportion, is treated with an alcohol of formula R—OH in which R is a $(C_1-C_4)$alkyl, in acidic medium, in order to form an intermediate imidate which is reacted with an amine of. formula $HNR_7R_8$ (III) or a diamine of formula $H_2NR_6R_8NH_2$ (IV) in which $R_6$, $R_7$ and $R_8$ have the definitions given above for (I);

b1) the compound of formula (I) thus obtained is isolated in base form or salt form, c1) where appropriate, another salt of the compound of formula (I) is prepared.

Many processes for the synthesis of amidines are described in the book "The chemistry of amidines and imidates", D. G. Neilson, Ed. Saul Pataï, Wiley and Sons, 1975, 389–394. The preparation of certain amidines is described precisely in patent application EP 614,911 A.

The formation of the imidate is preferably carried out in a strong acid medium, whereas the imido ester in free base form or in salt form is reacted with the amine (III) or the diamine (IV) in an inert polar solvent, for example an alcohol, at a temperature of between 0° C. and the reflux temperature of the solvent.

The intermediate imidate is reacted with an amine whose formula depends on that of the compound (I) which it is desired to obtain. In order to prepare a compound of formula (I) in which $R_6=H$, an amine $HNR_7R_8$ is reacted; in order to prepare a compound of formula (I) in which $R_6=R_8$ and $R_7=H$, two moles of an amine of formula $H_2NR_8$ are reacted per mole of imidate; in order to prepare a compound of formula (I) in which $R_7$ is hydrogen and $R_6$ and $R_8$ are linked together to form a $(C_2-C_4)$alkylene which is unsubstituted or substituted one or more times with an alkyl, a diamine of formula $H_2NR_6R_8NH_2$ is reacted.

Most of the amines (III) and of the diamines (IV) are known and the novel products can be prepared by applying principles and methods that are well known to those skilled in the art. For example, for the derivatives in which $R_{14}$ is an imidazolyl, reference will be made to U.S. Pat. No. 3,881,016 and to the publication Synth. Communic. 1987, 17 (21), 223–227.

The compounds of formula (I) in which $R_{14}$ is $NH_2$ or alkylamino can be prepared by hydrolysis of the compounds of formula (I) in which $R_{14}$ contains a t-butoxycarbonylamino group, which is in turn obtained according to Synth. Commun. 1990, 20 (16), 2559–2564.

The compounds of formula (I) in which $R_{14}$ is a substituted or unsubstituted guanidino group can be prepared by the action on the compound of formula (I), in which $R_{14}=NH_2$, of a compound of formula:

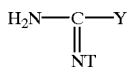

in which T is H or $(C_1-C_4)$alkyl and Y is a nucleofugal group, such as $SO_3H$, for example, aminoiminomethanesulphonic acid (under the conditions described in Tetrahedron Letters, 1988, 3183–3186) or N-methylaminoiminomethanesulphonic acid (obtained according to the process described in J. Org. Chem., 1986, 51(10), 1882).

The action of an amine (III) of formula $H_2NR_8$ in excess on the imidate resulting from the reaction of ROH with a compound of formula (II) leads to the formation of a mixture of two compounds of formula (I): for one $R_6=R_7=H$ and for the other $R_6=R_8$ and $R_7=H$.

The compounds of formula (I) in which $R_6$ and $R_8$ together form a $(C_2-C_4)$alkylene which is unsubstituted or substituted one or more times with a $(C_1-C_4)$alkyl can be prepared in a manner which is known per se, by the action of a diamine $H_2N$—$R_6R_8$—$NH_2$ on the imido ester or optionally by the action of the same diamine, one of the functions of which is protected by a labile group (such as Boc or Fmoc for example) which will be removed before cyclization.

The compounds of formula (I) in which $R_{14}$ is a dihydroimidazole can be prepared by the action of an alcohol in acidic medium on a compound of formula:

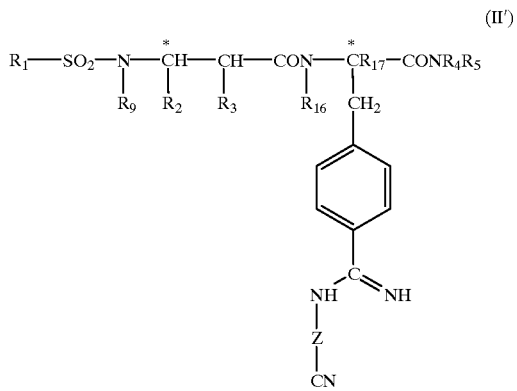
(II')

in order to form an intermediate imidate, which is reacted with an appropriate amine according to the usual methods.

The nitrites of formula (II) are prepared using the standard methods of peptide chemistry, for example those described in The Peptides Ed. E. Gross and J. Meienhofer, Academic Press, 1979, 1, 65–104. Known methods make it possible to carry out peptide couplings without racemization of the carbon atoms of each constituent amino acid; furthermore, the β-substituted β-alanines for which the chiral carbon is not adjacent to the carboxyl group are reputed as not suffering racemization (Ann. Rev. Biochem., 1986, 55, 855–878). Moreover, patent application EP 236,163 describes processes which allow the chirality of each amino acid to be conserved.

In general, the coupling reactions between the 2 amino acids take place at temperatures of between 0° C. and 40° C. in an inert solvent such as dichloromethane, acetonitrile, tetrahydrofuran or dimethylformamide, in the presence of a coupling agent and of at least one equivalent of a tertiary amine such as triethylamine, N-ethylmorpholine or diisopropylethylamine.

Thus, the preparation of a nitrile of formula (II) can be carried out according to one of the synthetic routes below.

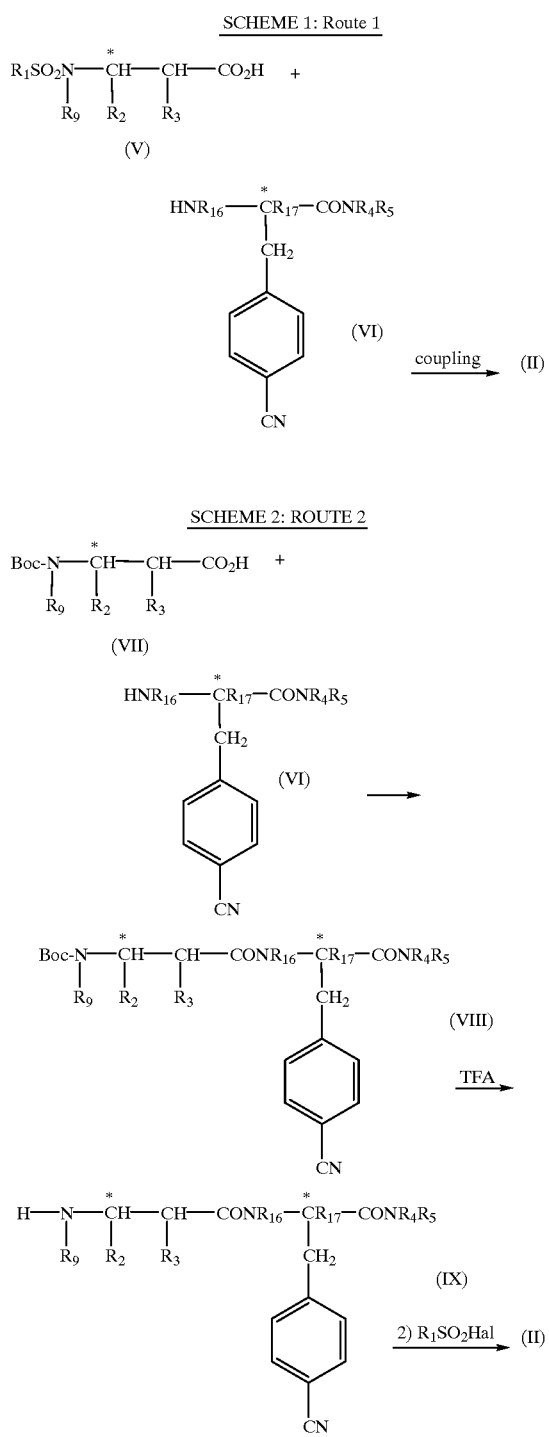

In order to prepare a compound of formula (V), which is useful in route 1, the radical $R_1SO_2$ is introduced in a conventional manner by the action of a sulphonyl halide of formula: $R_1SO_2Hal$ in which $R_1$ is as defined above for (I) and Hal is a halogen, preferably chlorine, on a-compound of formula:

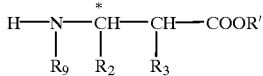

in which $R_2$, $R_3$ and $R_9$ have the meanings given above for (I) and R' is hydrogen or a $(C_1–C_4)$alkyl.

A compound of formula (V) in which $R_3$ is hydrogen can also be prepared in 2 steps: firstly, a compound of formula:

in which Y is $R_1SO_2$ or a protecting group such as Boc or Fmoc, after which the carbon chain is extended by one atom using known methods, then, if necessary, the protecting group is removed and a sulphonyl halide of formula $R_1SO_2Hal$ is reacted and, lastly, the group R' is removed, if it is other than H.

This procedure is suitable, for example, when $R_2$ and $R_9$ are linked together and constitute a $(C_3–C_5)$-alkylene which is unsubstituted or substituted with $R_{12}$ or a $(C_2–C_4)$-alkylene which is interrupted by an oxygen atom or a sulphur atom which is unsubstituted or substituted one or more times with $R_{12}$.

The sulphonyl halides are known or are prepared by known methods.

The compounds of formula (VI) are prepared by the action of an amine $HNR_4R_5$ on an amino acid of formula:

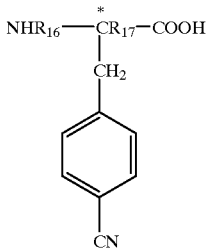

in which the amine is protected, for example by a Boc or Fmoc group, followed by the removal of the protecting group.

In the reaction sequence of route 2, the amine is deprotected in acidic medium (TFA) and the radical $R_1SO_2$ is introduced in a conventional manner by the action of a sulphonyl halide of formula: $R_1SO_2Ha'l$ in which $R_1$ is as defined above for (I) and Hal is a halogen, preferably chlorine.

In route 1, as in route 2, the group $R_1SO_2$ is introduced in the presence of a base, optionally in a two-phase medium, in the presence of a phase-transfer catalyst.

A substituent $R_9$ can be introduced into a compound of formula (II) in which $R_9$=H by known methods, for example by the action of a halide of formula $R_9Hal$, in which Hal is a halogen atom, for example chlorine.

The compounds of formula (II) in which $R_9$ and $R_{16}$ together form a methylene group are prepared by the action of para-formaldehyde on compounds of formula (II) in which $R_9$=$R_{16}$=H.

The compounds of formula (II) are novel and constitute a further aspect of the present invention.

Certain compounds of formula (V), which are toluene-sulphonamide or phenylsulphonamide derivatives, have been described in the following publications:

Tetrahedron, 1993, 49 (48), 11329–11340;
Centralblatt, 1929, II, 1398;
J. Org. Chem., 1978, 43(23), 4438–4441;
J. Org. Chem., 1966, 31(7), 2385–2386.

Thus, the compounds of formula:

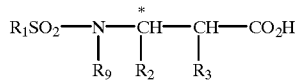

(V)

in which $R_1$, $R_2$, $R_3$, $R_9$ and $C^*$ are as defined for (I); it being understood that:

when $R_1$ is phenyl or p-tolyl and $R_3$ is hydrogen, then $R_2$ and $R_9$, together with the carbon and nitrogen atoms to which they are attached, are not pyrrolidinyl or 6,7-dimethoxy-1,2,3,4-tetrahydroisoquinolyl, and when $R_1$ is p-tolyl and $R_9$ is hydrogen, then $R_2$ is not an unsubstituted phenyl;

are novel and form part of the invention.

In order to prepare a compound of formula (I) in which $R_9$ and $R_{11}$ together form a methylene or ethylene group, a beta-amino acid of formula (XIII)

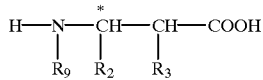

(XIII)

in which $R_9$ and $R_{11}$ form a methylene or ethylene group, is prepared using known methods, for example the one described in J. Org. Chem., 1987, 52, 616–622.

In order to prepare a beta-amino acid of formula (XIII) in which $R_3$ and $R_{11}$ together form a methylene or ethylene group, known methods are used. Thus, methyl 1-aminoindane-2-carboxylate is prepared in 3 steps from 1-indanone: according to J. Med. Chem., 1970, 650, the action of methyl carbonate in the presence of sodium hydride makes it possible to obtain methyl (1-oxo)indane-2-carboxylate, then, according to J. Heterocycl. Chem., 1974, 11, 982, methyl 1-hydroxyiminoindan-2-carboxylate is prepared and, lastly, the hydroxylamine is reduced to amine in the presence of a catalyst.

1-Amino-1,2,3,4—tetrahydronaphthalene-2-carboxylic acid can be prepared according to the method described in J. Chromatogr., A 1994, 676, 297–302. Alternatively, according to another process, when the amidine group $C(=NR_6)NR_7R_8$ contains no function liable to react in a subsequent step under the peptide coupling conditions, an amino acid derivative containing the amidine group can be prepared from the corresponding derivative containing a cyano group, and the couplings required to obtain a compound according to the invention can then be carried out.

Thus, according to a further aspect, the subject of the present invention is another process for the preparation of a compound of formula (I), which is referred to as process 2, characterized in that:

a2) a compound of formula:

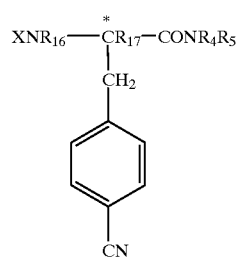

(VIa)

in which X is hydrogen Dr a Boc group and $R_4$, $R_5$ and $C^*$ are as defined for (I), in the form of a pure enantiomer or a mixture of isomers in any proportion, is treated with an alcohol of formula R—OH in which R is a $(C_1-C_4)$alkyl, in acidic medium, in order to form an intermediate imidate which is reacted with an amine of formula $HNR_7R_8$ (III) or a diamine of formula $HNR_6R_8NH_2$ (IV) in which $R_6$, $R_7$ and $R_8$ have the definitions given above for (I):

b2) the compound thus obtained, of formula:

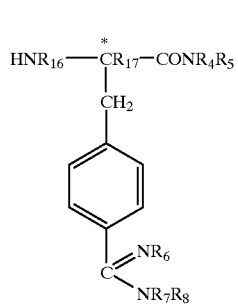

(XI)

is coupled
either with a compound of formula:

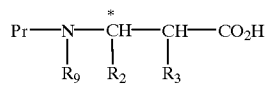

(XII)

in which $R_2$, $R_3$ and $R_9$ are as defined for (I) and Pr is a protecting group, for example Boc or Fmoc, then, after deprotection of the amine in acidic medium, a sulphonyl halide of formula $R_1SO_2Hal$ in which $R_1$ is as defined for (I) and Hal is a halogen, for example chlorine, is reacted;

or with a compound of formula:

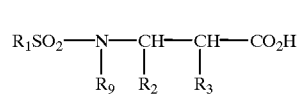

(V)

in which $R_1$, $R_2$, $R_3$ and $R_9$ are as defined for (I):

c2) the compound of formula (I) thus obtained is isolated in base form or in salt form;

d2) where appropriate, another salt of the compound of formula (I) is prepared.

The compounds of formulae (VI) and (XI) in optically pure form can be obtained from an ester, for example the racemic ethyl ester of 4-cyanophenylalanine, according to the reaction scheme described below:
SCHEME 3
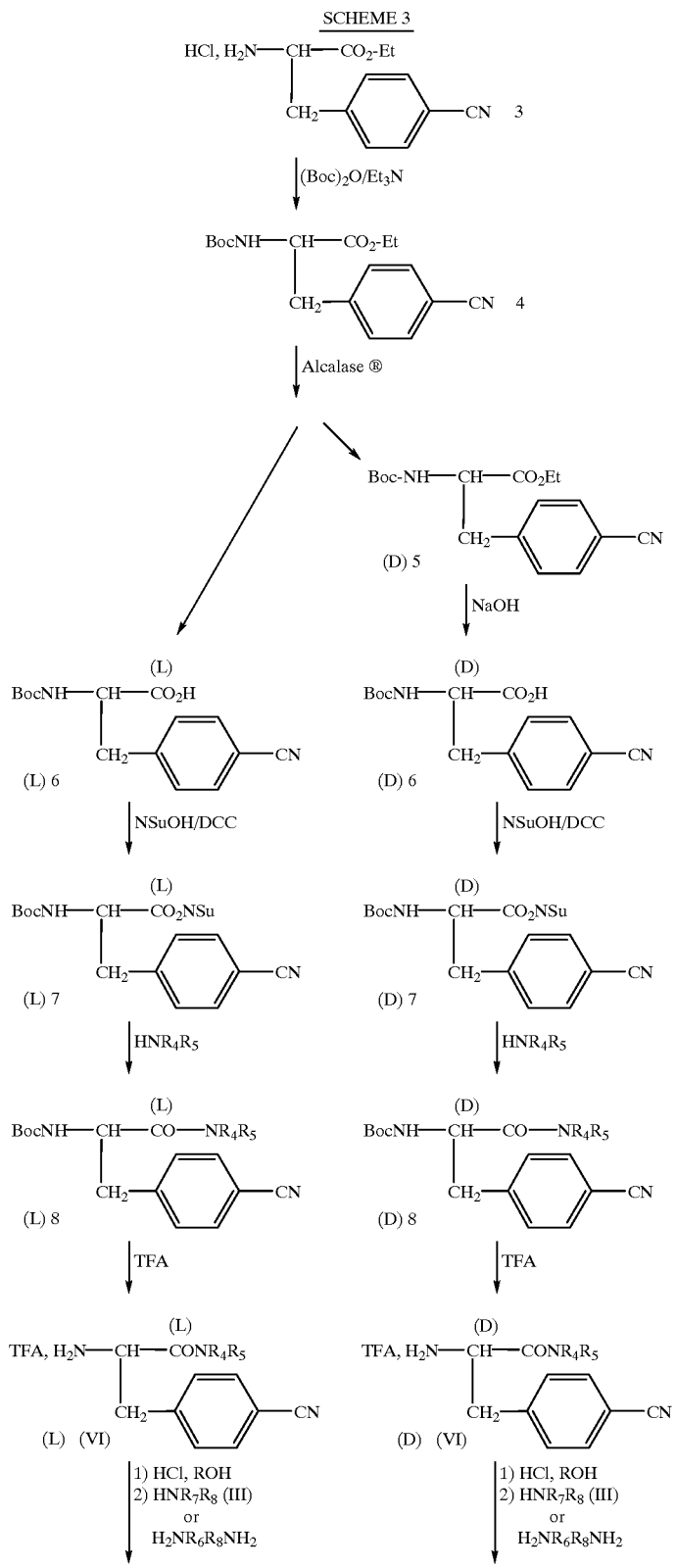

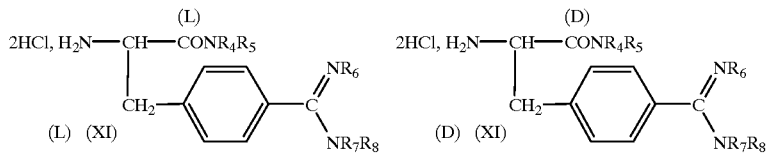

The racemic ethyl ester of 4-cyanophenylalanine is described in patent application EP 614,911 A. The amine function of this compound is protected in a conventional manner, by the action of (Boc)$_2$O in the presence of triethylamine. The action -of an enzyme, Alcalase®, on the compound 4 thus obtained makes it possible to selectively hydrolyse the ester function of the amino acid of (L) configuration and thus to isolate each of the compounds 5 and 6 in optically pure form (Synthesis, 1983, 1041–1043).

The compound of (L) configuration is isolated in acid form: (L) 6. The compound of (D) configuration is isolated in the form of an ethyl ester: (D) 5; this compound is hydrolysed with sodium hydroxide in order to obtain the acid form: (D) 6. Each of these 2 compounds of formula 6 is then treated with N-hydroxysuccinimide in an inert solvent such as DMF or dioxane, in the presence of a coupling agent such as DCC in order to obtain a compound of formula 7. The action of an amine HNR$_4$R$_5$, followed by the action of trifluoroacetic acid, makes it possible to prepare the compounds of formulae (L) (VI) and (D) (VI); the conventional reactions described above are then carried out in order to obtain the desired amidines of formulae (L) (XI) and (D) (XI).

The beta-amino acids of formula XIII:

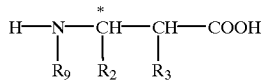

(XIII)

or the corresponding aliphatic esters are known or can be prepared by various methods, for example according to J. Am. Chem., 1936, 58, 299. One specific way of preparing the beta-amino acids consists in carrying out a chain extension starting with an alpha-amino acid, according to Tetrahedron, 1994, 50, 9457–9470 or according to J. Chem. Soc., Perkin Transact. II, 1977, 370.

More specifically, the preparation of certain beta-amino acids of formula (XIV) H$_2$N—CH(R$_2$)—CH$_2$—COOH is described in the following publications or patents.

| R$_2$ | Reference |
|---|---|
|  | (R, S): commercial<br>(R): Ber. 1910, 43, 2020<br>(S) J. Org. Chem., 1991, 56, 5883<br>J. Chem. Soc. Chem. Commun., 1993, 1153 |
|  | Heterocycles, 1989, 28, 1015<br>Bull. Soc. Chim. Fr., 1987, 1079 |

| R$_2$ | Reference |
|---|---|
|  | |
| 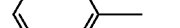 | |
|  | Heterocycles, 1978, 1277–1285 |
|  | Tetrahedron, 1987, 43, 3509–3517 |
|  | EP-355819 |
|  | Tetrahedron Lett., 1988, 29, 6465 |
|  | Heterocycles, 1989, 28, 1015 |
|  | J. Agric. Food Chem., 1977, 25, 965 |
|  | Tetrahedron, 1994, 50 (31), 9457–9470<br>Tetrahedron Lett., 1990, 31, 5153–5156 |

The compounds (I) in which R$_2$ and R$_9$ are linked together and constitute a C$_3$–C$_5$ alkylene which is unsubstituted or substituted with R$_{12}$ are prepared from compounds of formula (XIII) which are known or are prepared by known methods.

In order to obtain optically pure compounds of formula (XIII) or (XIV) it is possible, for example, to use a menthol ester according to the technique described in Tetrahedron Lett., 1988, 29, 6465–6466; a quinine or quinidine salt can also be used, according to Chem. Ber., 1910, 43, 2020, or alternatively the phenylacetamido derivative of the compound of formula (XIV) in racemic form can be used for an enzymatic resolution with a penicillin amylase (Synlett, 1993, 339). Enantioselective syntheses can also be carried out: Tetrahedron, 1994, 50, 9517; Aldrichimica, Acta, 1994, 27(1), 3.

In order to prepare an alpha-hydroxy-beta-amino acid, the method described in Bull. Soc. Chim., France, 1940, 7, 593–603 can be used.

The affinity of the compounds according to the invention for the bradykinin $B_1$ receptors was measured on suspensions of MRC5 cell membranes using a technique similar to that described by K. H. Schneck et al., in Eur. J. Pharmacol., 1994, 266, 227–282. In this test, the affinity of [des-$Arg^9$] bradykinin is between $10^{-6}M$ and $10^{-7}M$, that of [des-$Arg^{10}$]kallidin is $2 \times 10^{-9}M$; and the compounds of the invention have an affinity ranging down to $10^{-10}m$.

The affinity of the compounds according to the invention for the bradykinin $B_2$ receptors was measured on suspensions of MRC5 cell membranes according to a technique similar to that described by D. G. Sawutz et al., in Eur. J. Pharmacol., 1992, 227, 339–315. In that test, the affinity of bradykinin is close to $10^{-9}M$ and that of the compounds of the invention varies around $10^{-6}M$ or $10^{-7}M$.

The toxicity of the compounds according to the invention is compatible with their therapeutic use.

The compounds according to the invention may be useful for the treatment or prevention of many pathologies, in particular inflammation pathologies and persistent or chronic inflammatory diseases (Drug News and Perspectives, 1994, 10(7), 603–611). By way of example, mention may be made of:

neurogenic inflammation, pain (Brit. J. Pharmacol., 1993, 110, 193–198), septic shock, asthma, rheumatoid arthritis, inflammatory diseases of the joints, burns (Pain, 1993, 53, 191–197), wounds, diseases of the respiratory tracts, for example rhinitis of viral or allergic origin, systematic inflammatory response syndrome, oedema (Brit. J. Pharmacol., 1995, 114, 1005–1013), angiogenesis (Brit. J. Pharmacol., 1993, 109, 14–17), type-I infectious diabetes (Abst. 14th Intern. Symp. on Kinins, C49, Denver Colorado, Sep. 10–15, 1995), ventricular hypertrophy associated with diabetes, pulmonary fibrosis and systemic progressive sclerosis, enterocolitis, and more generally any bradykinin-dependent pathology.

The compounds according to the invention are generally administered in dosage units.

The invention also relates to pharmaceutical. compositions comprising, as active principle, one of the enantiomers of the compounds of formula (I), a mixture thereof or salts thereof with a pharmaceutically acceptable acid, as well as to an excipient which is suitable for oral, injectable, topical or transdermal administration. The daily doses depend on the pathology to be treated and on the patient.

The subject of the present invention is also pharmaceutical compositions containing an effective dose of a compound according to the invention or of a pharmaceutically acceptable salt and suitable excipients.

The said excipients are chosen depending on the pharmaceutical forme and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or the possible salts thereof, can be administered in unit forms of administration, as a mixture with standard pharmaceutical supports, to animals and to human beings for the prophylaxis or treatment of the above disorders or diseases. The appropriate unit forms of administration comprise oral forms such as tablets, gelatin capsules, powders, granules or oral solutions or suspensions, sublingual, buccal, intratracheal or intranasal administration forms, subcutaneous, intramuscular or intravenous administration forms and rectal administration forms. For topical application, the compounds according to the invention can be used in creams, ointments, gels cr lotions.

In order to obtain the desired prophylactic or therapeutic effect, the dose of active principle can range between 0.01 and 50) mg per kg of body weight and per day.

Each unit dose can contain from 0.5 to 1000 mg, preferably from 1 to 500 mg, of active ingredients in combination with a pharmaceutical support. This unit dose can be administered 1 to 5 times a day so as to administer a daily dose of from 0.5 to 5000 mg, preferably from 1 to 2500 mg.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose, with a cellulose derivative or with other suitable materials or alternatively they can be treated such that they have sustained or delayed activity and such that they release a predetermined amount of active principle continuously.

A preparation as gelatin capsules can be obtained by mixing the active ingredient with a diluent such as a glycol or a glycol ester and by pouring the mixture obtained into soft or hard gelatin capsules.

A preparation in syrup or elixir form or for administration in the form of drops can contain the active ingredient together with a sweetener, preferably a calorie-free sweetener, methylparaben and propylparaben as antiseptic, as well as a flavouring agent and a suitable dye.

The water-dispersible powders or granules can contain the active ingredient as a mixture with dispersing agents, wetting agents or suspension agents, such as polyvinylpyrrolidone, as well as with sweeteners or flavour enhancers.

For rectal administration, use is made of suppositories which are prepared with binders which melt at the rectal temperature, for example cocoa butter or polyethylene glycols.

Aqueous suspensions, isotonic saline solutions or sterile and injectable solutions which contain pharmacologically compatible dispersing agents and/or wetting agents, for example propylene glycol or butylene glycol, are used for parenteral administration.

Creams, ointments, lotions or gels, for example, can be used for local administration.

Patches in multilaminar or reservoir form in which the active principle may be dissolved can be used for transdermal administration.

The active principle can also be formulated in the form of microcapsules, optionally with one or more supports or additives.

The compositions of the present invention can contain, along with the products of formula (I) above or one of the pharmaceutically acceptable salts, other active principles which can be used in the treatment of the disorders or diseases mentioned above.

The preparations and the examples below illustrate the invention. Except where otherwise mentioned, the compounds are obtained in the form of a mixture of diastereoisomers.

The nuclear magnetic resonance (NMR) spectra are recorded at 200 MHz in deuterated DMSO optionally containing TFA, using tetramethylsilane as reference. The chemical shifts are indicated in ppm.

The mass spectra indicate the value MH$^+$.

PREPARATIONS

Preparation 1.1

1-[2-Amino-3-(4-cyanophenyl)propionyl]pyrrolidine trifluoroacetate.

4.06 g of 2-[N-(Boc)amino]-3-(4-cyanophenyl)propionic acid are mixed with 1.15 ml of pyrrolidine and 7.5 g of BOP in 20 ml of DMF; the mixture is left stirring for 2 hours at RT while maintaining at pH 7 by addition of Et$_3$N. After evaporating to dryness, the residue is chromatographed on silica, eluting with a chloroform/methanol mixture (9/0.5; v/v). After evaporating off the solvents, the solid obtained is treated with 20 ml of TFA in 20 ml of DCM for 30 minutes at RT. The solvents are evaporated off and the residue is taken up in ether and then dried in order to obtain 3.95 g of the expected product.

Preparation 1.2

1-[2-Amino-3-(4-(3,4-dihydroimidazol-2-yl)phenyl) propionyl]pyrrolidine dihydrochloride.

18 g of 1-[2-((N-Boc)amino)-3-(4-cyanophenyl) propionyl]pyrrolidine are dissolved in 90 ml of DCM, 90 ml of TFA are added and the mixture is left stirring for 40 minutes at RT. After evaporating to dryness, the residue is taken up in DCM and then evaporated (twice). The residue is then taken up in 300 ml of HCl-saturated anhydrous ethanol at 0° C. and the mixture is left for 18 hours at +4° C. The medium is evaporated to dryness, taken up in ethanol, evaporated again and then taken up again in DCM and evaporated (twice). 23 g of intermediate imidate are obtained. The product obtained is dissolved in 1 liter of anhydrous ethanol and 4.41 g of ethylenediamine in 50 ml of anhydrous ethanol are added over 30 minutes. After stirring for 48 hours at RT, the medium is concentrated and then acidified to pH=2 by addition of a saturated solution of HCl in methanol. The mixture is drained, evaporated to dryness and then taken up in ether, drained and dried to give 17.4 g of the expected product.

NMR (DMSO+TFA) : 1.50–1.80 :m : 4H; 2.50–3.60 : m : 6H; 4.00 : s : 4H; 4.35 : bs : 1H; 7.50 : d : 2H; 8.15 : d : 2H; 8.60 : bs : 3H; 11.10 : s : 2H.

Preparation 1.3

1-[2-Amino-3-(4-(N$^1$-[3-(dimethylamino)propyl]amidino) phenyl)propionyl]pyrrolidine tris(trifluoroacetate).

A) 1-[2-Amino-3-(4-N$^1$-[3-(dimethylamino)propyl]-amidino)phenyl)propionyl]pyrrolidine trihydrochloride.

809 mg of 1-[2-amino-3-(4-cyanophenyl)propionyl] pyrrolidine trifluoroacetate are dissolved in 50 ml of hydrochloric acid-saturated methanol at 0° C. and the mixture is left overnight in a refrigerator. After evaporating to dryness, the imidate formed is taken up in toluene, the mixture is then evaporated and the residue is dried under vacuum over potassium hydroxide. -The product obtained is dissolved in 75 ml of anhydrous methanol and 570 µl of N-(dimethyl) propane-1,3-diamine dissolved in 15 ml of anhydrous methanol are added slowly. After stirring for 3 hours at RT, the mixture is evaporated to dryness and the residue is then dissolved in 30 ml of methanol, adding 5 ml of 4N HCl in dioxane, and is evaporated to dryness.

B) 1-[2-(N-Boc)amino-3-(4-(N$^1$-[3-(dimethylamino)propyl] amidino)phenyl)propionyl]pyrrolidine dihydrochloride.

The crude product obtained in the above step is dissolved in 10 ml of dioxane and 10 ml of water. Triethylamine is added to reach pH=8.3, followed by 600 mg of (Boc)$_2$O and the mixture is left stirring at RT for 15 hours. The medium is diluted with water, washed twice with ether, acidified to pH=1.5 by addition of 1N HCl and then washed with DCM. This mixture is brought to pH=7 by addition of 1N sodium hydroxide and is evaporated to dryness. The residue is taken up in DCM, the insoluble material is filtered off and the filtrate is then purified by chromatography on silica, eluting with a chloroform/methanol mixture (85/15 to 80/20; v/v). 560 mg of the expected product are obtained.

C) 1-[2-Amino-3-(4-(N$^1$-[3-(dimethylamino)propyl]-amidino)phenyl)propionyl]pyrrolidine tris(trifluoroacetate).

550 mg of the compound of step B are mixed with 15 ml of DCM and 15 ml of TFA and the mixture is left stirring for 45 minutes at RT. After evaporating to dryness, the residue is dissolved in isopropanol, evaporated to dryness again and taken up twice in ether. The product is isolated by decanting and then dried under vacuum in the presence of potassium hydroxide. 380 mg of the expected compound are obtained.

Preparation 1.4

1-[2-Amino-3-(4-cyanophenyl)propionyl]-2,5-dimethyl-2, 5-dihydropyrrole trifluoroacetate.

A) 1-[2-(N-Boc)amino-3-(4-cyanophenyl)propionyl]-2,5-dimethyl-2,5-dihydropyrrole.

2.1 g of 2-[(N-Boc)amino]-3-(4-cyanophenyl)propionic acid are mixed with 0.715 g of 2,5-dimethyl-2,5-dihydropyrrole in 10 ml of DMF, 3.9 g of BOP are added and the pH is adjusted to 7 by addition of Et$_3$N. After stirring for 18 hours at RT, the mixture is evaporated to dryness and is then taken up in EtOAc, washed with NaHCO$_3$ solution, with KHSO$_4$/K$_2$SO$_4$ and with saturated NaCl solution,, The resulting solution is dried over Na$_2$SO$_4$ and then evaporated. The residue is taken up in an ether/hexane mixture and then dried over Na$_2$SO$_4$. 1.4 g of the expected compound are obtained.

NMR : (DMSO+TFA) 1.15–1.25 : m : 6H; 1.30 : s : 9H; 2.9–3.1 : m : 2H; 4.3–4.6 : m : 1H; 4.6–4.75 : m : 1H; 4.9–5.1 : m : 1H; 5.75–5.9 : m : 2H; 7.5 : d : 2H; 7.9 : d : 2H.

B) 1-[2-Amino-3-(4-cyanophenyl)propionyl]-2,5-dimethyl-2,5-dihydropyrrole trifluoroacetate.

The compound of the above step is dissolved in 5 ml of DCM, 5 ml of TFA are added and the mixture is left stirring for 40 minutes at RT. It is evaporated to dryness and the residue is taken up in DCM and evaporated (3 times) and is then taken up in an ether/hexane mixture. The product is drained and then dried over Na$_2$SO$_4$ in order to obtain 1.5 g of the expected product.

Working as in Preparation 1.4, step A above, the compounds described in the table below are prepared:

TABLE 1

BocHN—CH—CO—NR₄R₅
          |
         CH₂
          |
        [C₆H₄]
          |
         CN

| Preparation | —NR₄R₅ | NMR (DMSO + TFA) |
|---|---|---|
| 1.5 | —N(morpholine)O | 1.20: s: 9H; 2.75–2.95: mt: 2H; 3.30–3.60: m: 8H; 4.60: mt: 1H; 7.40: d: 2H; 7.70: d: 2H |
| 1.6 | Me—N-iPr | 0.8–1.2: m: 6H; 1.3: s: 9H; 2.7–3: m: 5H; 4–4.8: m: 2H; 7.5: d: 2H; 7.8: d: 2H |
| 1.7 | Me—N(pyrrolidine)—Me | 0.8–1.1: m: 6H; 1.15: 2: 9H; 1.5–2.1: m: 4H; 2.7–2.9: m: 2H; 3.6–4: m: 2H; 4.1–4.4: m: 1H; 7.4: d: 2H; 7.7: d: 2H |

Preparation 1.8
1-[2-N-Methylamino-3-(4-cyanophenyl)propionyl]-pyrrolidine trifluoroacetate.
A) 2-(N-Boc-N-methyl)amino-3-(4-cyanophenyl)propionic acid.

1.16 g of 2-[N-Boc-amino]-3-(4-cyanophenyl)propionic acid are dissolved in 20 ml of THF and 2 ml of methyl iodide are added at 0° C., followed by portionwise addition of 360 mg of sodium hydride at 80% in oil. The mixture is left stirring overnight at RT. The reaction medium is diluted with EtOAc and then water is added and the pH is brought to 2.5 with 1N HCl. The organic phase is separated out after settling has taken place, then washed with water, with saturated NaCl solution and then dried over $Na_2SO_4$ and evaporated. The residue is taken up in an $Et_2O$/hexane mixture (1/1; v/v). The powder formed is filtered off and dried to give 1.11 g of the expected compound.

NMR (DMSO+TFA) : 1.20 : ds : 9H; 2.55 : ds : 3H; 2.90–3.25 : m : 2H; 4.50–4.80 : m : 1H; 7.30–7.70 : m : 4H.
B) 1-[2-(N-Boc-N-methyl)amino-3-(4-cyanophenyl)propionyl]pyrrolidine.

1.10 g of the compound of the above step, 0.35 ml of pyrrolidine and 1.78 g of BOP-are mixed with stirring in 15 ml of DMF and the pH is adjusted to 6 by addition of DIPEA. After stirring for 2 and a half hours, the mixture is extracted with EtOAc and the organic phase is then washed with 0.25N NaOH, 0.25N HCl, $H_2O$ and then with saturated NaCl solution. The thick wax formed sets to a solid after a few days at +4° C. 1.25 g of the expected compound are obtained.

NMR (DMSO+TFA) : 1.10 : ds : 9H; 1.60–1.85 : m : 4H; 2.60 : ds : 3H; 2.75–3.40 : m : 6H; 4.80–5.10 : m : 1H; 7.25–7.70 m : 4H.
C) 1-[2-N-Methylamino-3-(4-cyanophenyl)propionyl]-pyrrolidine trifluoroacetate.

0.72 g of the compound of the above step is placed in 12 ml of TFA and 12 ml of DCM. After stirring for 40 minutes at RT, the reaction medium is concentrated under vacuum and then evaporated with DCM. 0.75 g of the expected compound is obtained in the form of a thick-wax.

Preparation 1.9
N,N-Diethyl-[2-amino-3-(4-(3,4-dihydroimidazol-2-yl)phenyl)]propionamide dihydrochloride.

N,N-Diethyl-[2-(N-Boc)amino-3-(4-cyanophenyl)]-propionamide is prepared by working according to the procedure described in Preparation 1.4, step A. The expected product is then obtained according to the procedure described in Preparation 1.2.

Preparation 1.10
Ethyl ester of 2-(N-Boc)amino-3-(4-cyanophenyl)propionic acid.

26 g of $Boc_2O$ dissolved in 100 ml of DCM are gradually added to a solution of 25.5 g of the ethyl ester hydrochloride of 2-amino-3-(4-cyanophenyl)propionic acid and 13.9 ml of $Et_3N$ in 400 ml of DCM. After stirring for 6 hours at RT, the reaction medium is washed with $KHSO_4$/$K_2SO_4$ solution, with saturated $NaHCO_3$ solution and with saturated NaCl solution. After drying over $Na_2SO_4$ and evaporation of the DCM, the residue is triturated from heptane to give 29 g of white powder.

Preparation 1.11
Ethyl ester of (R)-2-(N-Boc)amino-3-(4-cyanophenyl)propionic acid : compound B and (S)-2-(N-Boc)amino-3-(4-cyanophenyl)propionic acid : compound A.

A mixture of 24 g of the product obtained above and 8.4 g of $NaHCO_3$ in 900 ml of EtOAc and 500 ml of $H_2O$ is treated with 2 ml of Alcalase® for 24 hours at RT. The 2 phases are separated out after settling has taken place; the EtOAc phase is rewashed with 100 ml of 10% $NaHCO_3$ solution which is added to the first aqueous phase and the aqueous phase is rewashed with 100 ml of EtOAc added to the firs: EtOAc phase. The EtOAc phase thus obtained is dried over $Na_2SO_4$ and then evaporated to dryness; 12.45 g of compound B are obtained.
$\alpha_D^{25}$=+8.8° (c=1; MeOH)

The aqueous phase is taken up in EtOAc and brought to pH=2.5 with 6N HCl. EtOAc is separated out after settling has taken place and rewashed with $KHSO_4$/$K_2SO_4$ solution, with saturated NaCl solution, dried over $Na_2SO_4$ and evaporated to dryness, and 10.1 g of compound A are obtained.
$\alpha_D^{25}$=+8.8° (c=1; MeOH)

Preparation 1.12
1-[2-Amino-3-(4-cyanophenyl)propionyl]pyrrolidine trifluoroacetate, (S) isomer.
A) 2,5-Dioxo-1-pyrrolidinyl ester of 2-(N-Boc)amino-3-(4-cyanophenyl)propionic acid, (S) isomer.

9.85 g of 2-(N-Boc)amino-3-(4-cyanophenyl)propionic acid, (S) isomer, and 4.14 g of NSuOH are dissolved in 100 ml of dioxane and 8.5 g of DCC dissolved in 30 ml of dioxane are added slowly at RT, after which the mixture is stirred for 8 hours at RT. The DCU is filtered off and washed with acetone. After evaporating the filtrate to dryness, the residue is dissolved in acetone and then left overnight at RT. The remaining DCU which has precipitated is removed and the filtrate is then evaporated to dryness, triturated from $Et_2O$ and then drained, washed with $Et_2O$ and dried. 11.5 g of the expected compound are obtained,
$\alpha_D^{25}$=−29.7° (c=1, MeOH)
B) 1-[2-(N-Boc)amino-3-(4-cyanophenyl)propionyl]-pyrrolidine, (S) isomer.

11 g of the compound of the above step are placed in 150 ml of acetonitrile and 20 ml of DMF and 2.5 ml of pyrrolidine in 30 ml of acetonitrile are added over 10 minutes. The mixture is left stirring for 2 hours at RT and is then left overnight at RT. It is evaporated to dryness, the residue is taken up in EtOAc and a $KHSO_4/K_2SO_4$ buffer is then added. This mixture is extracted with EtOAc, then washed with saturated $NaHCO_3$ solution and then with saturated NaCl solution; it is dried over $Na_2SO_4$ and then evaporated to dryness. The residue is triturated from $Et_2O$, drained, washed with $Et_2O$ and dried. 6.95 g of the expected compound are obtained.

$\alpha_D^{25}$=+26° (c=1, MeOH)

C) 1-[2-Amino-3-(4-cyanophenyl)propionyl]pyrrolidine trifluoroacetate, (S) isomer.

6.75 g of the compound of the above step are dissolved in 50 ml of DCM and the insoluble material is filtered off. 50 ml of TFA are added and the mixture is left stirring for 45 minutes. It is evaporated to dryness, the residue is redissolved in isopropanol, this solution is again evaporated to dryness and the residue is then triturated from $Et_2O$, drained, washed with $Et_2O$ and dried over $Na_2SO_4$. 6.13 g of the expected compound are obtained, m.p.=193–196° C.

$\alpha_D^{25}$=+51° (c=1, MeOH)

Preparation 1.13

1-[2-Amino-3-(4-cyanophenyl)propionyl]pyrrolidine trifluoroacetate, (R) isomer.

A) (R)-2-(N-Boc)amino-3-(4-cyanophenyl)propionic acid.

43 ml of 1N NaOH solution are added to 12.18 g of compound B of Preparation, 1.11 dissolved in 180 ml of MeOH and the mixture is stirred for 1 hour at RT. 43 ml of 1N HCl solution are then added and 150 ml of methanol are evaporated off, after which the mixture is taken up in EtOAc and is washed with water and then with saturated NaCl solution. 11 g of the expected compound are obtained after crystallization from an $Et_2O$/heptane mixture.

$\alpha_D^{25}$=−9.5° (c=1; MeOH)

B) Ester of 2,5-dioxo-1-pyrrolidinyl (R)-2-(N-Boc)amino-3-(4-cyanophenyl)propionic acid.

4.2 g of NSuOH are added to 10 g of the acid obtained above dissolved in 10 ml of dioxane, followed by addition, over 20 minutes, of 8.62 g of DCC dissolved in 30 ml of dioxane. After stirring overnight at RT, the DCU formed is filtered off and washed with dioxane. The filtrate is evaporated to dryness and the residue is triturated from ether to give a solid which is filtered off and dried. 12.09 g of the expected compound are obtained.

$\alpha_D^{25}$=+27.1° (c=1; MeOH)

C) 1-[2-(N-Boc)amino-3-(4-cyanophenyl)propionyl]-pyrrolidine, (R) isomer.

2.6 ml of pyrrolidine dissolved in 20 ml of acetonitrile are added to 11.6 g of the compound obtained in the above step dissolved in 150 ml of acetonitrile plus 20 ml of DMF. After stirring overnight at RT, a small amount of insoluble material is removed and the filtrate is concentrated under vacuum. The residue is taken up in EtOAc and washed with $KHSO_4/K_2SO_4$ solution, with saturated $NaHCO_3$ solution and with saturated NaCl solution; after drying over $Na_2SO_4$, the EtOAc is evaporated under vacuum, the residue is triturated from ether and 9.3 g of the expected compound are obtained in the form of a white solid.

$\alpha_D^{25}$=−29.2° (c=1; MeOH)

D) 1-[2-Amino-3-(4-cyanophenyl)propionyl]pyrrolidine trifluoroacetate, (R) isomer.

8.7 g of the product obtained in the above step are stirred for 35 minutes in a mixture of 50 ml of DCM and 50 ml of TFA. After evaporating to dryness, the residue is taken up in isopropanol and re-evaporated to dryness, and 8.67 g of the expected compound are obtained in solid form.

$\alpha_D^{25}$=−46° (c=1; MeOH)

Preparation 1.14

1-[2-Amino-2-methyl-3-(4-cyanophenyl)propionyl]-pyrrolidine trifluoroacetate.

A)

A mixture of 7 g of (D,L) alanine methyl ester, 14 ml of $Et_3N$, 4.2 g of $MgSO_4.3H_2O$ and 5.1 ml of benzaldehyde in 100 ml of dichloromethane is stirred for 18 hours at RT. The insoluble material is filtered off, the filtrate is concentrated under vacuum and the residue is taken up in an ether/water mixture; the ether is separated out after settling of the phases has taken place, rewashed with water and then with saturated NaCl solution, dried over $Na_2SO_4$ and evaporated. 8.3 g of the expected compound are obtained in the form of an oil.

B)

13.2 ml of lithium bis(trimethylsilyl)amide (IM in THF) are added, at −70° C. over 20 minutes, to 2.29 g of the product of the above step dissolved in 60 ml of THF. After 30 minutes, 2.35 g of 4-bromomethylbenzonitrile dissolved in 15 ml of THF are added over 15 minutes and the temperature is then allowed to rise slowly. After 3 and a half hours, the reaction medium is taken up in EtOAc and washed with water and with saturated NaCl solution. After drying and evaporating the EtOAc, 3.6 g of the expected compound are obtained in the form of an oil.

C)

The compound of the above step is taken up in 60 ml of ether plus 60 ml of 1N HCl and is stirred for 18 hours at RT. The aqueous phase is separated out after settling of the phases has taken place, placed in contact with EtOAc and brought to pH=10 with 10N NaOH; the EtOAc is separated out after settling of the phases has taken place, rewashed with $H_2O$ and with saturated NaCl solution, dried and evaporated. 2.20 g of the expected compound are obtained in the form of an oil.

D)

2.42 g of $Boc_2O$ dissolved in 10 ml of dioxane are added, at 10° C. over 10 minutes, to 2.18 g of the compound of the above step dissolved in 10 ml of dioxane; the mixture is then stirred overnight at RT and then for 3 hours at 40° C. The reaction medium is taken up in EtOAc, washed with water and then with saturated NaCl solution, dried and then evaporated to give an oil which is used directly in the following step.

E)

The product of the above step is dissolved in 10 ml of methanol, 2.4 ml of 8.36N KOH solution are added and the mixture is stirred overnight; a further 2.4 ml of the KOH solution are added and the mixture is refluxed for 1 hour. The reaction medium is cooled and taken up in a water/ether mixture; the aqueous phase is separated out after settling of the phases has taken place, taken up in EtOAc and brought to pH=2 with 1N HCl. The EtOAc is separated out after settling of the phases has taken place, rewashed with $H_2O$ and with saturated NaCl solution, dried over $Na_2SO_4$ and then evaporated. 0.99 g of the expected compound is obtained after chromatography on silica, eluting with chloroform/MeOH/AcOH (94/6/0.2; v/v/v).

F)

0.30 ml of pyrrolidine, 1.55 g of BOP and DIPEA to obtain a pH of 6–7 are added to 0.98 g of the compound of the above step in 10 ml of DMF. After stirring for 2 and a half hours, the reaction medium is taken up in EtOAc and washed with $H_2O$, 0.2N NaOH, 0.2N HCl, $H_2O$ and saturated NaCl solution. After drying and evaporating, 1.13 g of the expected compound are obtained, m.p.=84–87° C.

NMR (DMSO+TFA) : 1.20 : s : 3H; 1.45 : s : 9H; 1.60–1.90 : m : 4H; 3.00–3.50 : m : 6H; 7.30 : d : 2H; 7.80 : d : 2H.

G)
1.12 g of the compound of the above step are stirred for 1 hour in a mixture of 10 ml of DCM and 12 ml of TFA. After evaporating and drying, 1.15 g of the expected compound are obtained in the form of a solid.

Preparation 2.1
3-Amino-3-(2-naphthyl)propionic acid hydrochloride.

The method described in J. Am. Chem. Soc., 1936, 58, 299 is used. 15.5 g of 2-formylnaphthalene, 10.4 g of malonic acid and 15.4 g of ammonium acetate in 150 ml of ethanol are mixed together and refluxed for 6 hours. After cooling to RT, the product is drained, washed with EtOH and dried. The product obtained is dissolved in a sufficient amount of 2N HCl and the insoluble material is then filtered off. The acidic solution is concentrated by evaporating under vacuum and the solid thus formed is recrystallized from 20 ml of an AcOH/$H_2O$ mixture (1/1; v/v). 3.8 g of the expected product are obtained.

The compounds of Table 2 below are prepared according to the procedure described above.

TABLE 2

$H_2N-CH-CH_2-COOH, HCl$
         |
         $R_2$

| Preparations | $R_2$ |
|---|---|
| 2.2 | —C₆H₄—Cl (4-chlorophenyl) |
| 2.3 | —C₆H₄—OBn (4-benzyloxyphenyl) |
| 2.4 | —C₆H₄—OBn (3-benzyloxyphenyl) |
| 2.5 | —C₆H₃—Cl,Cl (3,4-dichlorophenyl) |

Preparation 2.6
3-(N-Boc)amino-3-(3,4-dichlorophenyl)propionic acid.

Starting with the compound of Preparation 2.5, the N-protected beta-amino acid is prepared in the following way.

10 g of 3-amino-3-(3,4-dichlorophenyl)propionic acid are dissolved in 100 ml of water and 9 ml of triethylamine are added, followed by gradual addition of 9.3 g of $(Boc)_2O$ in 100 ml of dioxane. After stirring overnight at RT, the medium is concentrated and the residue is then taken up in water, adjusting the pH to 9 by addition of 1N sodium hydroxide. This mixture is washed twice with ether, the aqueous phase is taken up and acidified to pH=3 by addition of 1N HCl and is extracted with EtOAc and concentrated in order to obtain 3.9 g of the expected compound, m.p.=128° C.

NMR (DMSO) 1.25 ppm : s : 9H; 2.50–2.65 ppm : mt : 2H; 4.75 ppm : q : 1H; 7.25 ppm : d : 1H; 7.20–7.40 ppm : m : 3H Preparation 2.7
3-Amino-3-(3-isopropyloxyphenyl)propionic acid hydrochloride A) (3-Isopropyloxy)benzaldehyde.

3.4 g of $K_2CO_3$ and 1.5 g of benzyltriethylammonium chloride are added to 12.2 g of 3-hydroxybenzaldehyde in 100 ml of DMSO, followed by addition, over 30 minutes, of 10 ml of isopropyl iodide dissolved in 20 ml of DMSO, and the mixture is left stirring overnight at RT. The mixture is poured onto 400 ml of water and is then extracted with EtOAc, washed with saturated NaCl solution and then dried over $Na_2SO_4$ and evaporated to dryness. The oil obtained (14.4 g) is used without further purification in the following step.

B) 3-Amino-3-(3-isopropyloxyphenyl)propionic acid hydrochloride.

A mixture containing 14 g of the oil obtained in the above step, 150 ml of methoxyethanol, 8.95 g of malonic acid and 13.2 g of ammonium acetate is heated overnight at 80° C. After cooling, the mixture is evaporated to dryness and the oil formed is then dissolved in ethanol and 50 ml of 2N HCl. Fractional evaporation is carried out in order to obtain the expected compound, which is drained and then washed with EtOAc. 4.56 g are obtained.

NMR (DMSO) : 1.25 : d : 6H; 4.65 : septet : 1H; 7.20–7.55 : mt : 4H; 9.95 : s : 1H.

The compounds described in the table below are prepared according to the procedure described in the above preparation.

TABLE 3

$H_2N-CH-CH_2-COOH, HCl$
         |
         $R_2$

| Preparation | $R_2$ | NMR |
|---|---|---|
| 2.8 | 3-methoxyphenyl (OMe) | 2.85–3.15: mt: 2H; 3.85: s: 3H; 4.60: t: 1H; 6.95–7.45: mt: 4H |
| 2.9 | 4-methoxyphenyl (OMe) | (DMSO + TFA) 2.50–3.00: mt: 2H; 3.70: s: 3H; 4.50: t: 1H; 6.90: d: 2H; 7.40: d: 2H |
| 2.10 | 3-chlorophenyl (Cl) | (DMSO + TFA) 2.80–3.10: mt: 2H; 4.60: t: 1H; 7.30–7.60: m: 4H |
| 2.11 | 3-trifluoromethylphenyl ($CF_3$) | (DMSO + TFA) 2.90–3.20: mt: 2H; 4.75: t: 1H; 7.00–8.05: mt: 4H |
| 2.12 | 1-methylnaphthyl | (DMSO + TFA) 3.00–3.20: mt: 2H; 5.40–5.60: mt: 1H; 7.50–8.30: m: 7H |

TABLE 3-continued $$H_2N-\underset{\underset{R_2}{|}}{CH}-CH_2-COOH, HCl$$

| Preparation | R₂ | NMR |
|---|---|---|
| 2.13 | (3-fluorophenyl group) | (DMSO + TFA) 2.75–3.10: mt: 2H; 5.60: t: 1H; 7.00–7.45: m: 4H |
| 2.14 | (cyclohexyl group) | (DMSO + TFA) 0.90–1.75: m: 11H; 2.40–2.70: mt: 2H; 3.15–3.30: m: 1H |
| 2.15 | (3-methylphenyl group, Me) | (DMSO + TFA) 2.25: s: 3H; 2.80–3.05: mt: 2H; 4.55: t: 1H; 7.10–7.30: m: 4H |

Preparation 2.16
3-(N-Boc)amino-3-biphenyl-4-ylpropionic acid.
A) 3-Amino-3-biphenyl-4-ylpropionic acid hydrochloride.

18.2 g of 4-phenylbenzaldehyde, 10.4 g of malonic acid and 15.4 g of ammonium acetate in 150 ml of methoxyethanol are mixed together. After heating overnight at 80° C., the mixture is cooled and the product formed is then washed with ethanol, with ether and then dried. After washing again with water, the product is recrystallized from a methanol/water mixture with a small amount of HCl. A mixture of the expected product and of the methyl ester hydrochloride of 3-amino-3-biphenyl-4-ylpropionic acid is obtained, which is used without further purification in the following step.
B) 3-(N-Boc).Amino-3-biphenyl-4-ylpropionic acid.

The product of the above step is placed in 200 ml of dioxane, 55 ml of 2N NaOH are added and the mixture is left stirring at RT for 1 hour 40 minutes. 13 g of Boc₂O are added and stirring is continued overnight. The insoluble material is filtered off, dilution is carried out with 200 ml of water, the mixture is washed with Et₂O and then acidified to pH=2.5 by addition of 2N HCl in the presence of 100 ml of EtOAc. This mixture is extracted with EtOAc, washed with KHSO₄/K₂SO₄, with saturated NaCl solution and then dried over Na₂SO₄ and evaporated to dryness in order to obtain 11.03 g of the expected compound.

NMR (DMSO) : 1.40 : s : 9H; 2.60–2.85 : mt : 2H; 5.00 : dq : 1H; 7.35–7.80 : mt : 10H; 12.30 : bs : 1H.

Preparation 2.17
2,5-Dioxo-1-pyrrolidinyl 3-(N-Boc)amino-3-biphenyl-4-ylpropionate.

3.41 g of the acid described in the above preparation are placed in 50 ml of dioxane and treated with 1.26 g of hydroxysuccinimide in the presence of 2.5 g of DCC. The mixture is left stirring overnight at RT and is then drained and washed with acetone. The filtrate is evaporated to dryness and then taken up in isopropanol. The solid is drained, washed with ether and dried to give 3.46 g of the expected compound, m.p.=161° C.

NMR (DMSO) : 1.35 : s : 9H; 2.80 : s : 4H; 3.00–3.20 : mt : 2H; 5.00 : dq : 1H; 7.30–7.75 : mt : 10H.

Preparation 2.18
(1,2,3,4-Tetrahydro-1-isoquinolyl)acetic acid.

This compound is prepared according to J. Org. Chem., 1987, 52, 616–622.
A) 3,4-Dihydroisoquinoline.

9.4 ml of 1,2,3,4-tetrahydroisoquinoline are dissolved in 200 ml of DCM and 14.7 g of NBS are gradually added. The mixture is left stirring at RT, cooling slightly in order to maintain a temperature of less than 40° C. for 30 minutes, after which 50 ml of 10N NaOH are added and the mixture is left stirring for 1 hour at RT. The organic phase is separated out after settling of the phases has taken place and is washed with 100 ml of water and then twice with 100 ml of 4N HCl. The aqueous phases are washed with DCM and then brought to pH=9 by addition of concentrated NH₄OH. This mixture is extracted with DCM, dried over Na₂SO₄ and evaporated to dryness. The oil obtained is distilled off. 7.16 g of the expected compound are obtained, b.p.=50–54° C. at 0.05 mbar.
B) (1,2,3,4-Tetrahydro-1-isoquinolyl)acetic acid.

A mixture containing 6.62 g of 3,4-dihydroisoquinoline and 5.13 of malonic acid is triturated in an oil bath at 120° C. The mixture thickens and becomes entirely solid; it is worked into a powder with a spatula. The total duration of heating is about 40 minutes. The mixture is cooled to about 60° C. and treated with 120 ml of MeOH and 20 ml of water, which dissolves the medium. A first crop is obtained under cold conditions and a second crop is then obtained by evaporating the filtrate and crystallizing the residue from acetone.

NMR (DMSO+TFA) : 2.90–3.15 : mt : 4H; 3.30–3.60 : mt : 2H; 4.90 : t : 1H; 7.20–7.40 : m : 4H.

Preparation 2.19
3-Amino-3-phenylpropionic acid trifluoroacetate, (R) isomer.
A) (2-Isopropyl-5-methyl)cyclohexyl 3-(N-Boc)amino-3-phenylpropionate, (R) isomer.

This reaction is carried out according to Tetrahedron Letters, 1988, 29, 6465–6466. A solution containing 11.1 g of 3-(N-Boc)amino-3-phenylpropionic acid, 7.5 g of L(−)-menthol and 2.1 g of DMAP in 400 ml of DCM is prepared; after stirring, 11.2 g of DCC dissolved in 50 ml of DCM are gradually introduced. After stirring overnight at RT, the mixture is filtered, the DCU is washed with acetone and the filtrate is evaporated to dryness. The residue is taken up in 150 ml of heptane at 80–90° C.; the insoluble material is filtered off and the solution is left at RT for 4 hours. The solid is drained, washed with heptane and dried at 40° C. until the menthol odour has disappeared. 4.25 g of the expected compound are obtained.

$\alpha_D^{25}$=−16.5° (c=1; MeOH)
B) 3-(N-Boc)amino-3-phenylpropionic acid, (R) isomer.

A mixture-containing 4.22 g of the compound of the above step and 15.7 ml of 1N NaOH in 100 ml of methanol is refluxed for 4 hours. The reaction medium is cooled, treated with 15.7 ml of 1N HCl and then evaporated to dryness and taken up in heptane. After leaving for a few hours at RT, the product crystallizes, it is drained, washed with heptane and then dried at 40° C. until the menthol odour has disappeared. 2.65 g of the expected compound are obtained.

$\alpha_D^{25}$=+42.1° (c=1; MeOH)
C) 3-Amino-3-phenylpropionic acid trifluoroacetate, (R) isomer.

2.3 g of the compound obtained in the above step are dissolved in 15 ml of DCM and 15 ml of TFA are added. After stirring for 35 minutes at RT, the solution is evaporated to dryness. The product is taken up in isopropanol, evaporated and then crystallized from Et$_2$O. The product is drained, washed with Et$_2$O and dried in order to obtain 2.16 g of the expected compound.

Preparation 2.20

3-Amino-4-phenylbutyric acid hydrochloride, (S) isomer.

A) Methyl 2-(N-Boc)amino-3-phenylpropionate, (S) isomer.

10.8 g of methyl (L)-2-amino-3-phenylpropionate hydrochloride in 150 ml of DCM are mixed with 7 ml of Et$_3$N and 13 g of (Boc)$_2$O in 50 ml of DCM are gradually added. After stirring for 5 hours at RT, the reaction medium is washed with KHSO$_4$/K$_2$SO$_4$ and then with saturated NaCl solution. The resulting solution is dried in order to remove the excess (Boc)$_2$O and is then dissolved in DCM and 1.5 ml of N,N-dimethylpropanediamine are added. After stirring for 4 hours, the mixture is washed with KHSO$_4$/K$_2$SO$_4$ and then with saturated NaCl solution. This solution is dried over Na$_2$SO$_4$ and then evaporated to dryness in order to obtain 11.9 g of the expected compound.

B) 2-(N-Boc)amino-3-phenylpropanol, (S) isomer.

This step and the following 2 are carried out according to Tetrahedron, 1994, 50(31), 9457. 10 g of the compound of the above step are dissolved in 120 ml of THF and the solution is cooled on an ice bath; 3.17 g of lithium chloride are added, followed by 2.8 g of sodium borohydride and, gradually, 170 ml of EtOH. After stirring overnight at RT, 70 ml of 1M KHSO$_4$ are added slowly and the mixture is concentrated almost to dryness. The concentrate is diluted in chloroform and 1M KHSO$_4$ and is then extracted with chloroform. The extracts are washed with saturated NaCl solution, dried over Na$_2$SO$_4$ and evaporated to dryness in order to obtain 8.65 g of the expected compound.

C) 2-Amino-3-phenylpropyl methanesulphonate, (S) isomer.

7.5 g of the compound of the above step are dissolved in 40 ml of pyridine and the mixture is cooled in an ice bath; 3.3 ml of mesyl chloride are added over 15 min and the mixture is then left stirring for 2 hours at RT. 15 ml of water are added over 5 minutes and the medium is then diluted with ether and washed with 1M KHSO$_4$ (twice), with water and then with saturated NaCl solution; the resulting solution is dried over Na$_2$SO$_4$ and then evaporated to dryness in order to obtain 9.2 g of the expected compound.

$\alpha_D^{25}$=−24.3° (c1; MeOH)

D) 3-(N-Boc)amino-4-phenylbutyronitrile, (S) isomer.

A solution containing 9.05 g of the compound of the above step with 7.3 g of 18-crown-6 crown ether and 120 ml of DMSO is prepared and 9 g of potassium cyanide are added with stirring in an ice bath. After heating at 50° C. for 5 hours, the mixture is cooled and 600 ml of Et$_2$O are then added. This mixture is washed with water (3 times) and then with saturated NaCl solution; the resulting solution is dried over Na$_2$SO$_4$ and then evaporated to dryness in order to obtain 6.58 g of the expected compound.

E) 3-Amino-4-phenylbutyric acid hydrochloride, (S) isomer.

This step is carried out according to Tetrahedron Letters, 1990, 31, 5153. 4.1 g of the compound of the above step are suspended in 50 ml of 6N HCl and the mixture is refluxed for 5 hours. It is concentrated in order to obtain a first crop of the pure expected compound. On evaporating to dryness, a second crop of 1.4 g of the expected compound contaminated with NH$_4$Cl is obtained. A sample is treated with (Boc)$_2$O and its optical rotation is measured.

$\alpha_D^{25}$=−17° (c=1; MeOH)

literature $\alpha_D^{25}$=−16° (c=1; MeOH)

Preparation 2.21

3-Amino-3-phenylpropionic acid trifluoroacetate, (S) isomer.

The preparation is identical to the one described in 2.19, but using D(+)-menthol.

Preparation 3.1

3-Phenyl-3-(2,4,6-trichlorobenzenesulphonamido-) propionic acid.

1.15 g of 3-amino-3-phenylpropionic acid are dissolved in 25 ml of dioxane and 7 ml of 1N sodium hydroxide and 1.95 g of 2,4,6-trichlorobenzenesulphonyl chloride in 5 ml of dioxane are gradually added, while maintaining the pH at 10.5–11 by addition of 1N sodium hydroxide. After stirring for 2 hours at RT, the mixture is diluted with 100 ml of water, extracted twice with EtOAc and acidified to pH=2 by addition of 6N HCl. The solid formed is drained, washed with water and dried at 40° C. 2.09 g of the expected product are obtained, m.p.=218–219° C.

NMR (DMSO+TFA) : 2.60–2.95 : mt : 2H; 4.75 : q : 1H; 7.10–7.30 : m : 5H; 7.60 : s : 2H; 8.85 : d : 1H.

Preparation 3.2

3-(Naphth-2-ylsulphonamido)-3-phenylpropionic acid.

4.13 g of 3-amino-3-phenylpropionic acid are dissolved in 100 ml of dioxane and 25 ml of 1N sodium hydroxide and 5.6 g of 2-naphthalenesulphonyl chloride are added portionwise, while maintaining the pH at 10.5–11 by addition of 1N sodium hydroxide. After stirring for 2 hours at RT, the mixture is diluted with 400 ml of water and 2N HCl is added in order to obtain pH=2. This mixture is extracted with EtOAc and the extracts are washed with a KHSO$_4$/K$_2$SO$_4$ buffer, dried over Na$_2$SO$_4$ and evaporated to dryness. The residue is triturated from heptane and the product is isolated by decanting and is then dried under vacuum. 7.33 g of the expected product are obtained, m.p.=126–129° C.

NMR (DMSO+TFA) : 2.55–2.70 : mt : 2H; 4.70 : t : 1H; 6.85–8.15 : m : 12H.

Preparation 3.3

2-Hydroxy-3-(naphth-2-ylsulphonamido)-3-phenylpropionic acid.

This compound is prepared according to Bull. Soc. Chim., France, 1940, 593–603.

Working according to the procedures described in Preparations 3.1 and 3.2, starting with the compounds obtained in Preparation 2 and 2-naphthalenesulphonyl chloride, the acids described in Table 4 below are obtained.

TABLE 4

Naphthyl—SO$_2$—NH—CH(R$_2$)—CH$_2$—COOH

| Preparations | R$_2$ | NMR | m.p. ° C. |
|---|---|---|---|
| 3.4 | naphthyl | (DMSO) 2.80: d: 2H; 4.90: q: 1H; 7.15–8.20: m: 14H; 8.60: d: 1H | 145–150 |
| 3.5 | 4-chlorophenyl | (DMSO + TFA) 2.00–2.20: mt: 2H; 4.45: t: 1H; 7.10–8.25: m: 11H | 223–228 |

TABLE 4-continued

![structure: naphthalene-SO2—NH—CH(R2)—CH2—COOH]

| Preparations | R2 | NMR | m.p. ° C. |
|---|---|---|---|
| 3.6 | —C6H4—OBn (para) | (DMSO) 2.50–2.75: mt: 2H; 4.60–4.80: mt: 3H 6.65–8.15: m: 16H 8.40: bs: 1H | 253–255 |
| 3.7 | —C6H4—OBn (meta) | RMN(DMSO) 2.40–2.65: mt: 2H 4.65: s: 2H; 4.75: dq: 1H; 6.40–8.05: m: 16H 8.40: bs: 1H | |

The acids described above are converted by the action of N-hydroxysuccinimide in the presence of DCC in DMF. The compounds obtained are described in Table 5 below.

TABLE 5

![structure: naphthalene-SO2—NH—CH(R2)—CH2—COONSu]

| Preparations | R2 | NMR(DMSO) | m.p.(° C.) |
|---|---|---|---|
| 3.8 | naphthyl | s.75: s: 4H; 3.20: mt: 2H; 4.90: dq: 1H; 7.20–8.10: m: 14H; 8.70: d: 1H | 165 |
| 3.9 | —C6H4—Cl | | 192 |
| 3.10 | —C6H4—OBn (para) | | 187 |
| 3.11 | —C6H4—OBn (meta) | 2.80: s: 4H; 3.15: mt: 2H; 4.65: s: 2H; 4.75: dq: 1H; 6.45–7.95: mt: 4H; 7.25–8.20: mt: 12H; 8.60: d: 1H | 110 |

Preparation 3.12
3-(2-Hydroxyphenyl)-3-(naphth-2-ylsulphonamido) propionic acid.

1.1 g of 3-amino-3-(2-hydroxyphenyl)propionic acid hydrochloride, prepared according to J. Agric. Food Chem., 1977, 25, 965, are dissolved in 25 ml of dioxane and 10 ml of 1N NaOH are added; 1.12 g of 2-naphthalenesulphonyl chloride are gradually added while maintaining the pH at 11.5–12 by addition of 1N NaOH. After stirring for 2 hours at RT, the reaction medium is diluted in water, washed with EtOAc (twice) and then acidified to pH=1.5–2 by addition of 6N HCl. The white precipitate formed is drained, washed with water and dried in order to obtain 0.82 g of the expected product, m.p.=190–200° C.

NMR (DMSO) 2.50–3.20 : mt : 2H; 4.80 : mt : 1H; 6.95–8.30 : m : 11H; 8.75 : s : 1H.

Preparation 3.13

3-Phenyl-3-(quinol-2-ylsulphonamido)propionic acid.

A) 2-Quinolinesulphonyl chloride.

3.2 g of 2-mercaptoquinoline are suspended in 40 ml of water containing 0.156 g of iron trichloride. The mixture is cooled in an ice bath and chlorine is then bubbled through for 1 hour at 4° C. The mixture is evaporated and the residue is then taken up in the minimum amount of water and the product is drained and dried in order to obtain 2.30 g of the expected compound in dry form.

B) 3-Phenyl-3-(quinol-2-ylsulphonamido)propionic acid.

1.65 g of the compound prepared in the above step are dissolved in 40 ml of dioxane and 20 ml of 1N NaOH are added, along with portionwise addition of 2.27 g of 3-amino-3-phenylpropionic acid, while maintaining the pH at 10. The mixture is left stirring for 18 hours at RT and is then evaporated to dryness. The residue is taken up in a DCM/$H_2O$ mixture, the phases are separated after settling has taken place and the organic phase is extracted with water. Acidification to pH=1 is carried out by addition of HCl and the product is then drained and dried over $MgSO_4$ in order to obtain 1.9 g of the expected compound.

NMR (DMSO+TFA) : 2.4–2.9 : m : 2H; 4.9 : mt : 1H; 6.9–7.1 : mt : 3H; 7.2 : d : 2H; 7.7–8.1 : m : 5H; 8.4 : d : 1H; 8.8 d : 1H.

Preparation 3.14

3-Phenyl-3-(quinol-8-ylsulphonamido)propionic acid.

This compound is prepared according to the procedure described above, starting with 8-quinolinesulphonyl chloride.

Preparation 3.15

3-(3-Isopropyloxyphenyl)-3-(naphth-2-ylsulphonamido) propionic acid.

1.3 g of the compound of Preparation 2.7 are suspended in 20 ml of dioxane and treated with 2N NaOH and then with 1N NaOH in order to bring the mixture to pH=12. 1.13 g of 2-naphthalenesulphonyl chloride are added portionwise, while maintaining the pH at 10.5–11.5 by addition of 1N NaOH. The mixture is left stirring for 2 hours at RT and is then diluted with water, washed with EtOAc and then brought to pH=2 by addition of 2N HCl. This mixture is extracted with EtOAc and then washed with a $KHSO_4$/$K_2SO_4$ buffer and with saturated NaCl solution. The resulting solution is dried over $Na_2SO_4$ and concentrated in order to obtain 900 mg of the expected compound, m.p.=126° C.

NMR (DMSO) : 0.95 : d : 6H; 2.40–2.55 : mt : 2H; 4.10 : tq : 1H; 4.60 dq :H; 6.20–8.05 : mt : 11H; 8.30 : d : 1H; 12.20 : bs : 1H.

Following the procedure described in the above preparation, and using the compounds of Preparations 2.8 to 2.15 as starting materials, the compounds described in Table 6 below are prepared.

TABLE 6

Structure: Naphthalene-SO₂NH—CH(R₂)—CH₂—COOH

| Preparation | R₂ | NMR | m.p. ° C. |
|---|---|---|---|
| 3.16 | 3-methoxyphenyl (OMe) | (DMSO) 2.35–2.55: mt: 2H; 3.35: s: 3H; 4.60: dq: 1H; 6.20–6.85: mt: 4H; 7.40–8.0: mt: 7H; 8.30: d: 1H; 12.20: bs: 1H | 154 |
| 3.17 | 4-methoxyphenyl (OMe) | (DMSO) 2.35–2.60: mt: 2H; 3.35: s: 3H; 4.55: dq: 1H; 6.35: d: 2H; 6.90: d: 2H; 7.40–7.95: mt: 7H; 8.25: d: 1H; 12.20: bs: 1H | 139 |
| 3.18 | 3-chlorophenyl (Cl) | (DMSO) 2.40–2.70: mt: 2H; 4.60: mt: 1H; 6.70–7.10: m: 4H; 7.40–8.20: m: 7H; 8.45: bd: 1H; 12.30: bs: 1H | 133 |
| 3.19 | 3-trifluoromethylphenyl (CF₃) | (DMSO) 2.40–2.70: mt: 2H; 4.70: dq: 1H; 7.00–8.00: m: 11H; 8.45: d: 1H; 12.20: bs: 1H | 164 |
| 3.20 | 1-methylnaphthyl | (DMSO) 2.80: bd: 2H; 5.60: mt: 1H; 7.10–8.10: m: 14H; 8.65: d: 1H; 12.30: bs: 1H | 189 |
| 3.21 | 3-fluorophenyl (F) | (DMSO) 2.45–2.65: mt: 2H; 4.70: dq: 1H; 6.60–7.05: m: 4H; 7.50–8.15: m: 7H; 8.50: d: 1H; 12.30: bs: 1H | 167 |
| 3.22 | cyclohexyl | (DMSO + TFA) 0.80–1.60: m: 11H; 1.85–2.30: mt: 2H; 3.40: dq: 1H; 7.50–8.30: m: 7H | 198 |
| 3.23 | 3-methylphenyl (Me) | (DMSO) 1.85: s: 3H; 2.45–2.65: mt: 2H; 4.65: dq: 1H; 6.60–6.90: m: 4H; 7.50–8.15: m: 7H; 8.40: bd: 1H; 12.20: bs: 1H | 102 |

TABLE 7

Structure: Naphthalene-SO₂NH—CH(R₂)—CH₂—COONSu

| Preparations | R₂ | NMR | m.p. ° C. |
|---|---|---|---|
| 3.24 | 3-isopropoxyphenyl (OiPr) | — | 97 |
| 3.25 | 3-methoxyphenyl (OMe) | — | 142 |
| 3.26 | 4-methoxyphenyl (OMe) | — | 135 |
| 3.27 | 3-chlorophenyl (Cl) | — | 163 |
| 3.28 | 3-trifluoromethylphenyl (CF₃) | — | 142 |
| 3.29 | 1-methylnaphthyl | (DMSO + TFA) 2.70: s: 4H; 3.25: d: 2H; 5.60: t: 1H; 7.05–7.95: m: 14H | 192 |
| 3.30 | 3-fluorophenyl (F) | (DMSO) 2.70: s: 4H; 2.95–3.10: mt: 2H; 4.75: dq: 1H; 6.50–6.90: m: 4H; 7.45–8.10: m: 7H; 8.60: d: 1H | 174 |
| 3.31 | cyclohexyl | (DMSO + TFA) 0.60–1.60: m: 11H; 2.40–2.80: mt: 2H; 2.70: s: 4H; 3.35: mt: 1H; 7.50–8.30: m: 7H | 135 |
| 3.32 | 3-methylphenyl (Me) | — | 142 |

The acids described above (Preparations 3.15 to 3.23) are converted by the action of N-hydroxysuccinimide in the presence of DCC in dioxane. The compounds obtained are described in Table 7 below.

Preparation 3.33
3-(3,4-Dichlorobenzenesulphonamido)-3-phenylpropionic acid.
A) 3,4-Dichlorophenylbenzenesulphonyl chloride.

5.4 g of (3,4-dichloro)thiophenol are suspended in 60 ml of water; 0.234 g of $FeCl_3$ is added and chlorine is bubbled through for one hour at a temperature below 10° C. The mixture is evaporated, drained, washed with water and then dried by azeotropic entrainment in order to obtain 6.7 g of the expected compound.

B) 3-(3,4-Dichlorobenzenesulphonamido)-3-phenylpropionic acid.

The process is then carried out according to the procedure of Preparation 3.1 in order to obtain the expected compound.

NMR (DMSO) : 2.5–2.9 : m : 2H; 4.6–4.8 : q : 1H; 7.1 : s : 5H; 7.5–7.7 : mt : 3H; 8.7 : d : 1H; 12.4 : s : 1H.

Preparation 3.34
3-(5,6,7,8-Tetrahydronaphth-2-ylsulphonamido)-3-phenylpropionic acid.
A) Sodium 5,6,7,8-tetrahydronaphthalene-2-sulphonate.

3.9 g of 1,2,3,4-tetrahydronaphthalene are dissolved-in 10 ml of anhydrous $CCl_4$ at 0° C.; 4.3 g of dioxane in 10 ml of $CCl_4$ are added, followed by 6.1 ml of sulphuric anhydride. The mixture is left stirring for 18 hours at RT and then for 3 hours at 80° C. A water/ice mixture is added and the resulting mixture is extracted with ether. The aqueous phase is adjusted to pH=6.5 by addition of 5N NaOH. The product is drained and dried over $Na_2SO_4$ and then by azeotropic entrainment. 10.6 g are obtained.

B) 5,6,7,8-Tetrahydronaphthalene-2-sulphonyl chloride.

2 g of the sulphonate obtained in the above step are mixed with 5 g of phosphorus pentachloride and the mixture is refluxed for 6 hours. It is evaporated, poured onto a water/ice mixture and then extracted with DCM, dried over $Na_2SO_4$ and evaporated in order to obtain 1.5 g of the expected compound.

C) 3-(5,6,7,8-Tetrahydronaphth-2-ylsulphonamido)-3-phenylpropionic acid.

The process is then performed according to the procedure of Preparation 3.1 in order to obtain the expected product.

NMR (DMSO) : 1.6–1.8 : m : 4H; 2.5–2.8 : m : 6H; 4.5–4.7 : dd : 1H; 7–7.2 : m : 7H; 7.3 : d : 1H; 8.1 : d : 1H; 12.3 : s : 1H.

Preparation 3.35
1-(Naphth-2-ylsulphonamido)indane-2-carboxylic acid.
A) Methyl (1-oxo)indan-2-carboxylate.

The reaction is carried out according to J. Med. Chem., 1970, 650. A suspension of 6.75 g of sodium hydride at 80% in oil and 45 g of methyl carbonate in 120 ml of benzene are mixed together. 11.9 g of 1-indanone dissolved in 100 ml of benzene are added, at 60° C., over 1 and a half hours and the mixture is then refluxed. After 1 hour, the benzene is distilled off. Xylene is added and the mixture is again refluxed. After 1 hour, it is cooled, 30 ml of AcOH are added and the resulting mixture is poured onto 200 ml of a water/ice mixture containing 30 ml of 1N HCl. The insoluble material is removed by filtration and the filtrate is extracted with $Et_2O$. The extracts are washed with water, with saturated $NaHCO_3$ solution, with water, with saturated NaCl solution and then dried over $Na_2SO_4$. The product is chromatographed on silica, eluting with EtOAc/hexane (1.3; v/v) in order to obtain 3.05 g of the expected compound.

NMR (DMSO) : 3.25–3.50 : mt : 2H; 3.70 : ds : 3H; 4.85–4.90 : mt : 1H; 7.40–7.80 : m : 4H. Multiple signals since the product is partly in enolic form.

Comment using THF as solvent instead of benzene and xylene, a better yield is obtained: 67% instead of 30%.

B) Methyl 1-hydroxyiminoindan-2-carboxylate.

The reaction is carried out according to J. Heterocycl. Chem., 1974, 11, 982. 3.04 g of the compound of the above step in 9 ml of MeOH are added over 10 minutes to a mixture of 2.21 g of sodium acetate and 3.1 g of hydroxylamine hydrochloride in 3 ml of water. The mixture is then refluxed for 1 hour 30 minutes, after which it is cooled and extracted with EtOAc. The extracts are washed with water, with ¾ saturated $NaHCO_3$ solution, with water and with saturated NaCl solution. After evaporating off the EtOAc, 3.28 g of the expected compound are obtained in solid form.

C) Methyl 1-aminoindan-2-carboxylate hydrochloride.

3.27 g of the compound of the above step are dissolved in 80 ml of EtOH, 1.2 g of 10% Pd/C are added, followed by 20 ml of 1M hydrochloric ethanol and the mixture is left stirring under a pressure of hydrogen (5 bar) at RT overnight. The catalyst is filtered off, the filtrate is concentrated under vacuum and the residue is then taken up in EtOAc and water. The water is separated out after settling of the phases has taken place and is then brought to pH=8.5 by addition of 2N NaOH. This phase is extracted with EtOAc, washed with water, with saturated NaCl solution, dried over $Na_2SO_4$ and evaporated. The residue is taken up in 20 ml of MeOH and 6 ml of 2.5N HCl. The mixture is concentrated under vacuum and the residue is then triturated from $Et_2O$. 2.71 g of the expected compound are obtained in the form of a powder.

D) Methyl 1-(2-naphthalenesulphonamido)indan-2-carboxylate.

0.91 g of the above compound is placed in 10 ml of chloroform and 0.95 g of 2-naphthalenesulphonyl chloride is then added portionwise, followed by portionwise addition of 0.68 ml of DIPEA in order to maintain the mixture at pH=7–8. After 3 hours, the reaction medium is extracted with EtOAc and then washed with 0.05N NaOH, 0.25N HCl, with water and with saturated NaCl solution. 0.99 g of the expected compound is obtained in the form of a pink-white solid.

NMR (DMSO+TFA) : 2.80–3.30 : mt : 2H; 3.40 : s : 3H; 3.50 : q : 1H; 5.10 : d : 1H; 6.40–8.50 : mt : 11H.

E) 1-(Naphth-2-ylsulphonamido)indan-2-carboxylic acid.

0.98 g of the compound of the above step is placed in 10 ml of MeOH, 1 ml of 8.36N KOH is added, the mixture is heated at 50° C. for 3 hours and a further 0.25 ml of 8.36N KOH is then added. After 2 hours, the medium is diluted by addition of water and EtOAc and the pH is brought to 2.5 by addition of 1N HCl. The organic phase is separated out after settling of the phases has taken place, washed with $H_2O$, with saturated NaCl solution and then dried over $Na_2SO_4$ and evaporated. 0.80 g of the expected compound is obtained in the form of a foam.

Preparation 3.36
[2-(2-Naphthalenesulphonyl)-1,2,3,4-tetrahydro-1-isoquinolyl]acetic acid.

1.91 g of (1,2,3,4-tetrahydro-1-isoquinolyl)acetic acid (Preparation 2.18) are suspended in 25 ml of dioxane, 10 ml of 1N NaOH are added, followed by portionwise addition of 2.3 g of 2-naphthalenesulphonyl chloride, and the mixture is maintained at pH=10.5–12 by addition of 1N NaOH. The mixture is kept stirring at a constant pH for 2 hours at RT. The reaction medium is diluted with 100 ml of water and is then washed twice with EtOAc and brought to pH=1.2 by addition of 6N HCl in the presence of EtOAc. This mixture is extracted with EtOAc, washed with saturated NaCl solution, dried over $Na_2SO_4$ and evaporated to dryness. The expected product crystallizes from heptane, and is drained, washed with heptane and then dried to give 3.14 g, m.p.=132° C.

NMR (DMSO+TFA) : 2.40–2.80 : m : 4H; 3.40–3.90 : m : 2H; 5.45 : t : 1H; 6.90–7.20 : m : 4H; 7.50–8.40 : m : 7H.

Preparation 3.37

The 2,5-dioxo-1-pyrrolidinyl ester of the above acid is prepared by the action of NSuOH in the presence of DCC in dioxane.

NMR (DMSO+TFA) : 2.50–2.70 : m : 2H; 2.75 : s : 4H; 3.10–3.35 : mt : 2H; 3.50–3.80 : mt : 2H; 5.50 : t : 1H; 6.80–8.40 : m : 11H.

Preparation 3.38

3-(2-Naphthalenesulphonamido) -3-phenylpropionic acid, (R) isomer.

2 g of the compound of step 2.19 are placed in 30 ml of dioxane in the presence of 7.2 ml of 2N NaOH; 1.6 g of 2-naphthalenesulphonyl chloride are added portionwise while maintaining the mixture at pH=10.5–11.5 by addition of 1N NaOH. After stirring for 2 hours at RT, the mixture is diluted by addition of 100 ml of water and is then washed with EtOAc (several times). The aqueous phase is diluted with EtOAc and then treated with 2N HCl until the pH=2.2. The resulting mixture is extracted with EtOAc, washed with saturated NaCl solution, dried over $Na_2SO_4$ and evaporated to dryness. The expected compound crystallizes from heptane, and is drained, washed with heptane and then dried. 2.2 g are obtained, m.p.=123–126° C.

$\alpha_D^{25}$=+67.9 (c=1; MeOH)

Preparation 3.39

2,5-Dioxo-1-pyrrolidinyl 3-(2-naphthalenesulphonamido)-3-phenylpropionate, (R) isomer.

A solution of 2 g of the above compound and 657 mg of N-hydroxysuccinimide in 35 ml of dioxane is prepared and 1.24 g of DCCI in 10 ml of dioxane are gradually added. After stirring for 5 hours at RT, the DCU is drained and washed with acetone and the filtrate is then evaporated to dryness. The residue is taken up in isopropanol. The product which crystallizes is drained, washed with $Et_2O$ and then dried. 2.18 g of the expected compound are obtained.

Preparations 3.40 and 3.41

The process is performed as in the 2 preparations described above, starting with the compound of Preparation 2.21 in order to obtain 3-(2-naphthalenesulphonamido)-3-phenylpropionic acid, (S) isomer and its 2,5-dioxo-1-pyrrolidinyl ester.

Preparation 3.42

3-(4-Chlorophenyl)-3-(2-naphthalenesulphonamido) propionic acid, (R) isomer.

A) 3-(4-Chlorophenyl)-3-(phenylacetamido)propionic acid.

9.6 g of 3-amino-3-(4-chlorophenyl)propionic acid are dissolved in 200 ml of dioxane and about 50 ml of 1N NaOH in order to reach pH=10.5–11.5. The medium is cooled to +5° C. and 6.34 ml of phenylacetyl chloride are then gradually added, while maintaining the mixture at pH=10.5–11.5 and at a temperature of between +5° C. and +10° C. Stirring is continued for 1 and a half hours and the medium is then concentrated to one-half before diluting with 500 ml of water. The resulting mixture is washed twice with EtOAc and then acidified to pH=1–2 by addition of 6N HCl. The solid is drained, washed with water and dried to give 14 g of the expected compound.

B) 3-Amino-3-(4-chlorophenyl)propionic acid, (R) isomer.

This step is carried out according to Syn. Letters, 1993, 339. 16.8 g of the compound of the above step are suspended in 300 ml of water and 1N $NH_4OH$ is added until a pH=7.5 is obtained. 0.6 ml of Sigma penicillamidase® is added and the mixture is left stirring for 72 hours at 40° C. The expected compound precipitates. It is drained, washed with water and with acetone and then dried at 40° C. 2.85 g are obtained.

$\alpha_D^{25}$=−5° (c=1, 1N HCl)

C) 3-(4-Chlorophenyl)-3-(2-naphthalenesulphonamido) propionic acid, (R) isomer.

1 g of the compound obtained in the above step is dissolved in 15 ml of dioxane and 5 ml of 1N NaOH in order to reach pH=10.5–11.5. 1.15 g of 2-naphthalenesulphonyl chloride are gradually added while keeping the pH constant. After stirring for 2 hours at RT, the medium is diluted by addition of an equal volume of water and is then washed twice with EtOAc. The medium is acidified to pH=1.3 by addition of 6N HCl. This mixture is extracted with EtOAc and the extracts are washed with saturated NaCl solution (several times) The resulting solution is dried over $Na_2SO_4$ and evaporated to dryness, and the expected product then crystallizes from heptane. 1.31 g are obtained.

$\alpha_D^{25}$=+92° (c=1; MeOH)

Preparation 3.43

The 2,5-dioxo-1-pyrrolidinyl ester of the above acid is prepared according to the usual technique.

Preparation 3.44

4-Phenyl-3-(2-naphthalenesulphonamido)butanoic acid, (S) isomer.

1.08 g of the compound of Preparation 2.20 are dissolved in 30 ml of dioxane and 10 ml of water. 10N NaOH is added in order to reach pH=14 and 1.13 g of 2-naphthalenesulphonyl chloride are then added portionwise, while maintaining the mixture at pH=10.5–11.5. Stirring is continued for 2 hours and the mixture is then diluted with water and washed with EtOAc. It is again diluted with EtOAc and acidified to pH=2 by addition of 2N HCl and extracted with EtOAc; the extracts are washed with saturated NaCl solution (several times) and then dried and evaporated to dryness. On addition of heptane, the expected product crystallizes. 1.25 g are obtained.

$\alpha_D^{25}$=−26.8 (c=1; MeOH)

Preparation 3.45

The 2,5-dioxo-1-pyrrolidinyl ester of the above acid is prepared using the usual techniques.

Preparation 3.46

(2S,4R) (4-(Benzyloxy)-1-(2-naphthalenesulphonyl)-2-pyrrolidinyl)acetic acid.

A) 4-(Hydroxy)-1-(2-naphthalenesulphonyl)pyrrolidine-2-carboxylic acid.

2.62 g of (2S,4R)-4-hydroxyproline are dissolved in 15 ml of water containing 5.9 g of $Na_2CO_3$ and 5.21 g of 2-naphthalenesulphonyl chloride are added. After vigorous stirring for 18 hours at RT, the mixture is drained and the filtrate is then acidified to pH=1. The resulting mixture is again drained, washed with water and dried in order to obtain 4.1 g of the expected compound.

B) 4-(Benzyloxy)-1-(2-naphthalenesulphonyl)2-pyrrolidinylacetic acid.

1 g of the compound of the above step is dissolved in 20 ml of DMF at 0° C. under nitrogen; 0.204 g of sodium hydride at 80% in oil is added and the mixture is then left stirring for 1 hour at 0° C. and for 30 minutes at RT. The mixture is cooled to 0° C. and 10 mg of 16-crown-6 crown ether and 0.921 ml of benzyl bromide are then added. The mixture is left stirring for 1 hour at 0° C and then for 18 hours at 50° C. and 10 ml of 1N NaOH are added. After stirring for 18 hours at RT, the mixture is diluted with water and then extracted with ether and acidified to pH=2 by addition of 1N HCl. The resulting mixture is extracted with EtOAc and the extracts are dried over $Na_2SO_4$ and evaporated in order to obtain 0.8 g of the expected compound.

C) (2S,4R)-4-Benzyloxy-2-hydroxymethyl-1-(2-naphthalenesulphonyl)pyrrolidine.

2.8 g of the compound of the above step are dissolved in 20 ml of THF. 1.12 ml of $Et_3N$ and 0.968 ml of ethyl chloroformate are added over 30 minutes at RT, followed by addition of 0.762 g of sodium borohydride in 5 ml of water. After stirring for 20 hours at RT, the mixture is evaporated and the residue is taken up in 20 ml of water and acidified to pH=3 by addition of 1N HCl. The product is drained, washed with water, dried and then precipitated from an EtOAc/hexane mixture in order to obtain 1.9 g of the expected compound.

D) (2S,4R)-4-Benzyloxy-2-mesyloxymethyl-1-(2-naphthalenesulphonyl)pyrrolidine.

3 g of the compound of the above step are dissolved in 100 ml of DCM at 0° C. and 1.28 ml of $Et_3N$ and then 0.72 ml of mesyl chloride are added. After stirring for 30 minutes at 0° C., a further 1.28 ml of $Et_3N$ and then 0.72 ml of mesyl chloride are added, after which the mixture is left stirring for 30 minutes at RT. It is washed, while cold, with $KHSO_4/K_2SO_4$ and the insoluble material is then filtered off and the filtrate is dried and evaporated. The residue is taken up in $Et_2O$ and used without further purification in the following step.

E) (2S,4R) 4-Benzyloxy-2-cyanomethyl-2-(2-naphthalenesulphonyl)pyrrolidine.

The product of the above step is dissolved in 50 ml of DMSO, 2 g of 10-crown-6 crown ether are added and the mixture is cooled on an ice bath. 5 g of potassium cyanide are then added and the mixture is heated for 4 hours at 50° C. The medium is diluted with 250 ml of EtOAc and is then washed with water, dried and evaporated. The residue is taken up in ether. The expected compound crystallizes and 1.7 g are obtained.

F) Ethyl (2S,4R) (4-(benzyloxy)-1-(2-naphthalenesulphonyl)-2-pyrrolidinyl)acetate.

1.6 g of the compound of the above step are dissolved in 50 ml of HCl-saturated ethanol at 0° C. The mixture is left stirring for 48 hours at +4° C. and is then evaporated. The residue is taken up in EtOH and evaporated (twice) and then taken up in $Et_2O$ and evaporated (twice). 20 ml of boiling water are added and a few ml of dioxane/EtOH mixture are then added to homogenize it. The solution is heated for 15 minutes at 100° C. This mixture is evaporated and the residue is taken up in dioxane and then neutralized to pH 6 by addition of 1N NaOH. The solution is used without further purification in the following step.

G) (2S,4R) (4-Benzyloxy)-1-(2-naphthalenesulphonyl)-2-pyrrolidinyl)acetic acid.

2.4 ml of 5N NaOH are added to the solution of the above step and the mixture is heated at 50° C. for 30 minutes. The solvent is evaporated off and the residue is then acidified to pH=3 by addition of concentrated HCl. The product is drained, washed with water and dried in order to obtain 1.44 g of the expected compound.

Preparation 4.1

A) N-(2-(4-(3,4-Dihydroimidazol-2-yl)phenyl)-1-((1-pyrrolidinyl)carbonyl)ethyl)-3-(3,4-dichlorophenyl)-3-(N-Boc)aminopropionamide.

1.09 g of 1-[2-amino-3-(4-(3,4-dihydroimidazol-2-yl) phenylpropionyl]pyrrolidine dihydrochloride are dissolved in 15 ml of DMF, 350 µl of $Et_3N$ are added and the mixture is stirred for a few minutes before adding 835 mg of 3-((N-Boc)amino)-3-(3,4-dichlorophenyl)propionic acid (obtained in Preparation 2.6) and 515 mg of DCC.

After stirring for 3 hours, the mixture is evaporated to dryness and the residue is then taken up in methanol. The DCU is drained and the filtrate is concentrated to one-half and diluted with acetone. This mixture is filtered and then evaporated to dryness. The residue is chromatographed, eluting with a chloroform/methanol mixture (from 100/2.5 to 100/20; v/v).

B) N-(2-(4-(3,4-Dihydroimidazol-2-yl)phenyl)-1-((1-pyrrolidinyl)carbonyl)ethyl)-3-(3,4-dichlorophenyl)-3-aminopropionamide.

The crude product obtained in the above step is placed in 20 ml of a solution of 4N HCl in dioxane and a sufficient amount of MeOH to allow complete dissolution. After 1 hour at RT, the mixture is evaporated to dryness and the residue is triturated twice from ether and then drained, washed with ether and dried under vacuum in the presence of KOH. 225 mg of the expected compound are obtained.

Preparation 4.2

N-[2-(4-Cyanophenyl)-1-((1-pyrrolidinyl)carbonyl)ethyl]-3-phenyl-3-aminopropionamide trifluoroacetate, (R,R) isomer.

A) N-[2-(4-Cyanophenyl)-1-((1-pyrrolidinyl)carbonyl) ethyl]-3-phenyl-3-(N-Boc)aminopropionamide, (R,R) isomer.

The 2,5-dioxo-1-pyrrolidinyl ester of the acid obtained in Preparation 2.19, step B is prepared. 800 mg of this compound are added to a mixture containing 790 mg of the compound of Preparation 1.13 in 15 ml of acetonitrile and 380 µl of DIPEA. The mixture is left stirring for a few hours and is then left overnight at RT. The medium is evaporated to dryness and the residue is taken up in $KHSO_4/K_2SO_4$ and then extracted with EtOAc. The organic phase is washed with saturated NaCl solution and then dried over $Na_2SO_4$ and evaporated to dryness. 1.1 g of the expected compound are obtained, this compound crystallizing from heptane.

B) N-[2-(4-Cyanophenyl)-1-((1-pyrrolidinyl)carbonyl) ethyl]-3-phenyl-3-aminopropionamide trifluoroacetate, (R,R) isomer.

1 g of the compound of the above step is dissolved in 6 ml of DCM, 6 ml of TFA are then added and the mixture is left stirring for 35 minutes at RT. The reaction medium is evaporated to dryness, the residue is redissolved in isopropanol and then evaporated, the residue is triturated from $Et_2O$ and the product is drained and dried in order to obtain 0.88 g of the expected compound.

EXAMPLE 1

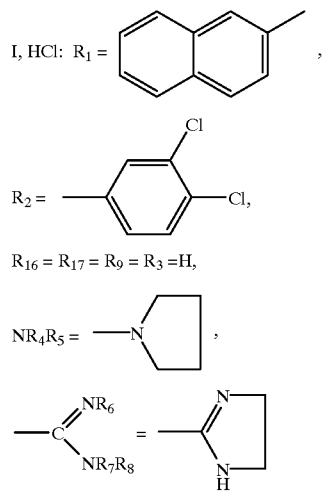

210 mg of the compound of Preparation 4.1 are dissolved in 10 ml of dioxane and 5 ml of water, and 1N sodium hydroxide is added in order to reach pH=9.5. 84 mg of 2-naphthalenesulphonyl chloride are added 3 times, while maintaining the mixture at pH=9–9.5 by addition of 0.5N sodium hydroxide. After leaving overnight at RT, the medium is diluted with water and acidified to pH=2.5 by addition of 1N HCl. The solid formed is chromatographed on Sephadex® LH 20, eluting with methanol. The fraction containing the expected product is concentrated, treated with a solution of 4N HCl in dioxane and then evaporated to dryness; the residue is taken up in ether, drained and dried. 41 mg of the expected compound are obtained.

MH$^+$: 692 : dichloro isotopic profile

NMR (DMSO+TFA) 1.40–1.70 : m : 4H; 2.50–3.40 : m : 8H; 4.00 : ds : 4H; 4.45–4.70 : m : 2H; 6.60–8.00 : m : 14H

EXAMPLE 2

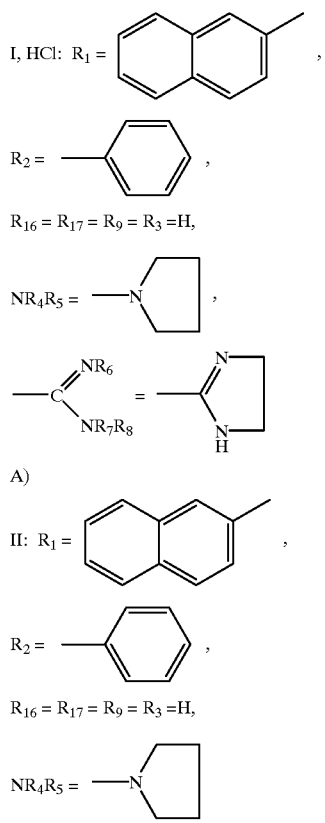

715 mg of the compound of Preparation 1.1, 15 ml of CH$_3$CN, 250 μl of triethylamine, 710 mg of the compound of Preparation 3.2 and 450 mg of DCC are mixed together and left stirring for 5 hours at RT. The mixture is evaporated to dryness, the residue is taken up in acetone, the DCU is drained and the filtrate is then evaporated to dryness again. The residue is triturated from ether and the product is then isolated by decanting, several times. It is dried under vacuum in the presence of P$_2$O$_5$ in order to obtain 610 mg of the expected compound, m.p.=195–200° C.

NMR (DMSO+TFA) 1.40–1.70 : m : 4H; 2.30–3.40 : m : 8H; 4.40–4.60 : m : and 4.60–4.70 : m : 2H; 6.75–8.15 m : 16H

B)

600 mg of the product obtained in the above step are dissolved in 20 ml of a solution of ethanol saturated with hydrochloric acid, at 0° C. After leaving overnight in a refrigerator, the mixture is evaporated to dryness and the residue is then dried under vacuum in the presence of KOH. The product obtained is diluted in 25 ml of anhydrous ethanol and 134 μl of ethylenediamine in 2 ml of anhydrous EtOH are then added several times. After leaving overnight at RT, the mixture is evaporated to dryness and the residue is then chromatographed on silica, eluting with a chloroform/methanol mixture (85/15; v/v). The fractions containing the expected compound are combined, evaporated and then taken up in dilute hydrochloric ether. After draining and drying under vacuum in the presence of KOH, 180 mg of the expected product are obtained.

MH$^+$: 624

NMR (DMSO+TFA) 1.40–1.80 : m : 4H; 2.55–3.45 : m : 8H; 4.00 : s : 4H; 4.55 : bt : and 4.70 : bt : 2H; 6.70–8.20 : m : 16H

EXAMPLE 3

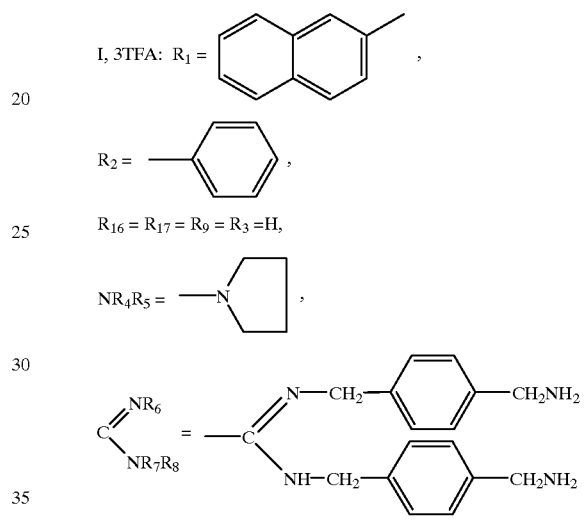

A)

800 mg of the compound obtained in Example 2, step A are dissolved in 20 ml of a saturated solution of HCl in anhydrous EtOH. After leaving overnight in a refrigerator, the mixture is evaporated to dryness and the residue is then dried under vacuum in the presence of KOH. The residue is dissolved in 30 ml of anhydrous EtOH and 175 μl of Et$_3$N are added, followed by 350 mg of N-Boc-(4-aminomethyl)benzylamine. After 48 hours at RT, the mixture is evaporated to dryness and the residue is then chromatographed on Sephadex® LH 20, eluting with MeOH. 2 fractions containing two different compounds are obtained. For one (fraction 1, 570 mg), the amidine is monosubstituted with a group R$_8$=–4((N-Boc)aminomethyl)benzyl and R$_6$ and R$_7$=H; for the other (fraction 2, 150 mg), the amidine is disubstituted with R$_6$=R=–4(N-(Boc)aminomethyl)benzyl and R$_7$=H.

B)

125 mg of the compound of fraction 2 obtained in the above step are suspended in 1 ml of DCM, 1 ml of TFA is added and the mixture is left stirring for 40 minutes at RT. After evaporating the medium to dryness, the residue is dissolved in isopropanol and is then evaporated to dryness again; the residue is triturated from Et$_2$O, drained, washed with Et$_2$O and then dried. 110 mg of the expected compound are obtained.

MH$^+$: 836

NMR (DMSO+TFA) 1.40–1.80 : m : 4H; 2.40–3.30 : m : 8H; 3.90–4.80 : m : 10H; 6.80–8.45 : m : 24H

EXAMPLE 4

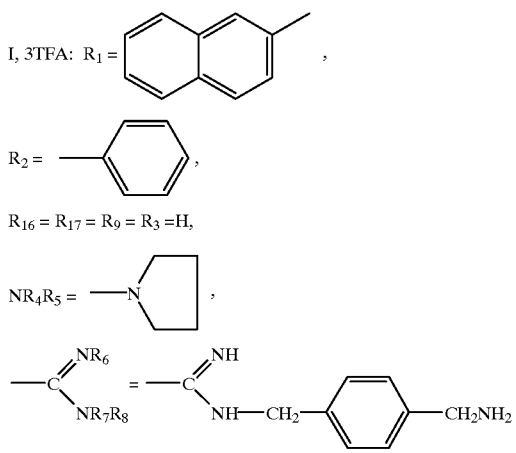

$R_{16} = R_{17} = R_9 = R_3 = H$, 535 mg of the compound of fraction 1 obtained in Example 3, step A are suspended in 8 ml of DCM, 8 ml of TFA are added and the mixture is left stirring for 40 minutes at RT. After evaporating the medium to dryness, the residue is triturated from ether and then dried under vacuum in the presence of potassium hydroxide. 520 mg of the expected compound are obtained.

$MH^+$: 717

NMR (DMSO+TFA) ; 1.30–1.70 : m : 4H; 2.20–3.30 : m : 8H; 3.90 : s : 2H; 4.40–4.70 : m : 4H; 6.80–8.00 : m : 20H

EXAMPLE 5

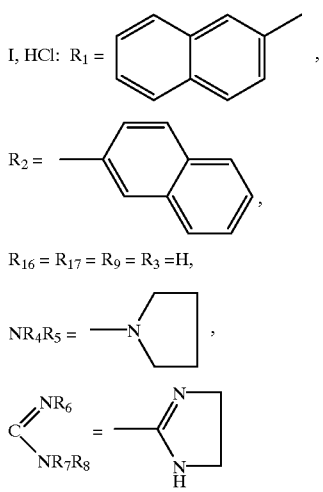

$R_{16} = R_{17} = R_9 = R_3 = H$, 960 mg of the compound of Preparation 3.8 in 20 ml of DMF are mixed with 852 mg of the compound of Preparation 1.2 and 280 Al of $Et_3N$ and the mixture is adjusted to pH=7–7.5 by addition of $Et_3N$. After stirring overnight, the mixture is evaporated to dryness and the residue is then taken up in methanol and chromatographed on Sephadex® LH 20, eluting with methanol. The fractions containing the product are combined, evaporated and then taken up in 20 ml of butanol, 10 ml of 1N HCl and 10 ml of water. After stirring and separation of the phases by settling, the organic phase is evaporated. The residue is chromatographed on Sephadex® LH 20, eluting with methanol, and the fractions collected are subjected to the same treatment as above. 180 mg of the expected compound are obtained.

$MH^+$: 674

NMR (DMSO+TFA) 1.00–1.70 : m : 4H; 2.30–3.20 : m : 8H; 4.05 : ds : 4H; 4.50 : mt : and 4.80 : mt : 2H; 7.05–8.10 : m : 18H

EXAMPLE 6

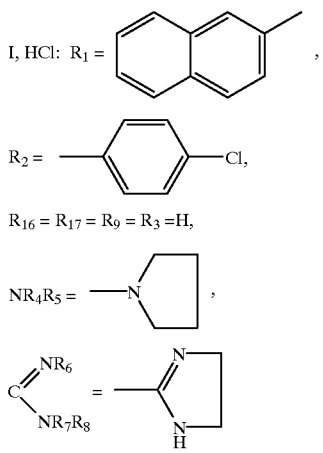

$R_{16} = R_{17} = R_9 = R_3 = H$,

This compound is obtained by working as in Example 5, starting with the compounds of Preparations 3.9 and 1.2.

$MH^+$: 658 : monochloro isotopic profile

NMR (DMSO+TFA) 1.40–1.70 : m : 4H; 2.40–3.30 : m : 8H; 3.90 : ds : 4H; 4.40–4.65 : m : 2H; 6.70–8.00 : m : 15H

EXAMPLE 7

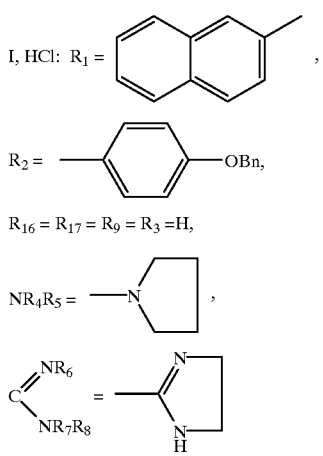

$R_{16} = R_{17} = R_9 = R_3 = H$, 880 mg of the compound of Preparation 1.2 are dissolved in 15 ml of DMF and 300 µl of $Et_3N$, 1.12 g of the compound of Preparation 3.10 are added and the mixture is left stirring for 5 hours at RT. After evaporating the medium to dryness, the residue is taken up in a mixture of 1N HCl and butanol, and the upper-phase is then separated out after settling has taken place and evaporated to dryness. The residue is chromatographed on Sephadex® LH 20, eluting with MeOH. The product thus obtained is taken up in a solution of 1N HCl in butanol and then evaporated to dryness and the residue is triturated from ether, drained, washed with ether and dried in order to obtain 330 mg of the expected product.

MH+: 730

NMR (DMSO+TFA) ; 1.45–2.25 : m : 4H; 2.30–3.30 : m : 8H; 3.85 : s : and 3.95 : s : 4H; 4.50–4.70 : m : 4H; 6.35–8.00 : m : 20H.

EXAMPLE 8

I, HCl: $R_1$ = 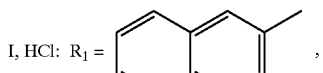, $R_2$ = 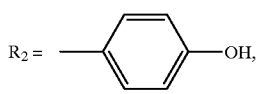, $R_{16} = R_{17} = R_9 = R_3 =$ H, 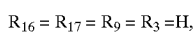

$NR_4R_5$ = 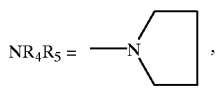,

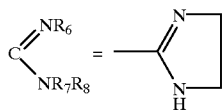

The debenzylation reaction is carried out according to J. Chem. Educ., 1987, 64, 1062.

425 mg of the compound of Example 7 in 20 ml of methanol are mixed with 120 mg of ammonium formate in the presence of 500 mg of 10% Pd/C containing 50% water. After refluxing for 24 hours, the palladium is filtered off and washed with methanol and the filtrate is evaporated to dryness; the residue is dissolved in methanol and then chromatographed on Sephadex® LH 20, eluting with methanol. The product obtained is taken up in a mixture of a solution of 2N HCl in water and butanol; after stirring, the aqueous fraction is extracted with butanol and the combined organic fractions are evaporated to dryness. The residue is taken up in ether and the product is filtered off, washed with ether and dried. 171 mg of the expected product are obtained.

MH+: 640

NMR (DMSO+TFA) 1.50–1.85 : m : 4H; 2.40–3.30 : m : 8H; 4.05 : ds : 4H; 4.50–4.70 : m : 2H; 6.40–8.20 : m : 15H

The compounds described in Table 8 are prepared as in Examples 7 and 8 above.

TABLE 8

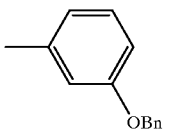

| Examples | $R_2$ | $\overset{NR_6}{\underset{NR_7R_8}{C}}$ | MH+ NMR (DMSO + TFA) |
|---|---|---|---|
| 9 | 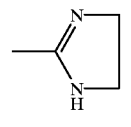 OBn | 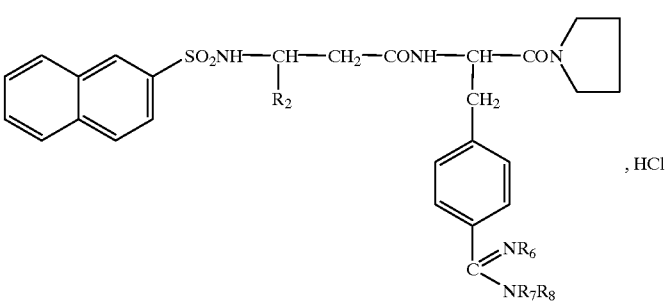 | MH+: 730<br>1.45–1.75: m: 4H; 2.40–3.40: m: 8H; 3.95: s: and 4.00: s: 4H; 4.50–4.70: m: 4H; 6.40–8.10: m: 20H |
| 10 | 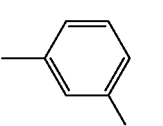 OH | 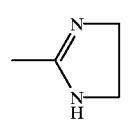 | MH+: 640<br>1.45–180: m: 4H 2.25–3.30: m: 8H 3.95: s: 4H 4.45–4.70: m: 2H 6.30: 8.20: m: 15H |
| 11 | 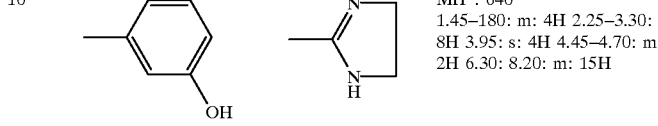 | 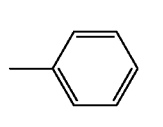 NH(CH$_2$)$_3$N(CH$_3$)$_2$ | MH+: 683<br>1.45–1.80: m: 4H 1.95–2.10: m: 2H 2.75: ds: 6H 2.50–3.60: m: 12H 4.55: m.t.: and 4.70: mt: 2H 6.80–8.10: m: 16H |

EXAMPLE 12

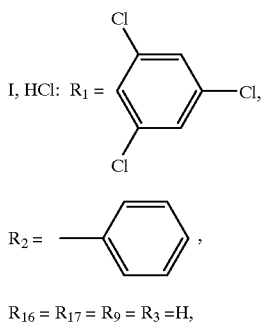

I, HCl: $R_1$ = [3,5-dichlorophenyl], $R_2$ = [phenyl], $R_{16} = R_{17} = R_9 = R_3 =$ H, -continued $NR_4R_5$ = [pyrrolidinyl], $C(=NR_6)NR_7R_8$ = [4,5-dihydro-1H-imidazol-2-yl]

900 mg of the compound of Preparation 1.2 in 10 ml of DMF and 550 μl of Et$_3$N are mixed with 1.04 g of the compound of Preparation 3.1 and 1.3 g of BOP and a sufficient amount of Et$_3$N to reach pH=6–7 are added. After stirring for 5 hours, while maintaining the medium at pH=6–7 by addition of Et$_3$N, the medium is diluted with ether and is then triturated and the phases are allowed to separate by settling (twice). The oil is chromatographed on Sephadex® LH 20, eluting with methanol, and the product obtained is then chromatographed again on silica, eluting with a chloroform/methanol mixture (90/10; v/v). The product obtained is washed with EtOAc in water, with EtOAc and dried. 313 mg of the expected product are obtained.

MH$^+$: 676 : trichloro isotopic profile

NMR (DMSO+TFA) 1.50–1.85 : m : 4H; 2.70–3.20 : m : 8H; 3.95 : bs : 4H; 4.50–4.75 : m : 2H; 6.90–8.00 : m : 11H

Working as in Example 12, the compounds described in the table below are prepared.

TABLE 9

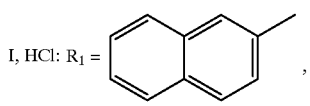

| Examples | $R_2$ | $R_3$ | $C(=NR_6)NR_7R_8$ | MH$^+$ NMR (DMSO + TFA) |
|---|---|---|---|---|
| 13 | 2-hydroxyphenyl | H | 4,5-dihydro-1H-imidazol-2-yl | MH$^+$: 640 1.60–1.80: m: 4H 2.60–3.50: m: 8H 3.80: s: and 4.00: s: 4H 4.60–4.90: m: 2H 6.90–8.70: m: 15H |
| 14 | phenyl | OH | 4,5-dihydro-1H-imidazol-2-yl | MH$^+$: 640 1.40–1.70: m: 4H 2.50–3.20: m: 8H 3.85: ds: 4H 4.00: d.d.: 1H 4.30–4.70: m: 2H 6.55–8.10: m: 16H |

EXAMPLE 15

I, HCl: $R_1$ = [2-methylnaphthyl], $R_2$ = [phenyl], $R_{16} = R_{17} = R_9 = R_3 =$ H, $NR_4R_5$ = [pyrrolidinyl], -continued

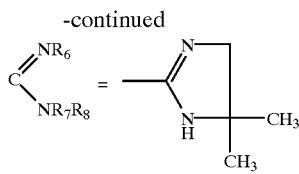

This compound is prepared from the compound prepared in Example 2, step A, and working as in Example 2, step B, using 2-methylpropane-1,2-diamine.

MH+: 652

NMR (DMSO+TFA) 1.30 : s : 6H; 1.30–1.70 : m : 4H; 2.25–3.20 : m : 8H; 3.65 : s : 2H; 4.40–4.70 : m : 2H; 6.70–8.05 : m : 16H

EXAMPLE 16

I, 2HCl: $R_1 =$ 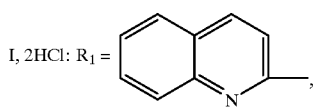, $R_2 =$ 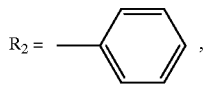, $R_{16} = R_{17} = R_9 = R_3 = H$, $NR_4R_5 =$ 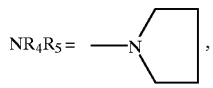,

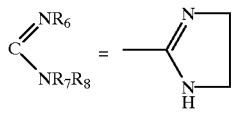

0.812 g of the compound of Preparation 3.13 and 0.810 g of the compound of Preparation 1.2 are dissolved in 10 ml of DMF and 1.22 g of BOP are added, and the mixture is then brought to pH=7 by addition of Et$_3$N. After stirring for 18 hours at RT, the medium is evaporated to dryness. The residue is taken up in EtOAc and saturated NaHCO$_3$ solution, then the aqueous phase is washed with EtOAc and the organic phases are washed with the KHSO$_4$/K$_2$SO$_4$ buffer and with saturated NaCl solution. The resulting solution is dried over Na$_2$SO$_4$ and evaporated. The residue is chromatographed on silica, eluting with a CHCl$_3$/MeOH/ concentrated ammonia mixture (10/0.5/0.1; v/v/v). 0.390 g of the expected compound are obtained.

MH+: 625

NMR (DMSO) : 1.5–1.8 : mt : 4H; 2.5–3.7 : m : 8H; 4 : s : 4H; 4.4–4.6 : mt : 1H; 4.7–4.9 : Mt : 1H; 6.8–7 : mt : 3H; 7–7.1 : mt : 2H; 7.4 : d : 2H; 7.7–8.1 : m : 5H; 8.3–8.4 : m : 2H; 8.7 : d : 1H; 10.7 : s : 1H.

EXAMPLE 17

I, 2HCl: $R_1 =$ 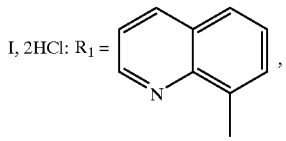, $R_2 =$ 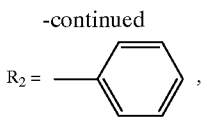, $R_{16} = R_{17} = R_9 = R_3 = H$, $NR_4R_5 =$ 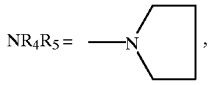,

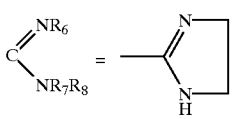

This compound is prepared according to the procedure of the above example, starting with the compound of Preparation 3.14 and that of Preparation 1.2.

MH+: 625

NMR (DMSO) : 1.4–1.7 : mt : 4H; 2.4–3.3 : m : 4H; 4 : mt : 4H; 4.5–4.7 : mt : 2H; 6.7–6.9 : mt : 2H; 7.2–8.4 : m : 16H; 9 : mt : 1H; 10.7 : s : 1H.

EXAMPLE 18

I, HCl: $R_1 =$ 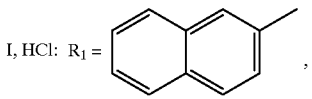, $R_2 =$ 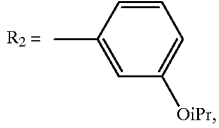, $R_{16} = R_{17} = R_9 = R_3 = H$, $NR_4R_5 =$ 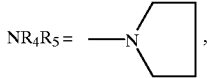,

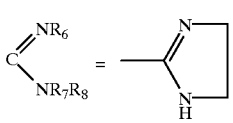

740 mg of the compound of Preparation 1.2 are placed in 10 ml of DMF and 240 μl of DIPEA are added, followed by 740 mg of the compound of Preparation 3.24. After stirring overnight at RT, ether is added, the mixture is decanted and washed again with ether and is then triturated and decanted. The organic phase is chromatographed on Sephadex® LH 20, eluting with MeOH. The fractions of interest are taken up in a mixture containing 5 ml of butanol, 5 ml of 1N HCl and 5 ml of EtOAc. The organic phase is washed with 5 ml of 1N HCl and evaporated to dryness. The residue is dissolved in methanol and precipitated with ether. 470 mg of the expected compound are obtained.

MH+: 682

NMR (DMSO) : 1.00 : d : 6H; 1.45–1.80 : m : 4H; 2.30–3.20 : m : 8H; 3.95 : ds : 4H; 4.05–4.20 : m : 1H; 4.50–4.70 : m : 2H; 6.30–8.40 : m : 17H (15H aromatic+2H amides); 10.70 : bs : 1H.

Working according to the procedure described above, the compounds according to the invention in the table below are prepared from the compounds of Preparations 3.25 to 3.32.

TABLE 10
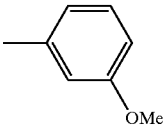
, HCl
| Example | R₂ | NMR | MH⁺ |
|---|---|---|---|
| 19 |  3-OMe-phenyl | (DMSO + TFA) 1.50–1.80: m: 4H; 2.25–3.25: m: 8H; 3.40: s: 3H; 4.00: ds: 4H; 4.45–4.75: m: 2H; 6.35–6.90: mt: 4H; 7.30–8.15: m: 11H | 654 |
| 20 | 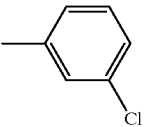 4-OMe-phenyl | (DMSO + TFA) 1.50–1.80: m: 4H; 2.30–3.25: m: 8H; 3.40: s: 3H; 4.00: ds: 4H; 4.60: tq: 1H; 6.40: d: 2H; 6.90: d: 2H; 7.25–8.05: m: 11H | 654 |
| 21 | 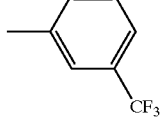 3-Cl-phenyl | (DMSO + TFA) 1.50–1.80: m: 4H; 2.35–3.40: m: 8H; 4.00: ds: 4H; 4.50–4.70: m: 2H; 6.75–7.00: m: 4H; 7.25–8.10: m: 11H | 658–660 |
| 22 | 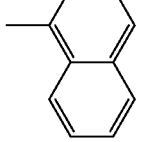 3-CF₃-phenyl | (DMSO + TFA) 1.40–1.80: m: 4H; 2.40–3.40: m: 8H; 3.95: ds: 4H; 4.50–4.65: mt: 1H; 4.75: dq: 1H; 6.90–8.00: m: 15H | 692 |
| 23 | 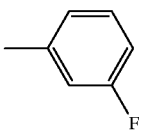 1-naphthyl | (DMSO + TFA) 1.20–1.60: m: 4H; 2.40–3.20: m: 8H; 3.95: bs: 4H; 4.25–4.50: mt: 1H; 5.45: t: 1H; 7.00–7.90: m: 18H | 674 |
| 24 | 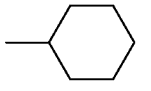 3-F-phenyl | (DMSO + TFA) 1.50–1.75: m: 4H; 2.60–3.40: m: 8H; 4.00: bs: 4H; 4.50–4.75: m: 2H; 6.55–8.10: m: 15H | 642 |
| 25 | cyclohexyl | (DMSO + TFA) 0.60–1.70: m: 15H; 1.80–2.20: m: 2H; 2.60–3.40: m: 7H; 3.90: s: 4H; 4.30–4.60: m: 1H; 7.25–8.25: m: 11H | 630 |
| 26 | 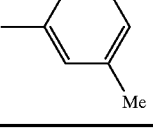 3-Me-phenyl | (DMSO + TFA) 1.50–1.80: m: 4H; 1.90: s: 3H; 2.20–3.30: m: 8H; 4.05: ds: 4H; 4.55–4.75: m: 2H; 6.60–8.10: m: 15H | 638 |

EXAMPLE 27

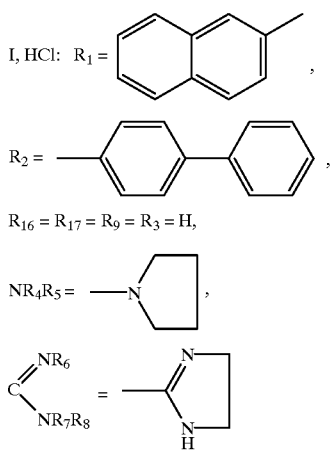

A) N-(2-(4-Cyanophenyl)-1-(1-pyrrolidinylcarbonyl)ethyl)-3-(4-biphenylyl)-3-(N-Boc)aminopropionamide.

1.19 g of the compound of Preparation 1.1 are placed in 30 ml of acetonitrile and 0.46 ml of Et₃N and 1.46 g of the compound of Preparation 2.17 are added. The mixture is left overnight at RT and is then evaporated to dryness and the residue is taken up in KHSO₄/K₂SO₄ and extracted with EtOAc. The extracts are washed with saturated NaCl solution, dried over Na₂SO₄ and the evaporated to dryness. The expected compound crystallizes from heptane and is filtered off, washed with heptane and then dried in order to obtain 1.86 g.

B) N-(2-(4-Cyanophenyl)-1-(1-pyrrolidinylcarbonyl)ethyl)-3-(4-biphenylyl)-3-aminopropionamide trifluoroacetate.

A mixture containing 1.82 g of the compound of the above step in 15 ml of DCM and 15 ml of TFA is left stirring at RT for 35 minutes. The mixture is evaporated to dryness and the residue is dissolved in isopropanol and evaporated to dryness again. The expected product crystallizes from Et₂O and is filtered off, washed with Et₂O and then dried to give 1.37 g.

C)

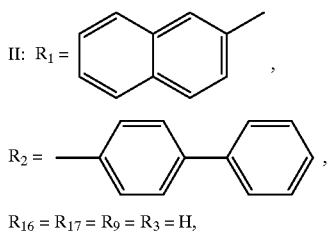

1.34 g of the compound of the above step are placed in 25 ml of DCM and 850 μl of DIPEA and 522 mg of 2-naphthalenesulphonyl chloride in 5 ml of DCM are gradually added. After stirring for 2 hours at RT, the mixture is diluted with 60 ml of DCM and is then washed with KHSO₄/K₂SO₄ and with saturated NaCl solution. The resulting solution is dried over Na₂SO₄ and evaporated to dryness, and the residue is then chromatographed on fine silica, eluting with chloroform containing 1% MeOH. 0.802 g of the expected compound is obtained.

NMR (DMSO+TFA) : 1.45–1.85 : m : 4H; 2.40–3.35 : m : 8H; 4.50–4.90 : mt : 2H; 7.05–8.20 : m : 20H.

D)

0.778 g of the compound of the above step is placed in 50 ml of anhydrous EtOH saturated with HCl, at 0° C.; the mixture is left stirring in a refrigerator until dissolved and is then left in the refrigerator for 48 hours. It is evaporated to dryness and dried in a desiccator under vacuum in the presence of potassium hydroxide for 2 hours. This residue is dissolved in 80 ml of anhydrous EtOH and 206 μl of DIPEA and 93 μl of ethylenediamine are added. After 24 hours at RT, the mixture is evaporated to dryness and the residue is then chromatographed on Sephadex® LH 20, eluting with methanol. The fractions containing the product are taken up in a mixture of 6 ml of butanol and 6 ml of 1N HCl. After stirring and separation of the phases by settling, the organic phase is washed with 3 ml of 1N HCl and evaporated under vacuum. The residue is taken up in Et₂O and the solid formed is filtered off, washed with Et₂O and dried to give 0.495 g of the expected compound.

MH⁺: 700

NMR : 1.40–1.80 : m : 4H; 2.40–3.30 : m : 8H; 3.80 : s : 2H; 3.95 : s : 2H; 4.50–4.80 : mt : 2H; 7.00–8.05 : m : 20H.

EXAMPLE 28

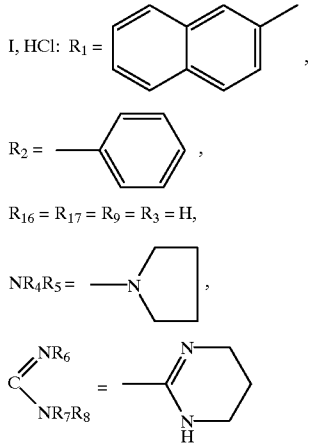

0.790 g of the compound obtained in Example 2, step A is dissolved in 10 ml of EtOH saturated with HCl, at 0° C., and the mixture is left stirring for 48 hours at 0° C. It is evaporated to dryness and the residue is then taken up in EtOH and evaporated (twice). The residue is taken up in DCM and evaporated (twice). The resulting residue is taken up in 20 ml of EtOH and then neutralized by addition of Et₃N. 0.109 ml of diaminopropane is added and the mixture is left for 24 hours at RT. It is evaporated to dryness and the residue is taken up in DCM and washed with KHSO₄/K₂SO₄. Chromatography on silica is then carried out, eluting with a chloroform/methanol/concentrated ammonia mixture (10/1/1; v/v/v). 0.12 g of the expected compound is obtained.

MH+: 638

EXAMPLE 29

I, HCl: R$_1$ = 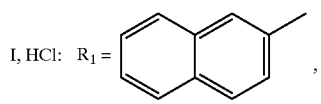,

R$_2$ = 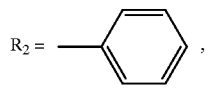,

R$_{16}$ = R$_{17}$ = R$_9$ = R$_3$ = H,

NR$_4$R$_5$ = 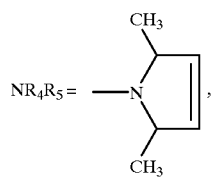, $\text{C}\begin{smallmatrix}\nearrow NR_6 \\ \searrow NR_7R_8\end{smallmatrix}$ = 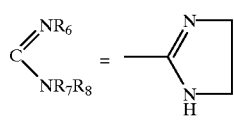

A)

II: R$_1$ = 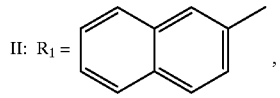,

R$_2$ = 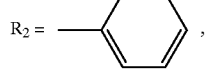,

R$_{16}$ = R$_{17}$ = R$_9$ = R$_3$ = H,

NR$_4$R$_5$ = 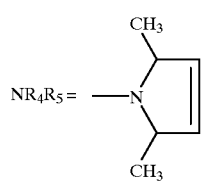

0.888 g of the compound of Preparation 3.2 and 0.957 g of the compound of Preparation 1.4 are dissolved in 5 ml of DMF; 1.22 g of BOP are added and the medium is then adjusted to pH=7 by addition of Et$_3$N. After stirring for 18 hours at RT, the mixture is evaporated to dryness and the residue is then taken up. in EtOAc. The solution is washed with NaHCO$_3$ solution, with KHSO$_4$/K$_2$SO$_4$ and with saturated NaCl solution and is then dried over Na$_2$SO$_4$ and evaporated. The residue is taken up in ether and a few drops of hexane and is then filtered and dried over Na$_2$SO$_4$ in order to obtain 1.1 g of the expected compound.

B)

1 g of the compound of the above step is dissolved in 20 ml of EtOH saturated with HCl, at 0° C. After 48 hours at +4° C., the solution is evaporated and the residue is taken up in EtOH (3 times) and is then evaporated and taken up in DCM (twice). The residue is taken up in 20 ml of EtOH, the pH is then adjusted to 7 by addition of Et$_3$N and 0.122 ml of ethylenediamine is added. After stirring for 18 hours at RT, the mixture is evaporated to dryness and is then taken up in DCM and washed with 10 ml of KHSO$_4$/K$_2$SO$_4$. This solution is chromatographed on silica, eluting with a chloroform/methanol/aqueous ammonia mixture (10/1/0.1; v/v/v) in order to obtain 0.640 g of the expected compound.

MH+: 650

NMR (DMSO+TFA) : 0.8–1.2 : m : 4H; 2.3–3.1 : m : 4H; 4 : s : 4H; 4.3–4.7 : m : 4H; 5.4–5.7 : mt : 2H; 6.8–7.9 : m : 15H; 8.2 : d : 1H.

Working as in Example 12, the compounds described in Table 11 below are prepared.

TABLE 11

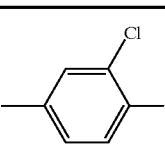

| Example | R$_1$ | R$_2$ | MH+ |
|---|---|---|---|
| 30 | 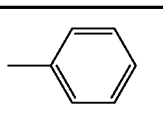 | 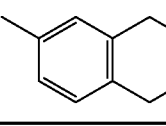 | 642–644 |
| 31 | 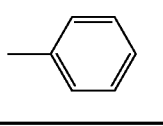 | 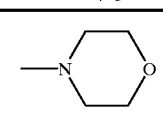 | 628 |

Working according to the procedure of Example 2, steps A and B, the compounds according to the invention in the table below are prepared.

TABLE 12

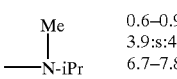

| Example | —NR$_4$R$_5$ | m.p. ° C./NMR (DMSO + TFA) | MH+ |
|---|---|---|---|
| 32 | —N⟨O (morpholine) | 170° C. 2.40–3.45:m:12H; 4.00:se:4H; 4.60–4.90:m:2H; 6.80–8.15:m:16H | 640 |
| 33 | Me / —N-iPr | 0.6–0.9:mt:6H; 2.2–3:m:7H; 3.9:s:4H; 4.3–4.9:m:3H; 6.7–7.8:m:15H; 8.:d:1H | 626 |

TABLE 12-continued

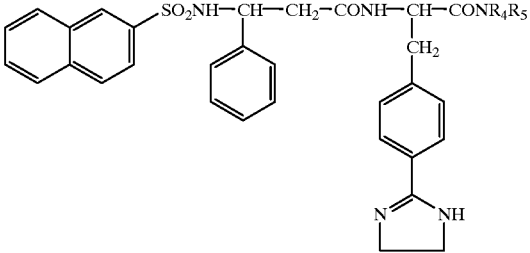

| Example | —NR₄R₅ | m.p. °C./NMR (DMSO + TFA) | MH⁺ |
|---------|--------|---------------------------|-----|
| 34 | Me-pyrrolidine-Me | 0.6–1.6:m:8H; 1.6–1.9:mt:2H; 2.4–3.1:m:4H; 3.2–4:m:6H; 4.2–4.8:m:2H; 6.8–7.9:m:15H; 8:s:1H | 652 |

EXAMPLE 35

I, HCl: R₁ = (2-methylnaphthyl),

R₂ = phenyl,

R₃ = R₁₇ = H, R₉ + R₁₆ = —CH₂—,

—NR₄R₅ = pyrrolidine,

C(=NR₆)NR₇R₈ = 2-imidazoline

A)

II: R₁ = (2-methylnaphthyl),

R₂ = phenyl,

R₃ = R₁₇ = H, R₉ + R₁₆ = —CH₂—,

—NR₄R₅ = pyrrolidine 580 mg of the compound obtained in Example 2, step A are mixed with 250 mg of paraformaldehyde and 60 mg of para-toluenesulphonic acid monohydrate in 25 ml of benzene. The mixture is refluxed in Dean-Stark apparatus for 1 hour. The reaction medium is then washed with saturated NaHCO₃ solution and with saturated NaCl solution and then dried over Na₂SO₄ and evaporated to dryness. The residue is chromatographed on fine silica, eluting with chloroform, in order to obtain 165 mg of the expected compound.

NMR (DMSO+TFA) : 1.55–1.85 : m : 4H; 2.40–3.40 : m : 8H; 4.60–5.50 : m : 4H; 6.90–8.30 : m : 16H.

B)

The process is performed as in Example 2, step B in order to obtain the expected compound, which is purified by chromatography on Sephadex® LH 20, eluting with MeOH.

MH⁺: 636

NMR (DMSO+TFA) : 1.50–1.80 : m : 4H; 2.40–3.30 m : 8H; 3.95 : s : 4H; 4.90–5.45 : m : 4H; 6.90–8.10 : m : 16H.

EXAMPLE 36

I, HCl: R₁ = (2-methylnaphthyl),

R₂ = phenyl,

R₃ = R₁₆ = R₁₇ = H, R₉ = Me,

—NR₄R₅ = pyrrolidine,

C(=NR₆)NR₇R₈ = 2-imidazoline

A)

II: R₁ = (2-methylnaphthyl),

R₂ = phenyl,

R₃ = R₁₆ = R₁₇ = H, R₉ = Me,

—NR₄R₅ = pyrrolidine 105 g of the compound of Example 2, step A are mixed with 0.262 g of potassium carbonate in 12 ml of DMF and 423 µl of methyl iodide are added. The following day, the mixture is evaporated to dryness and the residue is taken up in water and EtOAc. The organic phase is washed with water and with saturated NaCl solution and is then dried over Na₂SO₄.0.6 g of the expected compound is obtained.

MH⁺: 595

NMR (DMSO+TFA) : 1.50–1.80 : m : 4H; 2.20–3.30 : m : 8H; 2.55 : bs : 3H; 4.35–4.65 : mt : 1H; 5.45–5.60 : mt : 1H; 7.10–8.45 : m : 16H.

B)

The process is performed as in Example 2, step B, in order to obtain the expected compound, which is purified by chromatography on silica, eluting with DCM/MeOH (93/7; v/v) and then by a second chromatography on Sephadex® LH 20, eluting with methanol, m.p.=154° C.

MH⁺: 638

NMR (DMSO+TFA) : 1.20–1.80 : m : 4H; 2.10–2.40 : mt : 2H; 2.50 : bs : 3H; 2.40–3.20 : m : 6H; 4.00 : s : 4H; 4.40–4.70 : mt : 1H; 5.35–5.55 : mt : 1H; 7.05–8.40 : m : 16H.

EXAMPLE 37

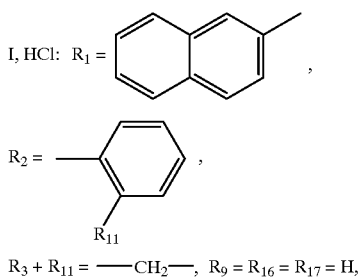

I, HCl: $R_1 =$ $R_2 =$ 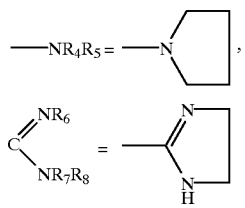

$R_3 + R_{11} =$ —CH$_2$—, $R_9 = R_{16} = R_{17} = H$,

—NR$_4$R$_5$ = 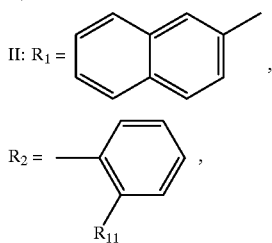

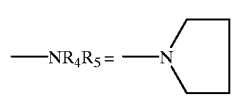

A)

II: $R_1 =$ 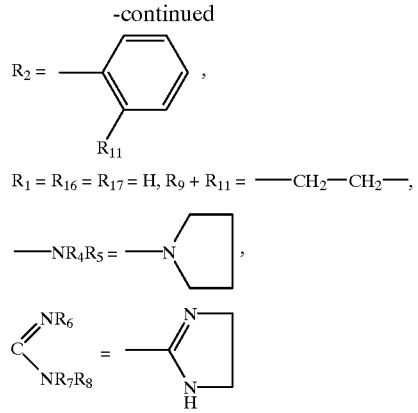

$R_2 =$ $R_3 + R_{11} =$ —CH$_2$—, $R_9 = R_{16} = R_{17} = H$,

—NR$_4$R$_5$ = 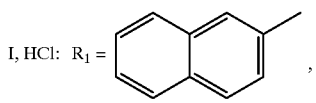

A mixture containing 0.79 g of the compound of Preparation 3.35, 0.79 g of the compound of Preparation 1.1 and 1.06 g of BOP in 10 ml of DMF is prepared, DIPEA is added in order to obtain pH =7 and the mixture is left stirring for 2 hours at RT. The mixture is extracted with EtOAc and the extracts are washed with H$_2$O, with 0.25N NaOH solution, with 0.25N HCl solution, with water and then with saturated NaCl solution. The resulting solution is dried over Na$_2$SO$_4$ and then evaporated and the residue is chromatographed on silica, eluting with a chloroform/MeOH mixture (95/5; v/v).

B)

The expected product is obtained by working as in Example 2, step B. It is purified by chromatography on Sephadex® LH 20, eluting with DCM/MeOH (3/2; v/v).

MH$^+$: 636

NMR (DMSO+TFA) : 1.40–1.80 : m : 4H; 2.60–3.60 : mt : 9H; 3.95 : s : 4H; 4.60–5.20 : m : 2H; 6.20–8.50 : m : 15H.

EXAMPLE 38

I, HCl: $R_1 =$

-continued $R_2 =$ , $R_1 = R_{16} = R_{17} = H, R_9 + R_{11} =$ —CH$_2$—CH$_2$—,

—NR$_4$R$_5$ =

533 g of the compound of Preparation 3.37 are placed in 10 ml of DMF and 205 μl of DIPEA, 573 mg of the compound of Preparation 1.2 are added and the mixture is then left overnight at RT. This mixture is diluted with 100 ml of Et$_2$O and the gum-formed is then chromatographed on Sephadex® LH 20, eluting with MeOH. The fractions of interest are combined and filtered and the residue is taken up in 6 ml of butanol and 6 ml of HCl. The organic phase is separated out after settling of the phases has taken place and is then washed with 3 ml of 1N HCl and evaporated to dryness. The product crystallizes from Et$_2$O and is filtered off and dried to give 430 mg of the expected compound.

MH$^+$: 650

NMR (DMSO+TFA) : 1.50–1.90 : m : 4H; 2.50–3.80 : m : 12H; 4.00 : ds : 4H; 4.45–4.80 : m : 1H; 5.40 : dq : 1H; 6.75–8.35 : m : 15H.

EXAMPLE 39

I, HCl: $R_1 =$ 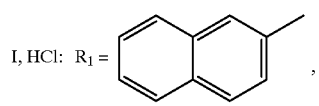

$R_2 =$ 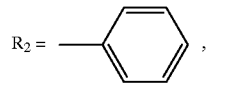, $R_3 = R_9 = R_{17} = H, R_{16} = CH_3$,

—NR$_4$R$_5$ = 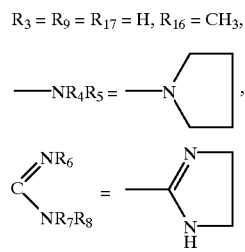

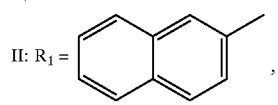

A)

II: $R_1 =$ $R_2 =$ 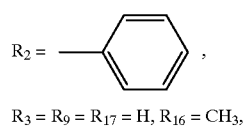, $R_3 = R_9 = R_{17} = H, R_{16} = CH_3$,

-continued

—NR$_4$R$_5$ = 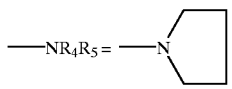

A reaction medium containing 710 mg of the compound of Preparation 3.2, 750 mg of the compound of Preparation 1.8 and 0.98 g of BOP in 12 ml of DMF is stirred and DIPEA is added to bring the mixture to pH=6. After stirring for 2 hours at RT, the mixture is extracted with EtOAc. The crude product obtained is chromatographed on silica, eluting with EtOAc/toluene (3/2; v/v). 0.52 g of the expected compound is obtained in the form of a white solid.

B)

The expected compound is obtained by working as in Example 2, step B. It is purified on Sephadex® LH 20, eluting with DCM/MeOH (3/2; v/v).

MH$^+$: 638

NMR (DMSO+TFA) : 1.40–1.75 : m : 4H; 2.30–3.20 : m : 11H; 4.00 : s : 4H; 4.60–5.40 : mt : 2H; 6.80–7.15 : m : 16H.

EXAMPLE 40

I, HCl: R$_1$ = 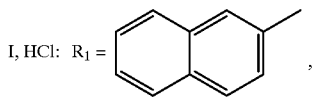,

R$_2$ = 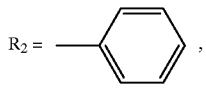,

R$_3$ = R$_9$ = R$_{16}$ = R$_{17}$ = H,

—NR$_4$R$_5$ = 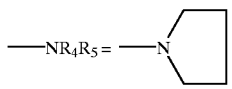,

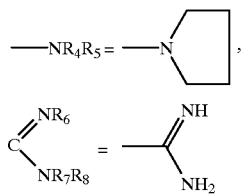

A)

0.42 g of the compound of Example 2, step A is treated with 10 ml of saturated hydrochloric ethanol at –10° C. After 72 hours at +4° C., the mixture is evaporated to dryness and is then dried under vacuum in the presence of potassium hydroxide. 0.51 g of unpurified product is obtained in the form of the hydrochloride.

B)

0.5 g of the ethyl imidate obtained in the above step is cooled to 0° C. and 10 ml of saturated ammoniacal ethanol are added, at 0° C. The mixture is allowed to return to RT. The following day, the mixture is evaporated to dryness and the residue is then chromatographed on silica, eluting with a DCM/MeO mixture (90/10; v/v), then another chromatography on Sephadex® LH 20 is carried out, eluting with MeOH. 0.15 g of the expected compound is obtained, m.p.=180° C.

MH$^+$: 598

NMR (DMSO) : 1.40–1.70 : m : 4H; 2.25–3.10 : m : 8H; 4.40–4.70 : m : 2H; 6.80–8.30 : m : 18H.

EXAMPLE 41

I, HCl: R$_1$ = 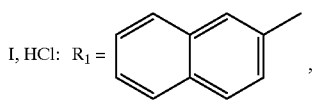,

R$_2$ = 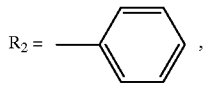,

R$_3$ = R$_9$ = R$_{16}$ = R$_{17}$ = H,

—NR$_4$R$_5$ = 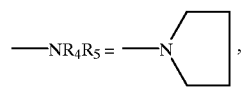,

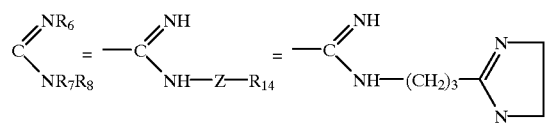

A) 4-Aminobutyronitrile.

This compound is prepared according to J. Am. Soc., 1952, 74, 1836. 6.7 ml of 4-bromobutyronitrile and 35 ml of liquid ammonia are placed in a bomb at –50° C. After closing, the bomb is left at RT for 48 hours. The residue is taken up in 50% NaOH solution and is then extracted with ether; the organic phase is dried over Na$_2$SO$_4$, evaporated to dryness and then chromatographed on silica, eluting with DCM/MeOH/NH$_4$OH (90/10/0.3; v/v/v). 1.07 g of the expected compound are obtained.

B)

0.62 g of the compound of Example 2, step A is treated with 10 ml of saturated hydrochloric ethanol at –10° C. After 24 hours at +4° C., the mixture is evaporated to dryness and the residue is then dried under vacuum. 0.8 g of unpurified product is obtained in the form of the hydrochloride.

C)

II, HCl: R$_1$ = 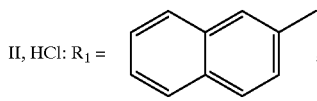,

R$_2$ = 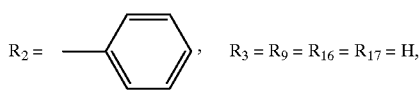, R$_3$ = R$_9$ = R$_{16}$ = R$_{17}$ = H,

—NR$_4$R$_5$ = 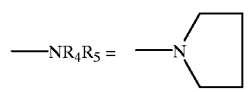,

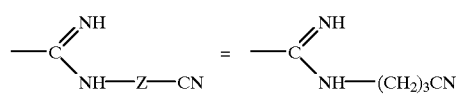

0.8 g of the compound prepared in the above step is dissolved in 10 ml of EtOH and 108 mg of 4-aminobutyronitrile diluted in 10 ml of EtOH are added dropwise. The following day, the mixture is evaporated to dryness and the residue is taken up in MeOH and a few drops of hydrochloric ether are then added. After evaporating to dryness, the residue is chromatographed on silica, eluting with DCM/MeOH (90/10; v/v) in order to obtain 0.38 g of the expected compound, m.p.=144° C.

MH$^+$: 665

D)

10 ml of saturated hydrochloric ethanol at –10° C. are added to 0.35 g of the compound obtained in the above step, at 0° C. The mixture is left in a refrigerator overnight. The following day, the mixture is evaporated to dryness and the residue is dried under vacuum in the presence of KOH. The product obtained (0.35 g) is dissolved in 80 ml of ethanol; 43 µl of ethylenediamine in 10 ml of ethanol are added dropwise, After stirring overnight, the mixture is evaporated to dryness and the residue is then chromatographed on silica, eluting with a DCM/MeOH mixture (50/50; v/v). 0.075 g of the expected compound is obtained, m.p.=195° C.

MH$^+$: 708

NMR (DMSO+TFA) : 1.35–1.50 : m : 4H; 1.80–2.00 : mt : 2H; 2.40–3.20 : m : 10H; 3.40 : mt : 2H; 3.70 : s : 4H; 4.40–4.70 : mt : 2H; 6.70–8.05 : m : 16H.

EXAMPLE 42

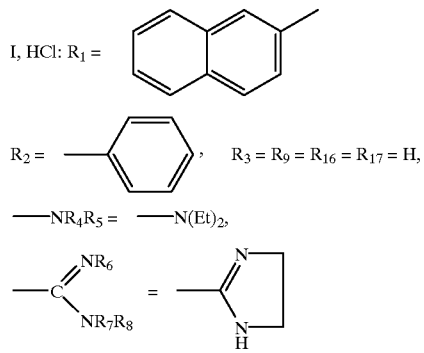

This compound is prepared according to the process described in Example 12, starting with the compounds of Preparations 1.9 and 3.2.

MH$^+$: 626

EXAMPLE 43

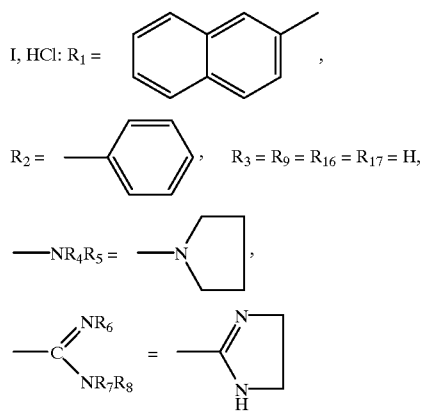

(R,R) isomer.
A)

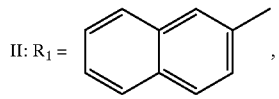

-continued

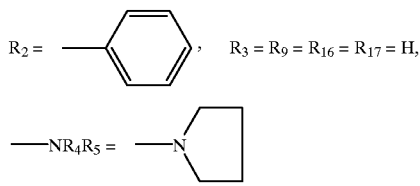

(R,R) isomer.

1.44 g of the compound of Preparation 1.13 in 40 ml of acetonitrile are mixed with 700 µl of DIPEA and 1.81 g of the compound of Preparation 3.39. The precipitate formed is dissolved in DCM and is then washed with KHSO$_4$/K$_2$SO$_4$, with saturated NaHCO$_3$ solution and with saturated NaCl solution. The resulting solution is dried and evaporated to dryness, and the product obtained (1.57 g) is used without further purification in the following step.

NMR (DMSO) : 1.40–1.60 : m : 4H; 2.20–3.10 : m : 8H; 4.40 : dq : 1H; 4.60 : dq : 1H; 6.80–8.35 : m : 18H.

B)

1 g of the product of the above step is suspended in 30 ml of HCl-saturated anhydrous ethanol at 0° C. and the mixture is left stirring for 24 hours in a refrigerator. The mixture is evaporated to dryness and dried in a desiccator in the presence of potassium hydroxide. The product is placed in 100 ml of anhydrous ethanol and 273 µl of DIPEA and 136 µl of ethylenediamine are added. After stirring for 24 hours at RT, the mixture is evaporated to dryness and the residue is taken up in a butanol/chloroform/1N HCl mixture (1/1/1; v/v/v). The phases are separated out after settling has taken place and the organic phase is then washed with 1N HCl and evaporated to dryness. The residue is chromatographed on Sephadex® LH 20, eluting with MeOH. The product obtained is treated with a butanol/chloroform/1N HCl mixture (1/1/1; v/v/v) and then concentrated. After crystallization from Et$_2$O, the crystals are filtered off, washed with Et$_2$O and then dried. 198 mg of the expected compound are obtained.

$\alpha_D^{25}$=+38.1° (c=1, DMF)

MH$^+$: 624

NMR (DMSO) ; 1.50–1.75 : m : 4H; 2.40–2.70 : mt : 2H; 2.75–3.25 : m : 6H; 4.05 : s : 4H; 4.55 : dq : 1H; 4.75 : dq : 1H; 6.95–8.20 : m : 16H; 8.50 : t : 2H; 10.80 : bs : 2H.

Using the procedure described in Example 43 and in the corresponding preparations, the various isomers described in the table below are prepared.

TABLE 13

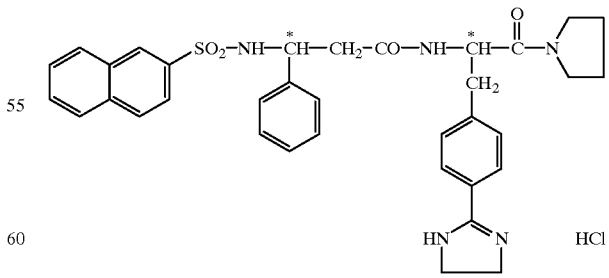

| Example | Isomer | $\alpha_D^{25}$ = (c = 1, DMF) m.p. ° C. | MH$^+$ |
|---|---|---|---|
| 44 | (S,S) | −41.9° | 624 |
| 45 | (R,S) | +42.2° | 624 |

TABLE 13-continued

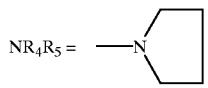

| Example | Isomer | $\alpha_D^{25}$ = (c = 1, DMF) m.p. ° C. | MH+ |
|---|---|---|---|
| 46 | (S,R) | m.p. = 195–201° C. | 624 |

NMR (DMSO) of Example 44 : 1.50–1.75 : m : 4H; 2.40–2.70 : mt : 2H; 2.75–3.25 : m : 6H; 4.05 : s : 4H; 4.55 : dq : 1H; 4.75 : dq : 1H; 6.95–8.20 : m : 16H; 8.50 : t : 2H; 10.80 : bs : 2H.

NMR (DMSO) of Example 45 : 1.65–1.90 : m: 4H; 2.40–3.45 : m : 8H; 4.05 : s : 4H; 4.55–4.85 : mt : 2H; 6.95–8.25 : m : 16H; 8.45 : t : 2H; 10.80 : bs : 2H.

NMR (DMSO+TFA) of Example 46 : 1.50–1.80 : m : 4H; 2.25–2.95 : m : 4H; 3.00–3.40 : m : 4H; 4.00 : s : 4H; 4.30–4.75 : mt : 2H; 6.80–8.15 : m : 16H.

EXAMPLE 47

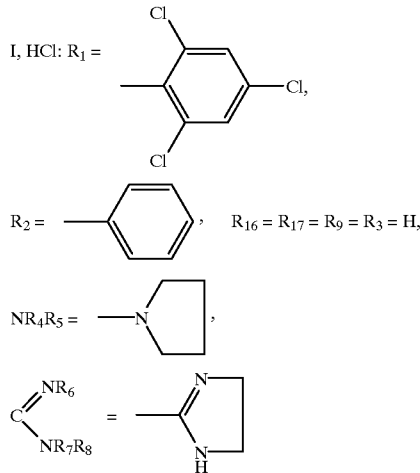

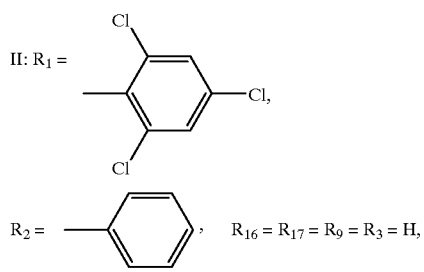

(R,R) isomer.

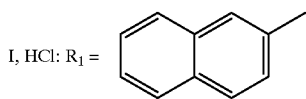

(R,R) isomer.

These 2 compounds are prepared in 2 successive steps according to the procedure described in Example 27, steps C and D, from the compound obtained in Preparation 4.2 and (2,4,6-trichlorophenyl)sulphonyl chloride.

I : $\alpha_D^{25}$=–24° (c=0.5; MeOH)
MH+: 676 with trichloroisotopic profile
NMR (DMSO) : 1.50–1.65 : m : 4H; 2.45–3.20 : m : 8H; 3.95 : s : 4H; 4.40–4.70 : mt : 2H; 7.05 : s : 5H; 7.45 : d : 2H; 7.50 : s : 2H; 7.90 : d : 2H; 8.45 : d : 1H; 8.80 : d : 1H; 10.70 : bs : 1H.

II : NMR (DMSO): 1.50–1.60 : m : 4H; 2.45–3.15 : m : 8H; 4.40–4.55 : dq : 1H; 4.60–4.75 : dq : 1H; 7.05 : s : 5H; 7.40 : d : 2H; 7.50 : s : 2H; 7.70 : d : 2H; 8.40 : d : 1H; 8.70 : d : 1H.

EXAMPLE 48

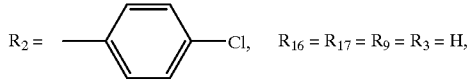

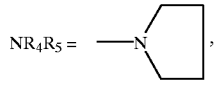

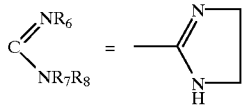

(R,R) isomer

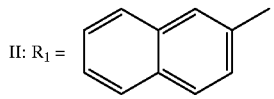

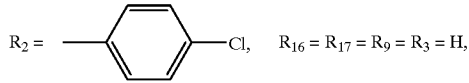

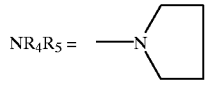

(R,R) isomer

This compound is prepared in 2 steps according to the procedure described in Example 43, starting with the compounds of Preparations 3.43 and 1.13.

I : $\alpha_D^{25}$=+57° (c=1; DMF)
MH+: 658 and 660
NMR (DMSO+TFA) : 1.40–1.60 : m : 4H; 2.25–3.10 : m : 8H; 3.95 : s : 4H; 4.45–4.65 : mt : 2H; 6.80–8.05 : m : 15H.

II : $\alpha_D^{25}$=+61° (c=1; DMF)
NMR (DMSO) : 1.40–1.60 : m : 4H; 2.25–3.10 : m : 8H; 4.35–4.60 : mt : 2H; 6.85–8.05 : m : 15H; 8.25 : t : 2H.

EXAMPLE 49

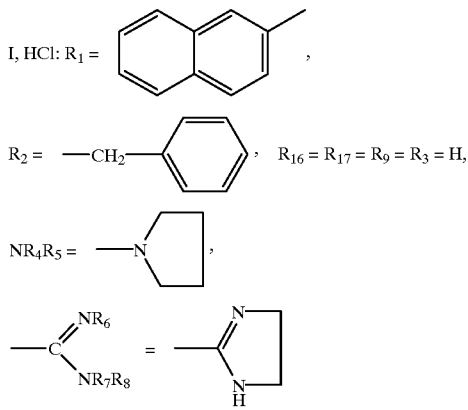

(S), (R,S) isomer.

800 mg of the compound of Preparation 1.2 in 20 ml of DMF are mixed with 250 μl of DIPEA and 933 mg of the compound of Preparation 3.45. After stirring overnight at RT, the mixture is diluted with ether and the product is then isolated by decanting. The gum formed is triturated from ether and is then chromatographed on Sephadex® LH 20, eluting with MeOH. The fractions of interest are evaporated and the residue is taken up in a butanol/EtOAc/1N HCl mixture (1/1/1; v/v/v). The organic phase is separated out after settling has taken place and evaporated to dryness, the residue is taken up in Et$_2$O and the product is filtered off and dried to give 770 mg of the expected compound.

MH$^+$: 638

NMR (DMSO+TFA) : 1.55–1.85 : m : 4H; 2.05–3.50 : m : 11H; 3.75 : s : 2H; 4.00 : s : 2H; 4.45–4.95 : mt : 1H; 6.70–8.20 : m : 16H.

EXAMPLE 50

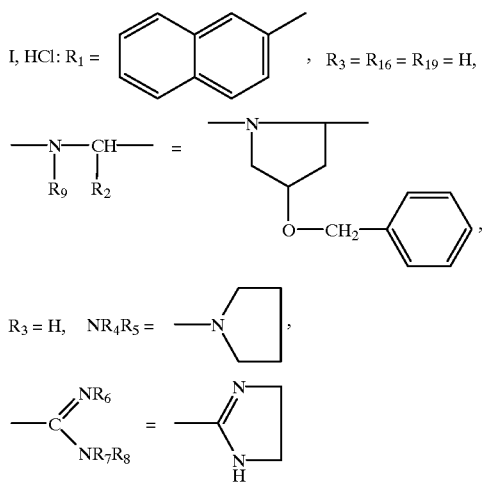

This compound is prepared from the compound of Preparation 3.46 and from the compound of Preparation 1.2 according to the procedure of Example 5.

NMR (DMSO+TFA) : 1.5–1.8 : mt : 6H; 2.7–3.6 : m : 6H; 3.6 : mt : 3H; 3.6–3.9 : mt : 8H; 4.6–4.8 : mt : 2H; 6.5 : d : 2H; 6.8–7 : m : 4H; 7.4–8.1 : m : 8H; 8.4 : d : 2H.

EXAMPLE 51

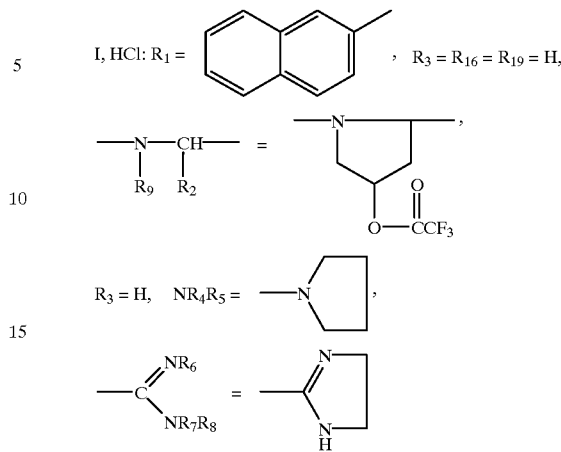

0.4 g of the compound obtained in the above example is dissolved in 8 ml of TFA and 0.2 ml of thioanisole. After stirring for 24 hours at RT, the mixture is evaporated, the residue is then taken up in Et$_2$O and the product is filtered off. It is washed several times with ether and then dried over Na$_2$SO$_4$ in order to obtain 0.385 g of the expected compound.

MH$^+$: 700

NMR (DMSO+TFA) : 1.7–2.1 : mt : 6H; 2.5 : d : 2H; 2.9–3.7 : m : 13H; 3.7–4 : m : 13H; 4.8 : mt : 1H; 5.3 : mt : 1H; 7.2–8.3 : m : 10H; 8.5 : s : 1H.

EXAMPLE 52

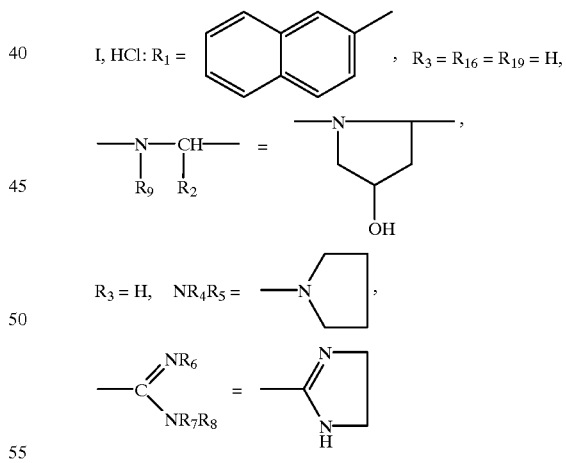

The compound obtained in the above example is dissolved in 50 ml of MeOH containing 0.106 g of KOH. After stirring for 18 hours at RT, the medium is acidified to pH=2 by addition of a saturated solution of HCl gas in dioxane. This mixture is evaporated and the residue is taken up in 5 ml of water and triturated. The product is filtered off, washed with water and then dried in order to obtain 0.160 g of the expected compound.

MH$^+$=604

EXAMPLE 53

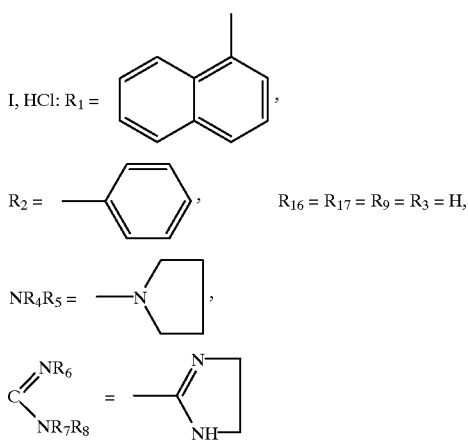

(R,R) isomer

This compound is prepared according to the procedure described in Example 43, but using the 1-naphthalenesulphonyl chloride in Preparation 3.38.

$\alpha_D^{25} = -18°$ (c=1; DMF)

MH$^+$: 624

NMR (DMSO) : 1.50–1.75 : m : 4H; 2.25–3.20 : m : 8H; 4.05 : s : 4H; 4.50–4.75 : mt : 2H; 6.85–8.70 : m : 18H (16H aromatic+2H).

EXAMPLE 54

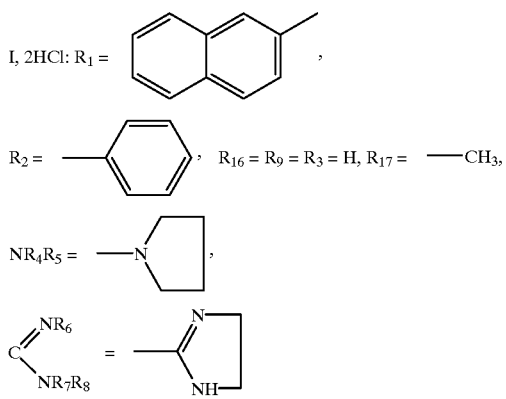

This product is prepared in 2 steps according to the procedure described for Example 2, using the compounds obtained from Preparations 3.2 and 1.14.

MH$^+$: 638

NMR (DMSO+TFA) : 0.95 : ds : 3H; 1.30–1.60 : m : 4H; 2.40–3.40 : m : 8H; 4.00 : ds : 4H; 4.75 : mt : 1H; 6.65–8.15 : m : 16H.

EXAMPLE 55

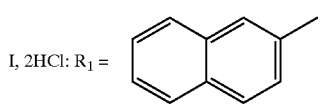 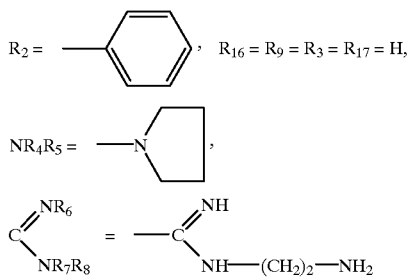

(R,R) isomer 1.30 g of the product obtained according to the procedure of Example 43, step A are stirred for 18 hours at 4° C. in 45 ml of methanol containing 22 g of HCl gas. The reaction medium is concentrated under vacuum, re-evaporated twice with MeOH and the residue is dried under vacuum in the presence of KOH. This product is dissolved in 250 ml of methanol and 0.18 ml of ethylenediamine diluted in 15 ml of methanol are added over 90 minutes, after which the mixture is stirred for a further 18 hours. The reaction medium is concentrated under vacuum to 10 ml, an Et$_2$O/HCl solution is added in order to bring the mixture to pH=3 and the resulting mixture is concentrated to dryness. The residue is purified by partition chromatography on Sephadex® G 25, using the nBuOH/iPrOH/H$_2$O solvent system (4/0.2/5; v/v/v). The product with the cyclized amidine (410 m g) as described in Example 43 is first isolated, followed by the expected product with the open amidine (410 mg).

$\alpha_D^{25} = +37.6°$ (c=0.5; DMF)

NMR (DMSO+TFA) : 1.50–1.70 : m : 4H; 2.30–3.15 : m : 10H; 3.70 : t : 2H; 4.55 : t : 1H; 4.70 t : 1H; 6.90–8.10 : m : 16H.

EXAMPLE 56

Gelatin capsule containing a 10 mg dose

| | |
|---|---|
| Compound of Example 43 (weight expressed as equivalent in non-salified form) | 10.0 mg |
| Lactose monohydrate 200 mesh | qs |
| Methylhydroxypropylcellulose 6 mPa · s | 3.0 mg |
| Crosslinked sodium carboxymethylcellulose | 4.5 mg |
| Magnesium stearate | 1.5 mg |
| Purified water for wet granulation | |

For a No. 3 size "opaque-white" gelatin capsule filled to 150 mg.

EXAMPLE 57

Splittable uncoated tablet containing a 50 mg dose

| | |
|---|---|
| Compound of Example 43 (weight expressed as equivalent in non-salified form) | 50.0 mg |
| Lactose monohydrate 200 mesh | qs |
| Microcrystalline cellulose 50 μm | 27.0 mg |
| Methylhydroxypropylcellulose 6 mPa · s | 3.6 mg |
| Crosslinked sodium carboxymethylcellulose | 5.4 mg |
| Magnesium stearate | 1.8 mg |
| Purified water for wet granulation | |

For a finished splittable uncoated tablet containing ;80 mg

EXAMPLE 58
Gelatin capsule containing a 1 mg dose

| | |
|---|---|
| Compound of Example 43 (weight expressed as equivalent in non-salified form) | 1.0 mg |
| Lactose monohydrate 200 mesh | qs |
| Methylhydroxypropylcellulose 6 mPa · s | 3.0 mg |
| Crosslinked sodium carboxymethylcellulose | 4.5 mg |
| Magnesium stearate | 1.5 mg |
| Purified water for wet granulation | |

For a NO. 3 size "opaque-white" gelatin capsule filled to 100 mg.

What is claimed is:

1. A compound of formula:

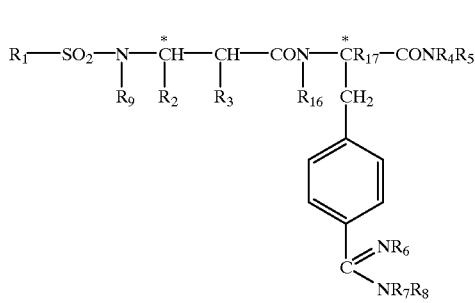

in which:

$R_1$ is a quinolyl or an isoquinolyl, the said rings being unsubstituted or substituted one or more times with $R_{10}$;

$R_2$ is a phenyl which is unsubstituted or substituted one or more times with $R_{11}$, a phenyl($C_1$–$C_4$)alkyl which is unsubstituted or substituted one or more times on the phenyl with $R_{11}$, a naphthyl which is unsubstituted or substituted one or more times with $R_{11}$, a cyclohexyl which is unsubstituted or substituted one or more times with $R_{11}$;

or $R_2$ and $R_9$ are linked together and constitute a ($C_3$–$C_5$) alkylene which is unsubstituted or substituted with $R_{12}$ or a ($C_2$–$C_4$)alkylene which is interrupted with an oxygen atom or a sulphur atom and is unsubstituted or substituted with $R_{12}$;

or $R_2$ and $R_9$, together with the carbon atom and the nitrogen atom to which they are attached, constitute tetrahydroisoquinoline which is unsubstituted or substituted one or more times with a halogen, a hydroxyl, a ($C_1$–$C_4$)alkyl, a ($C_1$–$C_4$)alkoxy or a benzyloxy;

$R_3$ is hydrogen or a hydroxyl;

$R_4$ and $R_5$ are each independently hydrogen or a ($C_1$–$C_4$) alkyl;

or $R_4$ and $R_5$, together with the nitrogen atom to which they are attached, constitute a heterocyclic radical chosen from 1-pyrrolidinyl, 1-piperidyl, perhydro-1-azepinyl, 4-morpholinyl, 4-oxo-1-piperidyl, dihydro-1-pyrrolyl or dihydro-2-imidazolyl, the said heterocyclic radicals being unsubstituted or substituted one or more times with $R_{13}$;

$R_6$ is hydrogen and $R_6$ can also be $R_8$ when $R_7$ is hydrogen;

$R_7$ is hydrogen or a ($C_1$–$C_4$)alkyl;

$R_8$ is hydrogen; a benzyl which is unsubstituted or substituted on the phenyl one or more times with $R_{13}$; or a group $ZR_{14}$;

or $R_7$ and $R_8$, together with the nitrogen atom to which they are attached, constitute a heterocyclic radical chosen from 1-pyrrolidinyl, 1-piperidyl, 1-perhydro-1-azepinyl, 4-morpholinyl, tetrahydro-2-pyrimidinyl, 1-piperazinyl or 1-piperazinyl substituted in position 4 with a ($C_1$–$C_4$)alkyl or a benzyl;

or, when $R_7$ is hydrogen, $R_6$ and $R_8$ are linked together to form a ($C_2$–$C_4$)alkylene which is unsubstituted or substituted one or more times with a ($C_1$–$C_4$)alkyl;

$R_9$ is hydrogen, a ($C_1$–$C_4$)alkyl or a phenyl($C_1$–$C_4$)alkyl which is unsubstituted or substituted on the phenyl one or more times with $R_{11}$;

$R_{10}$ is a halogen, a ($C_1$–$C_4$)alkyl, a ($C_1$–$C_4$)alkoxy, a hydroxyl, an amino, a ($C_1$–$C_4$)alkylamino or a di($C_1$–$C_4$)alkylamino;

$R_{11}$ is a halogen, a ($C_1$–$C_4$)alkyl, a trifluoromethyl, a phenyl, a hydroxyl, a ($C_1$–$C_4$)alkoxy or a benzyloxy;

or $R_{11}$ is in the ortho position to the phenyl representing $R_2$ and forms with $R_3$ a methylene group or an ethylene group;

or $R_{11}$ is in the ortho position to the phenyl representing $R_2$ and forms with $R_9$ a methylene group or an ethylene group;

$R_{12}$ is a halogen, a ($C_1$–$C_4$)alkyl, a hydroxyl, a ($C_1$–$C_4$) alkoxy, a benzyloxy, an oxo, a phenyl, an acetyloxy or a trifluoroacetyloxy;

$R_{13}$ is a ($C_1$–$C_4$)alkyl, a halogen or a hydroxyl;

$R_{14}$ is a methyl, an amino, a ($C_1$–$C_4$)alkylamino, a di($C_1$–$C_4$)alkylamino, a tri($C_1$–$C_4$)alkylammonium, an amidino, a ($C_1$–$C_4$)alkylamidino, a guanidino, a ($C_1$–$C_4$)alkylguanidino, a hydroxyl, a ($C_1$–$C_4$)alkoxy, a ($C_1$–$C_4$)alkoxycarbonyl, a group —AlkN($R_{15}$)Alk'N ($R_{15}$)$_2$, or a heterocyclic radical chosen from 1-pyrrolidinyl, 1-piperidyl, perhydro-1-azepinyl, pyridyl, imidazolyl, dihydroimidazolyl, inidazolidinyl, pyrimidinyl and indolyl;

$R_{15}$ and $R'_{15}$ are, independently of each other, hydrogen or a ($C_1$–$C_4$)alkyl;

$R_{16}$ is hydrogen or a methyl, or $R_{16}$ forms with $R_9$ a methylene group;

$R_{17}$ is hydrogen or a methyl;

Alk and Alk' are, independently of each other, a ($C_1$–$C_4$) alkylene;

Z is a ($C_2$–$C_{12}$)alkylene or a ($C_1$–$C_6$)alkylene which is interrupted or substituted with a ($C_5$–$C_7$)cycloalkyl or with a phenyl;

C* is an asymmetric carbon atom;

as well as the salts thereof with inorganic or organic acids.

2. A compound of formula (I) according to claim 1, in which:

$R_1$ is a quinolyl or an isoquinolyl, the said rings being unsubstituted or substituted one or more times with $R_{10}$;

$R_2$ is a phenyl which is unsubstituted or substituted one or more times with $R_{11}$, a phenyl($C_1$–$C_4$)alkyl which is unsubstituted or substituted one or more times on the phenyl with $R_{11}$, or a naphthyl which is unsubstituted or substituted one or more times with $R_{11}$;

or $R_2$ and $R_9$ are linked together and constitute a ($C_3$–$C_5$) alkylene which is unsubstituted or substituted with $R_{12}$ or a ($C_2$–$C_4$)alkylene which is interrupted with an oxygen atom or a sulphur atom and is unsubstituted or substituted with $R_{12}$;

or $R_2$ and $R_9$ together with the carbon atom and the nitrogen atom to which they are attached, constitute tetrahydroisoquinoline which is unsubstituted or substituted one or more times with a halogen, a hydroxyl, a $(C_1-C_4)$alkyl, a $(C_1-C_4)$alkoxy or a benzyloxy;

$R_3$ is hydrogen or a hydroxyl;

$R_4$ and $R_5$ are each independently hydrogen or a $(C_1-C_4)$alkyl;

or $R_4$ and $R_5$, together with the nitrogen atom to which they are attached, constitute a heterocyclic radical chosen from 1-pyrrolidinyl, 1-piperidyl, perhydro-1-azepinyl, 4-morpholinyl or 4-oxo-1-piperidyl, the said heterocyclic radicals being unsubstituted or substituted with $R_{13}$;

$R_6$ is hydrogen, $R_6$ can also be $R_8$ when $R_7$ is hydrogen;

$R_7$ is hydrogen or a $(C_1-C_4)$alkyl;

$R_8$ is hydrogen; a benzyl which is unsubstituted or substituted on the phenyl one or more times with $R_{13}$; or a group $ZR_{14}$;

or $R_7$ and $R_8$, together with the nitrogen atom to which they are attached, constitute a heterocyclic radical chosen from 1-pyrrolidinyl, 1-piperidyl, 1-perhydro-1-azepinyl, 4-morpholinyl, 1-piperazinyl or 1-piperazinyl substituted in position 4 with a $(C_1-C_4)$alkyl or a benzyl;

or, when $R_7$ is hydrogen, $R_6$ and $R_8$ are linked together to form a $(C_2-C_4)$alkylene which is unsubstituted or substituted one or more times with a $(C_1-C_4)$alkyl;

$R_9$ is hydrogen, a $(C_1-C_4)$alkyl or a phenyl$(C_1-C_4)$alkyl which is unsubstituted or substituted on the phenyl one or more times with $R_{11}$;

$R_{10}$ is a halogen, a $(C_1-C_4)$alkyl, a $(C_1-C_4)$alkoxy, a hydroxyl, an amino, a $(C_1-C_4)$alkylamino or a di$(C_1-C_4)$alkylamino;

$R_{11}$ is a halogen, a $(C_1-C_4)$alkyl, a hydroxyl, a $(C_1-C_4)$alkoxy or a benzyloxy;

$R_{12}$ is a halogen, a $(C_1-C_4)$alkyl, a hydroxyl, a $(C_1-C_4)$alkoxy, a benzyloxy, an oxo or a phenyl;

$R_{13}$ is a $(C_1-C_4)$alkyl, a halogen or a hydroxyl;

$R_{14}$ is a methyl, an amino, a $(C_1-C_4)$alkylamino, a di$(C_1-C_4)$alkylamino, a tri$(C_1-C_4)$alkylammonium, an amidino, a $(C_1-C_4)$alkylamidino, a guanidino, a $(C_1-C_4)$alkylguanidino, a hydroxyl, a $(C_1-C_4)$alkoxy, a $(C_1-C_4)$alkoxycarbonyl, a group —AlkN$(R_{15})$Alk'N $(R'_{15})_2$, or a heterocyclic radical chosen from 1-pyrrolidinyl, 1-piperidyl, perhydro-1-azepinyl, pyridyl, imidazolyl, dihydroimidazolyl, imidazolidinyl, pyrimidinyl and indolyl;

$R_{15}$ and $R'_{15}$ are, independently of each other, hydrogen or a $(C_1-C_4)$alkyl;

$R_{16}$ is hydrogen;

$R_{17}$ is hydrogen;

Alk and Alk' are, independently of each other, a $(C_1-C_4)$alkylene;

Z is a $(C_2-C_{12})$alkylene or a $(C_1-C_6)$alkylene which is interrupted or substituted with a $(C_5-C_7)$cycloalkyl or with a phenyl;

as well as the salts thereof with inorganic or organic acids.

3. A compound of formula (I) according to claim 1 which satisfies at least one of the following conditions:

a—$R_1$ is a quinolyl; $R_2$, $R_3$, $R_4$, $R_5$, $R_6$, $R_7$, $R_8$, $R_9$, $R_{16}$ and $R_{17}$ being as defined in claim 1;

b—$R_2$ is a phenyl which is unsubstituted or substituted with $R_{11}$; $R_1$, $R_3$, $R_4$, $R_5$, $R_6$, $R_7$, $R_8$, $R_9$, $R_{16}$ and $R_{17}$ being as defined in claim 1;

c—NR$_4$R$_5$ is a 1-pyrrolidinyl group; $R_1$, $R_2$, $R_3$, $R_6$, $R_7$, $R_8$, $R_9$, $R_{16}$ and $R_{17}$ being as defined in claim 1;

d—C(NR$_6$)NR$_7$R$_8$ is a 4,5-dihydro-2-imidazolyl; $R_1$, $R_2$, $R_3$, $R_4$, $R_5$, $R_9$, $R_{16}$ and $R_{17}$ being as defined in claim 1;

e—$R_3$=$R_9$=$R_{16}$=$R_{17}$=H; $R_1$, $R_2$, $R_4$, $R_5$, $R_6$, $R_7$ and $R_8$ being as defined in claim 1;

and the salts thereof with inorganic or organic acids.

4. A compound according to claim 3 of formula:

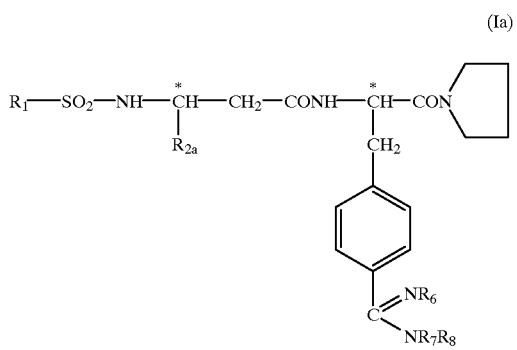

(Ia)

in which:

$R_{2a}$ is a phenyl which is unsubstituted or substituted in a meta or para position with $R_{11}$; a 1-naphthyl or a 2-naphthyl;

$R_1$, $R_6$, $R_7$, $R_8$ and $R_{11}$ are as defined in claim 1 for (I);

and the salts thereof with inorganic or organic acids.

5. A compound according to claim 4 of formula:

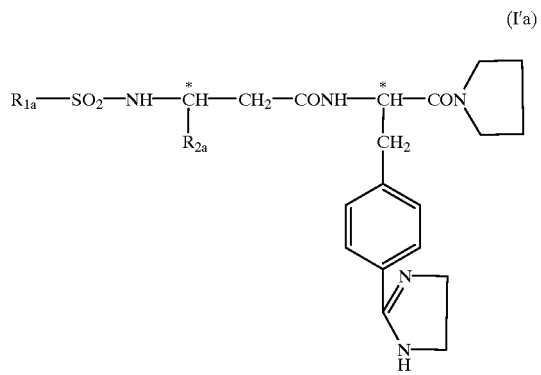

(I'a)

in which:

$R_{1a}$ is a 2-quinolyl;

$R_{2a}$ is as defined in claim 4 for (Ia);

and the salts thereof with inorganic or organic acids.

6. A compound of formula (I'a) according to claim 5, in which $R_{2a}$ is a phenyl which is unsubstituted or substituted in a meta position or para position with $R_{11}$.

7. A compound according to claim 1 having (R,R) isomerism on the C*-labelled carbon atoms.

8. A process for the preparation of the compounds of formula (I) according to claim 1 wherein:

a1) a compound of formula:

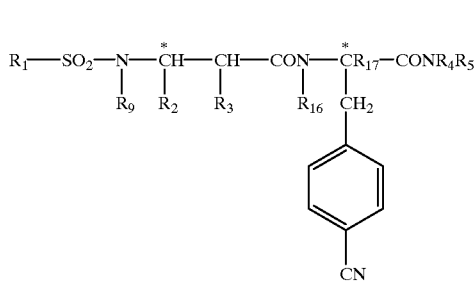
(II)

in which $R_1$, $R_2$, $R_3$, $R_4$, $R_5$, $R_9$, $R_{16}$, $R_{17}$ and C* have the definitions given in claim 1 for (I), in the form of a pure enantiomer or a mixture of isomers in any proportion, is treated with an alcohol of formula R—OH in which R is a $(C_1-C_4)$alkyl, in acidic medium, in order to form an intermediate imidate which is reacted with an amine of formula $HNR_7R_8$ (III) or a diamine of formula $H_2NR_6R_8NH_2$ (IV) in which $R_6$, $R_7$ and $R_8$ have the definitions given in claim 1 for (I);

b1) the compound of formula (I) thus obtained is isolated in base form or salt form, c1) where appropriate, another salt of the compound of formula (I) is prepared.

9. A process for the preparation of a compound of formula (I) according to claim 1 wherein:

a2) a compound of formula:

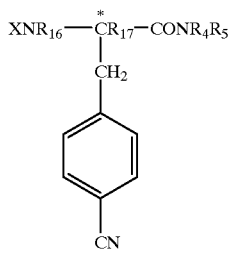
(VIa)

In which X is hydrogen or a Boc group and $R_4$, $R_5$ and C* are as defined for (I) in claim 1, in the form of a pure enantiomer or a mixture of isomers in any proportion, is treated with an alcohol of formula R—OH in which R is a $(C_1-C_4)$alkyl, in acidic medium, in order to form an intermediate imidate which is reacted with an amine of formula $HNR_7R_8$ (III) or a diamine of formula $H_2NR_6R_8NH_2$ (IV) in which $R_6$, $R_7$ and $R_8$ have the definitions given for (I) in claim 1:

b2) the compound thus obtained, of formula:

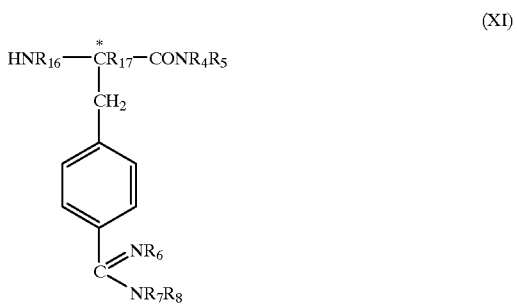
(XI)

is coupled either with a compound of formula:

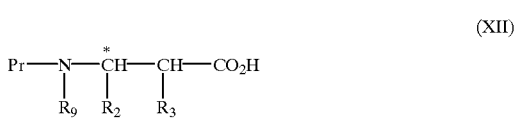
(XII)

in which $R_2$, $R_3$ and $R_9$ are as defined for (I) in claim 1 and Pr is a protecting group, then, after deprotection of the amine in acidic medium, a sulphonyl halide of formula $R_1SO_2Hal$ in which $R_1$ is as defined for (I) in claim 1 and Hal is a halogen is reacted;

or with a compound of formula:

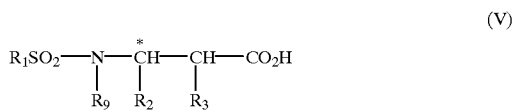
(V)

in which $R_1$, $R_2$, $R_3$ and $R_9$ are as defined for (I) in claim 1:

c2) the compound of formula (1) thus obtained is isolated in base form or in salt form;

d2) where appropriate, another salt of the compound of formula (I) is prepared.

10. A pharmaceutical composition comprising, as active principle, a compound according to claim 1.

11. A compound according to claim 6 having (R,R) isomerism on the C*-labelled carbon atoms.

12. A compound according to claim 6 in which $R_{1a}$ is 2-quinolyl and $R_{2a}$ is phenyl.

13. A compound according to claim 12 having (R,R) isomerism on the C*-labelled carbon atoms.

14. A pharmaceutical composition comprising, as active principle, a compound according to claim 2.

15. A pharmaceutical composition comprising, as active principle, a compound according to claim 3.

16. A pharmaceutical composition comprising, as active principle, a compound according to claim 4.

17. A pharmaceutical composition comprising, as active principle, a compound according to claim 5.

18. A pharmaceutical composition comprising, as active principle, a compound according to claim 6.

19. A pharmaceutical composition comprising, as active principle, a compound according to claim 7.

20. A pharmaceutical composition comprising, as active principle, a compound according to claim 11.

21. A pharmaceutical composition comprising, as active principle, a compound according to claim 12.

22. A pharmaceutical composition comprising, as active principle, a compound according to claim 13.

23. A method for the treatment or prevention of diseases involving the bradykinin receptors which comprises administering to a patient in need of such treatment an effective amount of a compound according to claim 1.

24. A method for the treatment or prevention of diseases involving the bradykinin receptors which comprises administering to a patient in need of such treatment an effective amount of a compound according to claim 12.

25. A method for the treatment or prevention of diseases involving the bradykinin receptors which comprises administering to a patient in need of such treatment an effective amount of a compound according to claim 13.

26. A method for the treatment or prevention of diseases involving the bradykinin receptors which comprises administering to a patient in need of such treatment an effective amount of a compound according to claim 14.

27. A method for the treatment or prevention of diseases involving the bradykinin receptors which comprises administering to a patient in need of such treatment an effective amount of a compound according to claim 5.

28. A method for the treatment or prevention of diseases involving the bradykinin receptors which comprises administering to a patient in need of such treatment an effective amount of a compound according to claim 6.

29. A method for the treatment or prevention of diseases involving the bradykinin receptors which comprises administering to a patient in need of such treatment an effective amount of a compound according to claim 7.

30. A method for the treatment or prevention of diseases involving the bradykinin receptors which comprises administering to a patient in need of such treatment an effective amount of a compound according to claim 11.

31. A method for the treatment or prevention of diseases involving the bradykinin receptors which comprises administering to a patient in need of such treatment an effective amount of a compound according to claim 12.

32. A method for the treatment or prevention of diseases involving the bradykinin receptors which comprises administering to a patient in need of such treatment an effective amount of a compound according to claim 13.

* * * * *